US010012636B2

(12) United States Patent
Wang et al.

(10) Patent No.: US 10,012,636 B2
(45) Date of Patent: *Jul. 3, 2018

(54) LABEL-FREE MONITORING OF EXCITATION-CONTRACTION COUPLING AND EXCITABLE CELLS USING IMPEDANCE BASED SYSTEMS WITH MILLISECOND TIME RESOLUTION

(71) Applicant: ACEA Biosciences, Inc., San Diego, CA (US)

(72) Inventors: Xiaobo Wang, San Diego, CA (US); Yama A. Abassi, San Diego, CA (US); Biao Xi, San Diego, CA (US); Wen Fu Zhang, San Diego, CA (US); Xiao Xu, San Diego, CA (US)

(73) Assignee: ACEA Biosciences, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/651,882

(22) Filed: Jul. 17, 2017

(65) Prior Publication Data

US 2018/0095064 A1 Apr. 5, 2018

Related U.S. Application Data

(63) Continuation of application No. 12/435,569, filed on May 5, 2009, now Pat. No. 9,709,548.

(Continued)

(51) Int. Cl.
*C40B 30/06* (2006.01)
*G01N 7/00* (2006.01)
(Continued)

(52) U.S. Cl.
CPC ................ *G01N 33/4836* (2013.01)

(58) Field of Classification Search
CPC ...... C40B 30/06; G01N 7/00; G01N 33/4836; C12Q 1/00
See application file for complete search history.

(56) References Cited

U.S. PATENT DOCUMENTS 2,656,508 A 10/1953 Coulter
3,259,842 A 7/1966 Coulter et al.
(Continued)

FOREIGN PATENT DOCUMENTS

EP 1138758 10/2001
EP 1195432 4/2002
(Continued)

OTHER PUBLICATIONS

Baumann et al. "Microelectronic sensor system for microphysical application on living cells," Sensors and Actuators,1999:77-89.
(Continued)

*Primary Examiner* — Reza Ghafoorian
(74) *Attorney, Agent, or Firm* — Wagenknecht IP Law Group PC

(57) ABSTRACT

A system for monitoring impedance of excitable cells in vitro, which includes a device for monitoring cell-substrate impedance at 20 millisecond resolution, which includes a nonconductive substrate with one or more electrode arrays fabricated in one or more wells, wherein cell attachment on the substrate can result in a detectable change in impedance between electrodes within each electrode array; an impedance analyzer capable of impedance measurement at 20 millisecond time resolution; electronic circuitry that can engage said device and selectively connect said two or more electrode arrays of said device to said impedance analyzer; and a software program that controls said electronic circuitry and records and analyzes data obtained from said impedance analyzer.

13 Claims, 50 Drawing Sheets

Related U.S. Application Data

(60) Provisional application No. 61/191,684, filed on Sep. 11, 2008, provisional application No. 61/126,533, filed on May 5, 2008.

(51) Int. Cl.
*C12Q 1/00* (2006.01)
*G01N 33/483* (2006.01)

(56) References Cited

U.S. PATENT DOCUMENTS

| | | |
|---|---|---|
| 3,743,581 A | 7/1973 | Cady et al. |
| 3,890,201 A | 6/1975 | Cady et al. |
| 4,072,578 A | 2/1978 | Cady et al. |
| 4,225,410 A | 9/1980 | Pace |
| 4,686,190 A | 8/1987 | Cramer et al. |
| 4,920,047 A | 4/1990 | Giaever et al. |
| 5,001,048 A | 3/1991 | Taylor et al. |
| 5,134,070 A | 7/1992 | Casnig |
| 5,187,096 A | 2/1993 | Giaever et al. |
| 5,218,312 A | 6/1993 | Moro |
| 5,247,827 A | 9/1993 | Shah |
| 5,278,048 A | 1/1994 | Parce et al. |
| 5,284,753 A | 2/1994 | Goodwin |
| 5,514,555 A | 5/1996 | Springer et al. |
| 5,563,067 A | 10/1996 | Sugihara et al. |
| 5,601,997 A | 2/1997 | Tchao et al. |
| 5,622,872 A | 4/1997 | Ribi |
| 5,626,734 A | 5/1997 | Docoslis et al. |
| 5,643,742 A | 7/1997 | Malin et al. |
| 5,725,563 A | 3/1998 | Klotz |
| 5,766,934 A | 6/1998 | Guiseppi-Elie |
| 5,800,467 A | 9/1998 | Park et al. |
| 5,801,055 A | 9/1998 | Henderson |
| 5,810,725 A | 9/1998 | Sugihara et al. |
| 5,824,494 A | 10/1998 | Feldberg |
| 5,851,489 A | 12/1998 | Wolf et al. |
| 5,981,268 A | 11/1999 | Kovacs et al. |
| 6,033,628 A | 3/2000 | Kaltenbach et al. |
| 6,051,422 A | 4/2000 | Kovacs et al. |
| 6,132,683 A | 10/2000 | Sugihara et al. |
| 6,169,394 B1 | 1/2001 | Frazier et al. |
| 6,232,062 B1 | 5/2001 | Keyyem et al. |
| 6,235,520 B1 | 5/2001 | Malin et al. |
| 6,280,586 B1 | 8/2001 | Wolf et al. |
| 6,288,527 B1 | 9/2001 | Sugihara et al. |
| 6,368,795 B1 | 4/2002 | Hefti |
| 6,368,851 B1 | 4/2002 | Baumann et al. |
| 6,376,233 B1 | 4/2002 | Wolf et al. |
| 6,377,057 B1 | 4/2002 | Borkholder |
| 6,440,662 B1 | 8/2002 | Gerwen et al. |
| 6,448,030 B1 | 9/2002 | Rust et al. |
| 6,448,794 B1 | 9/2002 | Cheng et al. |
| 6,461,808 B1 | 10/2002 | Bodner et al. |
| 6,472,144 B2 | 10/2002 | Malin et al. |
| 6,485,905 B2 | 11/2002 | Hefti |
| 6,492,175 B1 | 12/2002 | Muller et al. |
| RE37,977 E | 2/2003 | Sugihara et al. |
| 6,535,822 B2 | 3/2003 | Mansky et al. |
| 6,566,079 B2 | 5/2003 | Hefti |
| 6,573,063 B2 | 6/2003 | Hochman |
| 6,596,499 B2 | 7/2003 | Jalink |
| 6,626,902 B1 | 9/2003 | Kucharczyk et al. |
| 6,627,461 B2 | 9/2003 | Chapman et al. |
| 6,630,359 B1 | 10/2003 | Caillat et al. |
| 6,637,257 B2 | 10/2003 | Sparks |
| 6,638,743 B2 | 10/2003 | Baumann et al. |
| RE38,323 E | 11/2003 | Sugihara et al. |
| 6,649,402 B2 | 11/2003 | Van der Weide et al. |
| 6,686,193 B2 | 2/2004 | Maher et al. |
| 6,716,620 B2 | 4/2004 | Bashir et al. |
| 6,723,523 B2 | 4/2004 | Lynes et al. |
| 6,803,229 B2 | 10/2004 | Martin et al. |
| 6,835,552 B2 | 12/2004 | Miles et al. |
| 6,846,639 B2 | 1/2005 | Miles et al. |
| 6,852,525 B1 | 2/2005 | Cantor |
| 6,998,249 B1 | 2/2006 | McKim et al. |
| 7,010,347 B2 | 3/2006 | Schecter |
| 7,192,752 B2 | 3/2007 | Xu et al. |
| 7,208,279 B2 | 4/2007 | Gilchrist et al. |
| 7,294,334 B1 | 11/2007 | Michal et al. |
| 7,399,631 B2 | 7/2008 | Giaever et al. |
| 7,459,303 B2 | 12/2008 | Wang et al. |
| 7,468,255 B2 | 12/2008 | Xu et al. |
| 7,470,533 B2 | 12/2008 | Xu et al. |
| 7,476,827 B1 | 1/2009 | Bhuller et al. |
| 7,553,448 B2 | 6/2009 | Kumar et al. |
| 7,560,269 B2 | 7/2009 | Wang et al. |
| 7,732,127 B2 | 6/2010 | Wang et al. |
| 7,842,246 B2 | 11/2010 | Wohlstadler et al. |
| 7,876,108 B2 | 1/2011 | Abassi et al. |
| 8,026,080 B2 | 9/2011 | Wang et al. |
| 8,041,515 B2 | 10/2011 | Wang et al. |
| 8,206,903 B2 | 6/2012 | Abassi et al. |
| 8,263,375 B2 | 9/2012 | Abassi et al. |
| 8,344,742 B2 | 1/2013 | Abassi et al. |
| 8,420,363 B2 | 4/2013 | Wang et al. |
| 8,916,357 B2 | 12/2014 | Abassi et al. |
| 8,921,041 B2 | 12/2014 | Wang et al. |
| 9,399,787 B2 | 7/2016 | Abassi et al. |
| 9,709,548 B2 | 7/2017 | Wang et al. |
| 2002/0090649 A1 | 7/2002 | Chan et al. |
| 2003/0032000 A1 | 2/2003 | Liu et al. |
| 2003/0072549 A1 | 4/2003 | Facer et al. |
| 2003/0104512 A1 | 6/2003 | Freeman et al. |
| 2003/0116447 A1 | 6/2003 | Surridge et al. |
| 2003/0157587 A1 | 8/2003 | Gomez et al. |
| 2003/0166015 A1 | 9/2003 | Zarowitz et al. |
| 2003/0211500 A1 | 11/2003 | Woosley |
| 2004/0091397 A1 | 5/2004 | Picard |
| 2004/0106095 A1 | 6/2004 | Thomson et al. |
| 2004/0146849 A1 | 7/2004 | Huang et al. |
| 2005/0014130 A1 | 1/2005 | Liu et al. |
| 2006/0050596 A1 | 3/2006 | Abassi et al. |
| 2006/0057771 A1 | 3/2006 | Kovacs et al. |
| 2006/0161073 A1 | 7/2006 | Singer et al. |
| 2006/0216203 A1 | 9/2006 | Fuller et al. |
| 2007/0042347 A1 | 2/2007 | Rosen et al. |
| 2007/0212423 A1 | 9/2007 | Epstein et al. |
| 2008/0190783 A1 | 8/2008 | Hyland |
| 2008/0286750 A1 | 11/2008 | Xu et al. |
| 2009/0017465 A1 | 1/2009 | Xu et al. |
| 2009/0142790 A1 | 6/2009 | Fang et al. |
| 2011/0039294 A1 | 2/2011 | Wang et al. |
| 2011/0231103 A1 | 9/2011 | Fang |
| 2011/0300569 A1 | 12/2011 | Li et al. |
| 2012/0142031 A1 | 6/2012 | Xu et al. |
| 2012/0322050 A1 | 12/2012 | Abassi et al. |
| 2013/0123136 A1 | 5/2013 | Abassi et al. |
| 2014/0203818 A1 | 7/2014 | Wang et al. |
| 2015/0125894 A1 | 5/2015 | Laing et al. |
| 2015/0185206 A1 | 7/2015 | Abassi et al. |
| 2017/0269062 A1 | 9/2017 | Abassi et al. |

FOREIGN PATENT DOCUMENTS

| | | |
|---|---|---|
| EP | 1040345 B1 | 3/2006 |
| EP | 2213721 | 8/2010 |
| EP | 2291645 | 9/2015 |
| WO | 1996/01836 | 1/1996 |
| WO | 1999/66329 | 12/1999 |
| WO | 2000/37628 | 6/2000 |
| WO | 2000/70343 | 11/2000 |
| WO | 2000/71669 | 11/2000 |
| WO | 2001/25769 | 4/2001 |
| WO | 2001/038873 | 5/2001 |
| WO | 2001/79529 | 10/2001 |
| WO | 2002/004943 | 1/2002 |
| WO | 2002/042766 | 5/2002 |
| WO | 2003/016887 | 2/2003 |
| WO | 2004/010103 | 1/2004 |
| WO | 2005/005979 | 1/2005 |
| WO | 2005/047482 | 5/2005 |
| WO | 2005/077104 | 8/2005 |

(56) References Cited

FOREIGN PATENT DOCUMENTS

| WO | 2006/017762 | 2/2006 |
|---|---|---|
| WO | 2009/137440 | 11/2009 |
| WO | 2010/129725 | 11/2009 |
| WO | 2011/146531 | 11/2011 |
| WO | 2012/043820 | 4/2012 |
| WO | 2014/085727 | 6/2014 |

OTHER PUBLICATIONS

Berens et al. "The role of extracelluar matrix in human astrocytoma migration and proliferation studied in a microliter scale assay," Clin. Exp. Metastasis, 1994; 12(6):405-415.
Bieberich et al. "Neuronal differentiation and synapse formation of PC12 and embryonic stem cells on interdigitated microelectrode arrays: Contact structures for neuron-to-electrode signal transmission (NEST)," Biosensors and Bioelectronics 2004; 19:923-931.
Burnett et al. "Fluorescent imaginng of electrically stimulated cells," Journal of Biomolecular Screening 2003; 8(6):660-667.
Cady et al. "Electrical Impedance Measurements: Rapid Method for Detecting and Monitoring Microorganisms," J. Clin. Mirobiol., 1978; 7(3):265-272.
Ehret et al. "Monitoring of cellular behaviour by impedance measurements on interdigitated electrode structures," Biosensors and Bioelectronics 1997; 12(1):29-41.
Ehret et al. "On-line control of cellular adhesion with impedance measurements using interdigitated electrode structures," Med. Biol. Eng. Comput., 1998; 36:365-370.
Giaever et al. "Micromotion of mammalian cells measured electrically," Proc. Natl. Acad. Sci. USA, 1991; 8:7896-7900.
Giaever et al. "Monitoring fibroblast behavior in tissue culture with an applied electric field," Proc. Natl. Acad. Sci. USA; 1984; 81(June):3761-3764.
Henning et al. "Approach to a mutliparametric sensor-chip-based tumor chemosensitivity assay," Anti-Cancer Drugs 2001; 12:21-32.
Hidalgo et al. "Characterization of the human colon carcinoma cell line (Caco-2) as a model system for intestinal epithelial Permeability," 1989; 96:736-749.
Hug, Thomas. "Biophysical methods for monitoring cell-substrate interactions in drug discovery, Assay and Drug Development Technologies," 2003; 1(3):479-488.
Kleinman et al. "Basement membrane complexes with biological activity," Biochemistry, 1986, 25(2):312-318.
Kowolenko et al. "Measurement of macrophage adherence and spreading with weak electric fields," Journal of Immunological Methods, 1990, 127:71-77.
Lo et al. "Monitoring motion of confluent cells in tissue culture," Experimental Cell Research, 1983, 204:102-109.
Luong et al. "Monitoring motility, spreading and mortality of adherent insect cells using an impedance sensor," Anal. Chem., 2001, 73(8):1844-1848.
Neher, Erwin. "Molecular biology meets microelectronics," Nature Biotechnology, 2001, 19:114.
Ong et al. "Remote query resonant-circuit sensors for monitoring of bacterial growth: Application to food quality control," Sensors, 2002, 2:219-232.
Pancrazio et al. "Portable cell-based biosensor system for toxin detection," Sensors and Actuators, 1998, 53:179-185.
Slaughter et al. "Artificial neural network for temporal impedance recognition of neurotoxins," International Joint conference on Neural Networks, Jul. 16-21, 2006, 2001-2008.
Stenger et al. "Detection of physiologically active compounds using cell-based biosensors," Trends in Biotechnology, 2001, 19(8):304-309.
Wang et al. "A theoretical method of electrical field analysis for dielectrophoretic electrode arrays using Green's theorem," J. Phys. D: Appl. Phys., 1996, 29:1649-1660.

Wegener et al. "Electric cell-substrate impedance sensing (ECIS) as noninvasive means to monitor the kinetics of cell spreading to artificial surfaces," Experimental Cell Research, 2000, 259:158-166.
Wolf et al. "Monitoring of cellular signalling and metabolism with modular sensor-technique: The PhysioControl-Microsystem (PCM)," Biosensors and Bioelectronics, 1998, 13:501-509.
Xiao et al. "Assessment of cytotoxicity using electric cell-substrate impedance sensing: Concentration and time response function approach," Anal. Chem, 2002, 74:5748-5753.
Xiao et al. "An in-depth analysis of electric cell-substrate impedance sensing to study the attachment and spreading of mammalian cells," Anal. Chem., 2002, 74(6):1333-1339.
Xiao et al. "On-line monitoring of cell growth and cytotoxicity using electric cell-substrate impedance sensing (ECIS)," Biotechnol. Prog., 2003, 19:1000-1005.
EP09743426.0 European Search Report dated Nov. 26, 2013.
Kloss et al. "Microcavity array (MCA)-based biosensor chip for functional drug screening of 3D tissue models," Biosensors and Bioelectronics, 2008, 23:1473-1480.
Qiu et al. "Real-Time Monitoring Primary Cardiomyocyte Adhesion Based on Electrochemical Impedance Spectroscopy and Electrical Cell-Substrate Impedance Sensing," Anal. Chem., 2008, 80, 990-996.
Xing et al. "Dynamic Monitoring of Cytotoxicity on Microelectronic Sensors," Chem. Res. Toxicol., 2005, 18(2):154-161.
Yu et al. "Real-Time Monitoring of Morphological Changes in Living Cells by Electronic Cell Sensor Arrays: An Approach to Study G Protein-Coupled Receptors," Anal. Chem., 2006, 78:35-43.
Berdondini et al. "High-density electrode array for imaging in vitro electrophysiological activity," Biosensors and Bioelectronics, 2005, 21:167-174.
Chang et al. "Impedimetric monitoring of cell attachment on interdigitated microelectrodes," Sensors and Actuators, 2005, B 105:159-163.
Yang et al. "A novel microfluidic impedance assay for monitoring endothelin-induced cardiomyocyte hypertrophy," Biosensors and Bioelectronics, 2007, 22:1688-1693.
PCT/US2009/033801 International Search Report and Written Opinion dated Jul. 9, 2010.
PCT/US2009/042787 International Search Report and Written Opinion dated Jun. 24, 2009.
PCT/US2011/036877 International Search Report dated Sep. 2, 2011.
PCT/US2013/072439 International Search Report dated Feb. 19, 2014.
Horvath et al. "Monitoring of living cell attachment and spreading using reverse symmetry waveguide sensing," Applied Physics Letters, 2005, 86:071101.
Oka et al. "A new planar multielectrode array for extracellular recording: application to hippocampal acute slic,." Journal of Neuroscience Methods, 1999, 93:61-67, Elsevier Science, B.V.
Aravanis et al. "A genetically engineered cell-based biosensor for functional classification of agents," Biosensors & Bioelectronics, 2001,16:571-577.
Becker et al. "Separation of human breast cancer cells from blood by differential dielectric affinity," Cell Biology, 1995, 92:960-964.
Bergveld, P. "A critical evaluation of direct electrical protein detection methods," Biosensors & Bioelectronics, 1991, 6:55-72.
Burns et al. "Neutrophil Transendothelial Migration is Independent of Tight Junctions and Occurs Preferentially at Tricellular Corners," Journal of Immunology, 1997, 2893-2903.
Ciambrone et al. "Cellular Dielectric Spectroscopy: A Powerful New Approach to Label-Free Cellular Analysis," J. Biomo. Screening, 2004, 9(6):467-480.
Duan et al. "Separation-Free Sandwich Enzyme Immunoassays Using Microporous Gold Electrodes and Self-Assembled Monolayer/Immobilized Capture Antibodies," Anal. Chem., 1994, 66:1369-1377.
Gutmann et al. "Evidence for Different ABC-Transporters in Caco-2 Cells Modulating Drug Uptake," Pharmaceutical Research, 1999, 16(3):402-407.

(56) References Cited

OTHER PUBLICATIONS

Lin et al. "Electroporation microchips for in vitro gene transfection," J. Micromech. Microeng., 2001,11:542-547.
Lin et al. "Simulation and experimental demonstration of the electric field assisted electroporation microchip for in vitro gene delivery enhancement," Min. for Chem., Bio., & Bioeng., 2004, 4:104-108.
Lo et al. "Impedance Analysis of MDCK cells measured by electric cell-substrate impedance sensing," Biophysical Journal, 1995, 69:2800-2807.
Mitra et al. "Electric measurements can be used to monitor the attachment and spreading of cells in tissue culture," Biotechniques, 1991, 11(4):504-510.
Miyata et al. "New Wound-Healing Model Using Cultured Corneal Endothelial Cells," Jpn. J. Opthalmol., 1990, 34:257-266.
Mohr et al. "Performance of a thin film microelectrode array for monitoring electrogenic cells in vitro," Sensors and Actuators, 1996, B34:265-269.
Nerurkar et al. "The Use of Surfactants to Enhance the Permeability of Peptides Through Caco-2 Cells by Inhibition of an Apically Polarized Efflux System." Pharmaceutical Research, 1996,13(4):528-534.
"Molecular Viewer" New Products page. Science, 298:2409 (2002).
"Cell Migration Studies with TECAN Systems." TECAN., Sep. 1999, [retrieved from the internet] http://www.tecan.com/migration_introl.pdf, 10 pgs.
Detect Cell Migration and Invasion in a Homogeneous Fluorescent Assay System. BD Biosciences, [retrieved from the internet] http://www.bdbiosciences.com/discovery_labware/Products/inserts/BD_Falcon_HTS_fluoroblok_inserts/individual_fluoroblok_inserts/index.html, 2004.
"Neuro Probe AA96, AB96, AC96 Chemotaxis Chambers." Neuro Probe, [retrieved from the internet] http://www.neuroprobe.com/protoco/pt_96a.html, 5 pgs.
"Automated Cell Monitoring Instrument." Applied BioPhysics, 2002, [retrieved from the internet] http://www.biophysics.com/pages/front.html, 1 page.
Yamauchi et al. "Spatially and temporally controlled gene transfer by electroporation into adherent cells on plasmid DNA-loaded electrodes," Nuc. Acids Res., 2004, 32(22):1-8.
Yang et al. "CelII Separation on Microfabricated Electrodes Using dielectrophoretic/Gravitational field-flow Fractionation," Anal. Chem., 1999, 71:911-918.
Connolly et al. "An extracellular microelectrode array for monitoring electrogenic cells in culture," Biosensors & Bioelectronics, 1990, 5:223-234.
Falk et al. "A 48-well Micro Chemotaxis Assembly for Rapid and Accurate Measurement of Leukocyte Migration," J. Immunol. Meth., 1980, 33:239-247.
Fuhr et al. "Positioning and Manipulation of Cells and Microparticles Using Miniaturized Electric Field Traps and Travelling Waves," Sensors and Materials, 1995, 7(2):131-146.
Hadjout et al. "Automated Real-Time Measurement of Chemotactic Cell Motility," Biotechniques, 2001, 31:1130-1138.
Huang et al. "Dielectrophoretic Cell Separation and Gene Expression Profiling on Microelectronic Chip Arrays," Anal. Chem., 2002, 74:3362-3371.
Keese et al."Real-time impedance assay to follow the invasive activities of metastatic cells in culture," Biotechniques, 2002, 33:842-850.
Larsen et al. "Somatic Cell Counting with Silicon Apertures," Micro Total Analysis Systems, 2000, 103-106.
Lo et al. "pH Changes in pulsed $CO_2$ incubators cause periodic changes in cell morphology," Experimental Cell Research, 1994, 213:391-397.
Wegener et al. "Electric cell-substrate impedance sensing system (ECIS) as a noninvasive means to monitor the kinetics of cell spreading to artificial surfaces," Eur. J. Physiol., 1999, 437:925-934.
PCT/US2005/034561 International Preliminary Report on Patentability dated Mar. 27, 2007.

PCT/US2005/034561 International Search Report dated Sep. 27, 2006.
PCT/US2005/027943 International Preliminary Report on Patentability dated Apr. 11, 2007.
PCT/US2005/027943 International Search Report and Written Opinion dated Mar. 21, 2007.
PCT/US2004/037696 International Search Report dated May 16, 2005.
PCT/US2005/04481 International Search Report dated Sep. 12, 2005.
EP05722991 Extended European Search Report dated Apr. 3, 2009.
EP11193882 Extended European Search Report dated Apr. 5, 2012.
EP13171137 Extended European Search Report dated Aug. 16, 2013.
EP05786773 Extended European Search Report dated Mar. 21, 2013.
EP05852157 Extended European Search Report dated Sep. 13, 2011.
EP058122680 Extended European Search Report dated Sep. 7, 2011.
EP03748948 Extended European Search Report dated Mar. 12, 2007.
CA2556219 Office Action dated Aug. 9, 2010.
CA2575573 Office Action dated Apr. 4, 2012.
Blagbrough et al. "Polyamines and novel polyamine conjugates interact with DNA in ways that can be exploited in non-viral gene therapy," Biochemical Society Transactions, 2003, 31, Part 2, 397-406.
Bonetta, Laura. "The inside scoop-evaluating gene delivery methods," Nature Methods, Nov. 2005, 2(11):875-883.
Hapala, Ivan. "Breaking the Barrier: Methods for Reversible Permeabilization of Cellular Membranes," Critical Reviews in Biotechnology, 1997, 17(2):105-122.
Loffert et al. "Multiplex PCR with QIAGEN: Taq DNA Plymerase and PCR Buffer," QIAGENews, 1994, 4:15-18.
Luan et al. "Clustering of time-course gene expression data using a mixed-effects model with B-splines," Bioinformatics, 2003, 19(4):474-482.
Nicolazzi et al. "Cationic Lipids for Transfection," Current Medicinal Chemistry, 2003, 10:1263-1277.
Rabow et al. "Mining the National Cancer Institutes Tumor-Screening Database: Identification of Compounds with Similar Cellular Activities," J. Met Chem., 2002, 45:818-840.
Steinem et al. "Impedance and shear wave resonance analysis of ligand-receptor interactions at functionalized surfaces and of cell monolayers," Biosensors & Bioelectronics, 1997, 12(8):787-808.
Patolsky et al. "Detection of single-base DNA mutations by enzyme-amplified electronic transduction," Nature Biotechnology, 2001, 19:253-257.
Pethig et al., "Positive and negative dielectrophoretic collection of colloidal particles using interdigitated castellated microelectrodes," Appl. Phys., 1992, 24:881-888.
Richards et al. "A Modified Microchamber Method for Chemotaxis and Chemokinesis," Immunological Communications, 1984,13(1):49-62.
Rishpon et al. "An Amperometric Enzyme-channeling lmmunosensor," Biosensors & Bioelectronicsd, 1997, 12(3):195-204.
Simpson et al. "Whole-cell biocomputing," Trends in Biotechnology, 2001, 19(9):317-323.
Sohn et al. "Capacitance cytometry: Measuring biological cells one by one," Proc. Nat. Acad. Sci., 2000, 97(20):10687-10690.
Svetlicic et al. "Charge Displacement by adhesion and spreading of a cell," Bioelectrochemistry, 2000, 53:79-86.
Tiruppathi et al. "Electrical method for detection of endothelial cell shape change in time: assessment of endothelial barrier function," Proc Natl Acad Sci USA , 1992, 89:7919-7923.
Wang et al. "Selective Dielectrophoretic confinement of bioparticles in potential energy wells," Appl. Phys., 1993, 26:1278-1285.
Wang et al. "Cell Separation by Dielectrophoretic Field-flow-fractionation," Anal. Chem., 2000, 72:832-839.
Wang et al. "Dielectrophoretic Manipulation of Cells with Spiral Electrodes," Biophysical Journal, 1997, 72:1887-1899.

(56) References Cited

OTHER PUBLICATIONS

Wang et al. "Separation of Polystyrene Microbeads Using Dielectrophoretic/Gravitational Field-Flow-Fractionation," Biophysical Journal, 1998, 74:2689-2701.

Wang et al. "Electronic Manipulation of Cells on Microchip-Based Devices," Biochip Technology, 2001,135-159, Harwood Academic Publishers, PA, USA.

Warburg, E. "Ueber die Polarisationscapacitaet des Platins," Ann Phys, 1901, 6:125-135.

Klauke et al. "Extracellular Recordings of Field Potentials from Single Cardiomyocytes," Biophysical Journal, Oct. 2006, 91(7)2543-2551.

Lo et al. "Abstract C1.00268: Effect of cMet Inhibitor on HGF-Induced Ovarian Carcinoma Cell Migration," American Physical Societal March Meeting, 2010, Portland Oregon, vol. 55, No. 2 poster session.

Banach et al. "Development of electrical activity in cardiac myocyte aggregates derived from mouse embryonic stem cells," Am. J. Physiol. Heart Circ. Physiol., 2003, 284:H2114-H2123.

Hescheler et al. "Determination of electrical properties of ES cell-derived cardiomyocytes using MEAs," Journal of Electrocardiology, 37:110-116.

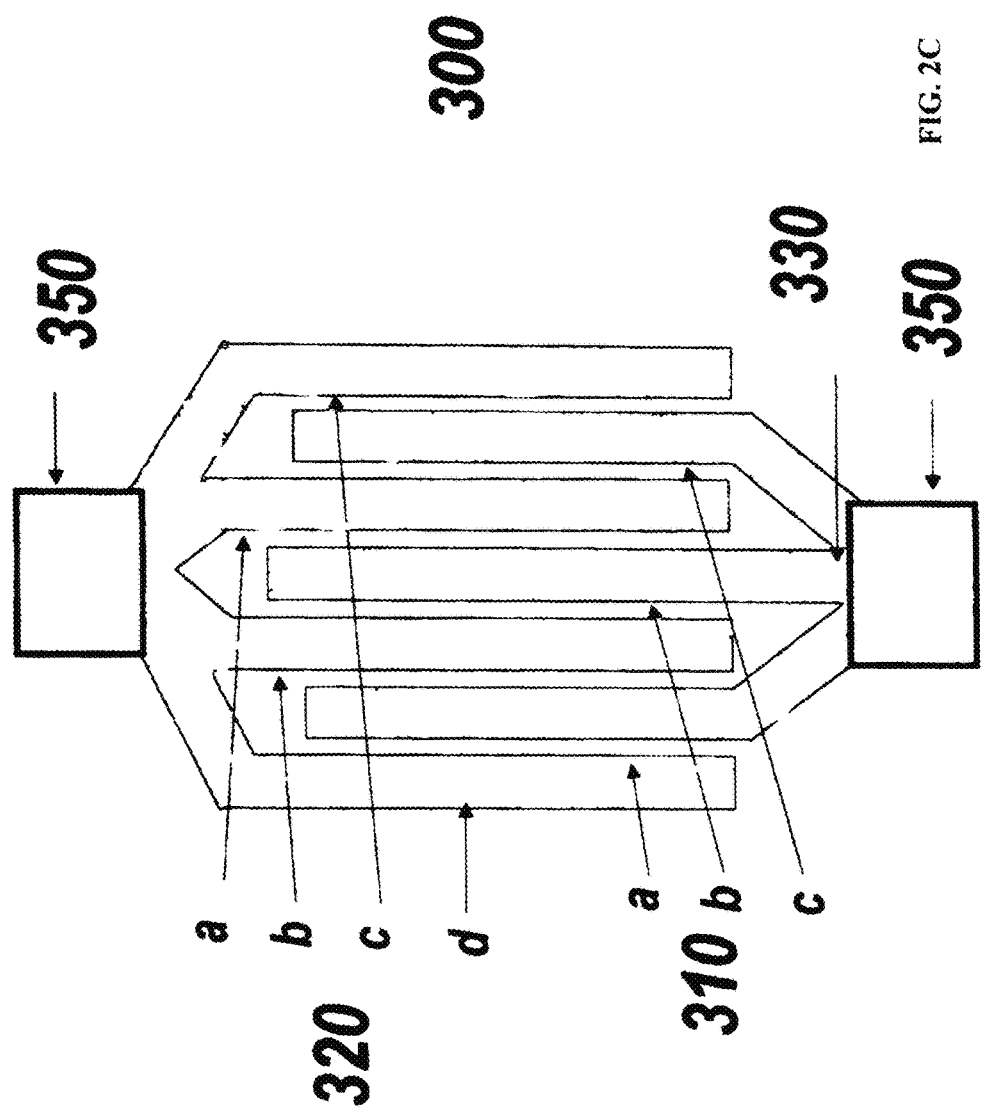

Titration of ES-derived cardiomyocytes using the ACEA RT-CES system

Treatment of ES-derived cardiomyocytes with a cytotoxic compound of Sodium dichromate dehydrate.

Detection of morphological changes associated with ES-derived cardiomyocytes induced by isoproteranol, a β2 adrenergic receptor agonist, using the RT-CES system Detection of cardiomyocyte beating using the ACEA RT-CES system at different time periods along the growth and differentiative curve of ES-derived cardiomyocytes seeded in ACEA E-Plates. The time resolution between adjacent points in Figures 7A, 7B and 7C is about 40 milliseconds. In other words, a second shown in Figures 7A, 7B and 7C is equivalent to 40 milliseconds.

Detection of cardiomyocyte beating using the ACEA RT-CES system for the mouse cardiomyocytes treated with 4.4 uM sotalol. In Figures 9C and 9D, the time resolution between two adjacent points is 40 milliseconds. In other words, a second in Figures 9C and 9D is equivalent to 40-millisecond.

Analysis of drugs which increase heart rate and cardiomyocyte beating

Sotalol 33.3 uM (0.033% DMSO)

Astemizole 400 nM (0.004% DMSO)

Terfenadine 200 nM (0.065%DMSO)

Erythromycin 13.3 uM (0.13% DMSO)

Moxifloxacin 20 uM (0.3% DMSO)

Pentamidine 20uM (0.2%DMSO)

Amitriptyline 4.4uM(0.04 % DMSO)

Verapamil 130 nM (0.0013% DMSO)

Rosiglitazone 13.3 uM (0.13% DMSO)

Rofecoxib 13.3 uM

Celecoxib 4.4 uM

Doxirubicin 40 uM (0.4% DMSO)
(measurement after 2h treatment)

Cyclosporine A 13.3uM (0.13% DMSO)

Propranolol 4.4uM (0.04% DMSO)

E4031 9.1 nM

DDT 8uM (0.08% DMSO)

PCB 8uM (DMSO 0.08%)

Endosulfan 8uM (0.08% DMSO)

DMSO 0.13%

Cardiotoxic Patterns

LABEL-FREE MONITORING OF EXCITATION-CONTRACTION COUPLING AND EXCITABLE CELLS USING IMPEDANCE BASED SYSTEMS WITH MILLISECOND TIME RESOLUTION

CROSS-REFERENCE TO RELATED APPLICATIONS

This application is a continuation of U.S. patent application Ser. No. 12/435,569, filed May 5, 2009, which claims benefit of priority to U.S. provisional patent application Ser. No. 61/191,684, filed on Sep. 11, 2008, and U.S. provisional patent application Ser. No. 61/126,533, filed on May 5, 2008, the content of each is herein incorporated by reference in their entirety.

FIELD OF THE INVENTION

The present invention relates generally to impedance based monitoring of cells and more particularly to systems and methods for monitoring excitation-contraction coupling and excitable cells using impedance based systems with millisecond time resolution.

BACKGROUND OF THE INVENTION

Excitation-contraction coupling (ECC) is a term used to describe the physiological process of converting an electrical stimulus to a mechanical response. The process is fundamental to muscle physiology, wherein the electrical stimulus may be an action potential and the mechanical response is contraction. Although ECC has been known generally over half a century, it is still an active area of biomedical research.

Cardiomyocytes are specialized muscle cells of the myocardium that are capable of excitation-contraction coupling. Cardiomyocytes are commonly used in biomedical research to assess the cardiotoxicity of potential drugs or treatments. Two conventional approaches to assess cardiotoxicity are primarily used. A first approach involves isolation of cardiomyocytes directly from a mammalian species such as rats and dogs followed by electrophysiological studies on the isolated cardiomyocytes. However, this approach suffers from being extremely labor-intensive, time consuming and costly and at the same time not very amenable to the high throughput demands of pharmaceutical industry. An alternative approach utilizes cell-based assay models, which heterologously express specific ion channels such as hERG channels or voltage-gated calcium channels. These cardiac ion channels have been envisioned as possible molecular targets through which drugs could induce cytotoxicity. These cell-based systems allow assessment of drug-channel interaction by monitoring the effect of the drug on currents produced by different channels in cultured cells using a technique known as "patch clamping." Patch clamping isolates regions of the cell membrane containing channel proteins and measures changes in electrical potential difference. However, use of this method in high throughput requires automation of patch clamping in an array format, which even though is becoming increasing available, is not yet widespread. In addition, cardiac toxicity may occur by other mechanisms that may be missed by this type of targeted approach.

An alternative to in vitro ion-channel recording assays as well as the labor-intensive isolation of primary tissue is the differentiation of embryonic stem (ES) cells into cardiomyocytes. The utility of ES cells as a treatment for various chronic diseases has received much attention in recent years. Mammalian ES cells are self renewing cells derived from the inner cell mass of a blastocyst stage embryo which can be differentiated into multiple different cell types. It has been demonstrated that the mouse ES cells as well as human ES cells can be differentiated into cardiomyocytes which retain the ability to beat in culture. Differentiation of ES cells first involves an intermediate in vitro developmental stage in which ES cells form compact cell structures known as embryoid bodies. These embryoid bodies can induce the developmental program of ES cell differentiation into multiple cell types including cardiomyocytes, which are distinguished in culture by their ability to undergo spontaneous beating. These ES derived in vitro differentiated cardiomyocytes recapitulates the normal development of cardiomyocytes as evidenced by the stage-specific expression of cardiomyocyte specific genes. All the known transcription factors, ion channels and structural proteins that are part of normal heart development and function in vivo are also expressed in ES-derived cardiomyocytes.

Even though high throughput to medium throughput systems have been developed for functional characterization of cell lines heterologously expressing the gene for specific ion channels, high throughput techniques for functional characterization of more complex systems such as cardiomyocytes have been limited. Technologies designed to assess cardiomyocyte behaviour and function and the effect of drugs and other manipulations in vitro can be divided into two different approaches. One approach involves long term assessment of cardiomyocyte viability for example in response to certain compounds. Such assays are typically end point assays designed to measure a cellular component such as ATP which correlates with the degree of viability of the cells. The other approach involves studying short term effect of drugs and compounds on beating function of cardiomyocytes. High throughput techniques for short term functional characterization of ion channels and other targets in cardiomyocytes has been rather challenging and limited. The available systems typically only monitor a single cardiomyocyte or a small number of cardiomyocytes at a time and with very limited throughput.

SUMMARY OF THE INVENTION

The present invention addresses the need to provide systems and methods for improved monitoring of excitation-contraction coupling and excitable cells and provides related benefits. Specifically, embodiments of the invention describe label-free methods for monitoring excitable cells, such as cardiomyocytes, in vitro. The system is capable of continuously monitoring excitation-contraction coupling in a relatively high-throughput manner. The systems and methods can be used for pharmacological safety assessment, screening for novel compounds which modulate cardiomyocyte function in a specific manner, and assessment of genes involved or potentially involved in cardiac function. In addition the system and methods may study the role of different genes and proteins in cardiac function and development through the use of embryonic stem (ES) derived cardiomyocytes.

In one aspect of the presence invention a system for monitoring impedance of excitable cells in vitro is provided including a device for monitoring cell-substrate impedance, an impedance analyzer capable of impedance measurements at millisecond time resolution, electronic circuitry that can engage the device and selectively connect two or more electrode arrays of the device to the impedance analyzer and a software program that controls the electronic circuitry and records and analyzes data obtained from the impedance analyzer. Embodiments of the device for monitoring substrate impedance include a nonconductive substrate having one or more individually addressable electrode arrays fabricated thereon and one or more wells. Preferably, each of the one or more arrays is associated with one of the one or more wells and each electrode array is individually addressable. In further embodiments, a surface of the substrate is suitable for cell attachment, wherein cell attachment results in a detectable change in impedance between electrodes within the array. Attachment or growth along the surface may be enhanced by applying a precoat having one or more compounds that improve attachment. In embodiments where the device includes multiple wells, the impedance analyzer has the capability to allow impedance measurements for each and every well at millisecond time resolution. That is to say, for a selected time period, the impedance data for each and every well of the system is measured at millisecond time resolution. Further, when groups of wells are monitored, the groups are monitored at millisecond time resolution.

Embodiments of the system include electrode arrays having two electrode structures that have substantially the same surface area. The electrodes themselves may be formed from suitable electrically conductive materials such as metal, gold, platinum, titanium, chromium and the like. The electrode arrays may be organized in a variety of configurations, including interdigitated, circle-on-line, diamond-on-line, concentric, sinusoidal, and castellated. The widths of the electrode structures may be between 20 microns and 500 microns or 5 microns and 100 microns.

Embodiments of the invention include impedance monitoring using millisecond time resolution. Millisecond time resolution allows monitoring of at least two consecutive impedance measurements with an excitation cycle of excitable cells, which are introduced into the well. Further, millisecond time resolution enhances measurement such that excitation-contraction coupling of excitable cells may be effectively monitored. In some embodiments the excitation cycle is a beating cycle, such as a beating cycle of a cardiomyocyte. In some embodiments at least two consecutive impedance measurements are performed in less than 100 milliseconds. In other embodiments at least two consecutive impedance measurements are performed in less than 40 milliseconds. In still further embodiments at least two consecutive impedance measurements are performed in less than 20 milliseconds. In still further embodiments the at least two consecutive impedance measurements are performed in less 10 milliseconds.

In some embodiments the device is provided as a multiwell device or a multiwell plate. In some embodiments, the multiwell device or multiwell plate may including 6 wells, 8 wells, 16 wells, 32 wells, 96 wells, 384 wells or any number therebetween. Throughout the present application where the device includes multiple wells each of which is associated with an electrode array, millisecond time resolution refers to that for any selected time period, the impedance measurement for each and every well can be performed with two consecutive measurements separated with millisecond resolution. Further, when groups of wells, such as subsets of all wells of a device, are monitored a group of wells may be monitored using millisecond time resolution.

Embodiments of the present invention provide impedance-based monitoring with millisecond time resolution in combination with longer term monitoring of cells. By combining millisecond time resolution technology with impedance monitoring having longer time periods, both short term and long term effects on excitable cells can be evaluated. In some embodiments impedance readouts can be used to monitor both short term beating and long term viability status of cardiomyocytes in the same well or the same population. Such monitoring addresses needs where certain manipulations such as drug treatment may not manifest its effect on cardiomyocyte beating and/or viability until a later time period.

In some embodiments methods for assessing and quantifying excitable cells in vitro include providing the impedance-based system with millisecond time resolution; adding excitable cells to one or more wells; monitoring impedance of the one or more wells over a first time period, which is characterized as a longer time period, such as seconds, minutes, hours or days; monitoring impedance of the one or more wells over a second time period in millisecond time resolution; determining a characteristic, such as cell attachment, cell growth and cell viability from monitoring over the first time period; and resolving individual cycles of the excitable cells from monitoring over the second time period. In such embodiments, monitoring impedance over the second time period may be performed at regular or irregular time intervals within monitoring impedance over the first time period.

Among the benefits, embodiments of the invention permit impedance readouts to monitor the morphological or differentiative behavior of cardiomyocytes in vitro. Certain treatments can induce changes in morphological behavior of cardiomyocytes, such as inducing hypertrophy which is associated with cardiomyocyte elongation and expansion. Because impedance monitoring can detect changes in cell morphology, it can be used to for detection of hypertrophy in cardiomyocytes.

In another aspect of the present invention a method for assessing or quantifying excitable cells in vitro is provided. An exemplary method includes providing the impedance based system having millisecond time resolution, adding excitable cells to the one or more wells, monitoring impedance of the one or more wells, and resolving individual cycles of the excitable cells. The method has particular utility with cells that are known or suspected to be capable of or undergo excitation-contraction coupling, such as cardiomyocytes. The method may also be useful for monitoring neurological cells or neurological systems. Impedance measurements may be performed in millisecond time resolution. In some embodiments, two consecutive impedance measurements for each and every well of the system are performed less than 300 milliseconds apart. In further embodiments, at least two consecutive impedance measurements for each and every well of the system are performed less than 100 milliseconds apart. In further embodiments, at least two consecutive impedance measurements for each and every well of the system are performed less than 40 milliseconds apart. In further embodiments, at least two consecutive impedance measurements for each and every well of the system are less than 10 milliseconds apart.

In some embodiments methods of determining whether a compound modulates a beating cycle of an excitable cell is provided. An exemplary method includes providing the impedance based system having millisecond time resolution, wherein the system includes at least two wells; adding excitable cells to the at least two wells; monitoring impedance of the at least two wells; adding a compound suspected of modulation of the beating cycle to a first of the at least two wells to provide a test well, wherein a second well lacking compound or having a control compound is provided as a control well; resolving the beating cycle of both test well and control well; and comparing the beating cycles between the test well and control well, wherein a difference in beating cycles indicates the compound modulates the beating cycle of the excitable cell. In some embodiments, beating cycles are compared to identify changes in beating magnitude or amplitude. In other embodiments, beating cycles are compared to identify changes in beating frequency, which may be regular changes or irregular changes. In further embodiments the method includes determining a cell index for each of the test well and control well such that the step of comparing the beating cycles includes comparing the cell indices between test well and control well. Peak magnitude or amplitude and/or frequency may be compared. The method may also include monitoring impedance over longer time periods of time. Such embodiments may provide long term impedance monitoring with intermittent monitoring using millisecond resolution. Thus short term and long term monitoring may be performed.

In another exemplary methods include providing a device for measuring cell-substrate impedance operably connected to an impedance analyzer, wherein the device includes at least two wells; adding ES cells, adult stem-cell derived cardiomyocytes or primary cardiomyocytes to at least two wells; monitoring impedance of the at least two wells at different or similar time intervals over a period of time and optionally determining cell indices from impedance values; generating an impedance-based curve or optionally a cell index curve for each of the at least one known biologically active agent and the control; comparing the impedance-based curves or optionally the cell index curves between the at least one known biologically active agent well and the control well. The impedance-based curves may be direct measurement of cardiomyocyte excitation-contraction coupling and if significantly different, concluding that the biologically active agent modulates cardiomyocyte function. Optionally, impedance-based curves or optionally cell index curves are used to calculate average rate of beats of cardiomyocytes per unit time, average amplitude intensity in a unit time as well as the average length of time between the beats, comparison of these optionally derived parameters is made between the at least one known biologically active agent well and the control well, and if significant differences exist, one may optionally conclude that the biologically active agents modulate cardiomyocyte functions.

In other embodiments of the present invention, a method of characterizing rhythmic beating of a cardiomyocyte is provided. An exemplary method includes providing the impedance based system with millisecond time resolution; adding excitable cells to the one or more wells; monitoring impedance of the one or more wells in millisecond time resolution; determining a plurality of beating cycle peaks; and comparing magnitude or amplitude or frequency of the peaks over a time unit. Various methods can be used for determining beating cycle peaks. For example, time dependent impedance values or cell index values for a well are analyzed by deriving their first order derivatives and second order derivatives using numerical methods. The beating cycle peaks are those data points where the first order derivatives of impedance values or cell index values are zero or close to zero in its absolute value. If the beating cycle peak is a positive peak (i.e. peak corresponds to a maximum value in measured impedance or cell index over the beating cycle), then the peak would correspond to the data points where the second order derivatives of the impedance values or cell index values is negative and where the first order derivatives of the impedance values or cell index values is zero or close to zero in its absolute value. If the beating cycle peak is a negative peak (i.e. peak corresponds to a minimum value in measured impedance or cell index over the beating cycle), then the peak would correspond to the data points where the second order derivatives of the impedance values or cell index values is positive and where the first order derivatives of the impedance values or cell index values is zero or close to zero in its absolute value. The step of determining a plurality of beating cycle peaks may include determining a rise in impedance and a decay in impedance and extrapolating a peak from each rise and decay. The method may further include determining a cell index for each of the one or more wells, which may allow improved comparison of beating cycles. Further, beating cycle peaks may be determined by identifying frequency components having largest magnitude in Fourier transformed impedance data. The method may also include monitoring impedance over longer time periods of time. Such embodiments may provide long term impedance monitoring with intermittent monitoring using millisecond resolution.

A variety of agents and compounds may be tested for modulation of excitable cells and for modulation of rhythmic beating of cardiomyocytes. Examples include compounds, peptides, proteins, antibodies or antibody fragments, siRNA, shRNA, lipid or any combination of thereof.

In another aspect of the present invention a method of assessing genetic manipulation of an embryonic stem cell is provided including providing the impedance based system having millisecond time resolution, mutating embryonic stem cells to include a genetic mutation; adding mutated embryonic stem cells to a first well of at least two wells to form a test well and control embryonic stem cells to a second of at least two wells to form a control well; monitoring impedance of the at least two wells in millisecond time resolution; resolving the beating cycles of both test well and control well, if any; and comparing the beating cycles between the test well and control well, wherein a difference in beating cycles indicates the genetic mutation modulates embryonic stem cell differentiation. In some embodiments the embryonic stem cell differentiation is differentiation into a cardiomyocyte. In some embodiments the genetic mutation is selected from the group consisting of a genetic knock out, a knock down and an inserted transgene. The method may also include monitoring impedance over longer time periods of time. Such embodiments may provide long term impedance monitoring with intermittent monitoring using millisecond resolution. Thus short term and long term monitoring may be performed.

BRIEF DESCRIPTION OF THE DRAWINGS

Those skilled in the art will recognize that the drawings described below are for illustrative purposes only. The drawings are not intended to limit the scope of the invention but to provide exemplary embodiments.

FIG. 1A shows a nonconductive substrate (101) shown with 16 electrode arrays fabricated on the substrate. Each electrode array (102) comprises two electrode structures (shown in detail in FIG. 1B). Each electrode structure comprises multiple electrode elements. Each electrode array connects to two electrical traces (103), with each of the two traces connected one of the two electrode structures. These electrical connection traces (103) from the electrode array (102) are connected to the connection pads (104) at the edges of the substrate (101). As shown in FIG. 1A, each the four electrode arrays in each of four quarters on the substrate (101) have one of their electrical connection traces (103) connected to a common connection pad (104). Thus, for the entire device there are four common connection pads (104), one for each quarter of the device. In addition, each electrode array has a separate electrical connection trace (103), connecting to an independent connection pad (104). Thus, there are total 20 connection pads (104) at the edges of the substrate (101). In FIG. 1B a single exemplary electrode array is shown. The electrode array has two electrode structures, where each electrode structure comprises multiple electrode elements (105) shown here having a circle-on-line geometry. In this electrode array structure, electrode elements (105) of one electrode structure of the array alternate with electrode elements (105) of the other electrode structure of the array. Each of the electrode structures is independently connected to its electrode bus (106), in this case, by means of direct connection of the electrode elements (105) to the electrode bus (106). Each electrode bus (106) forms an arc around the perimeter of the array, where the two buses of the array do not abut or overlap. The electrically conductive connection traces (103 in FIG. 1A) connect each bus with a connection pad (104 in FIG. 1A) on the edge of the substrate (101 in FIG. 1A).

FIG. 2C is a schematic representation of a device 300 with two electrode structures of similar areas deposited on a substrate. Electrode structures 310 and 320 comprise multiple interconnected electrode elements (310a-310f, 320a-320f). Electrode elements (310a-310c, 320a-320d) are rectangular lines and together form an interdigitated electrode structure unit. Different from FIG. 2A and FIG. 2B, the electrode structures having electrode elements 310a-310c and 320a-320c are connected to connection pads 350.

In FIGS. 9C and 9D, the time resolution between two adjacent points is 40 milliseconds. In other words, a second in FIGS. 7C and 7D is equivalent to 40 milliseconds.

DETAILED DESCRIPTION OF THE INVENTION

Figure 1A:
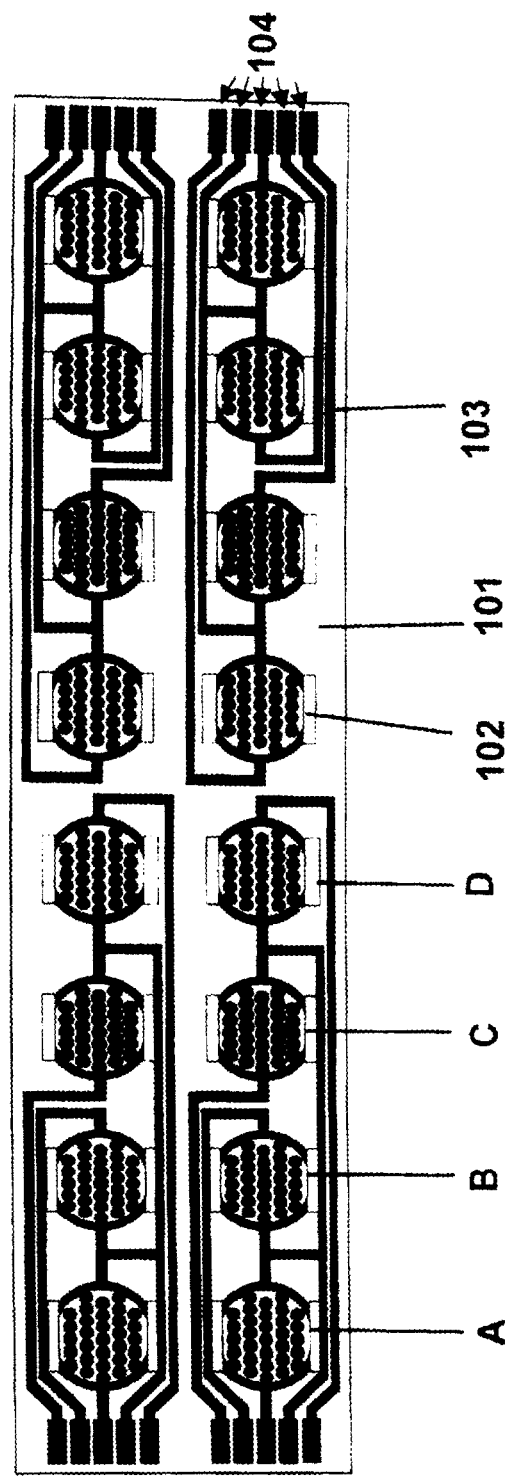
FIGS. 1A-1B depict schematic drawings of one design of a cell-substrate impedance measurement device of the present invention.
Figure 1B:
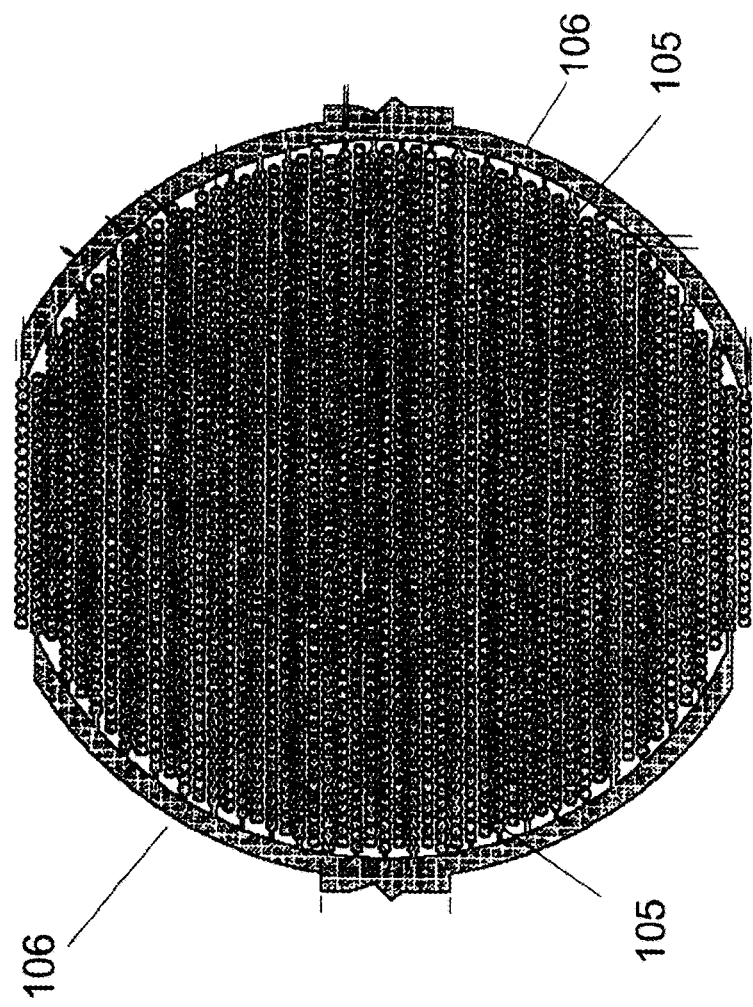
Figure 2A:
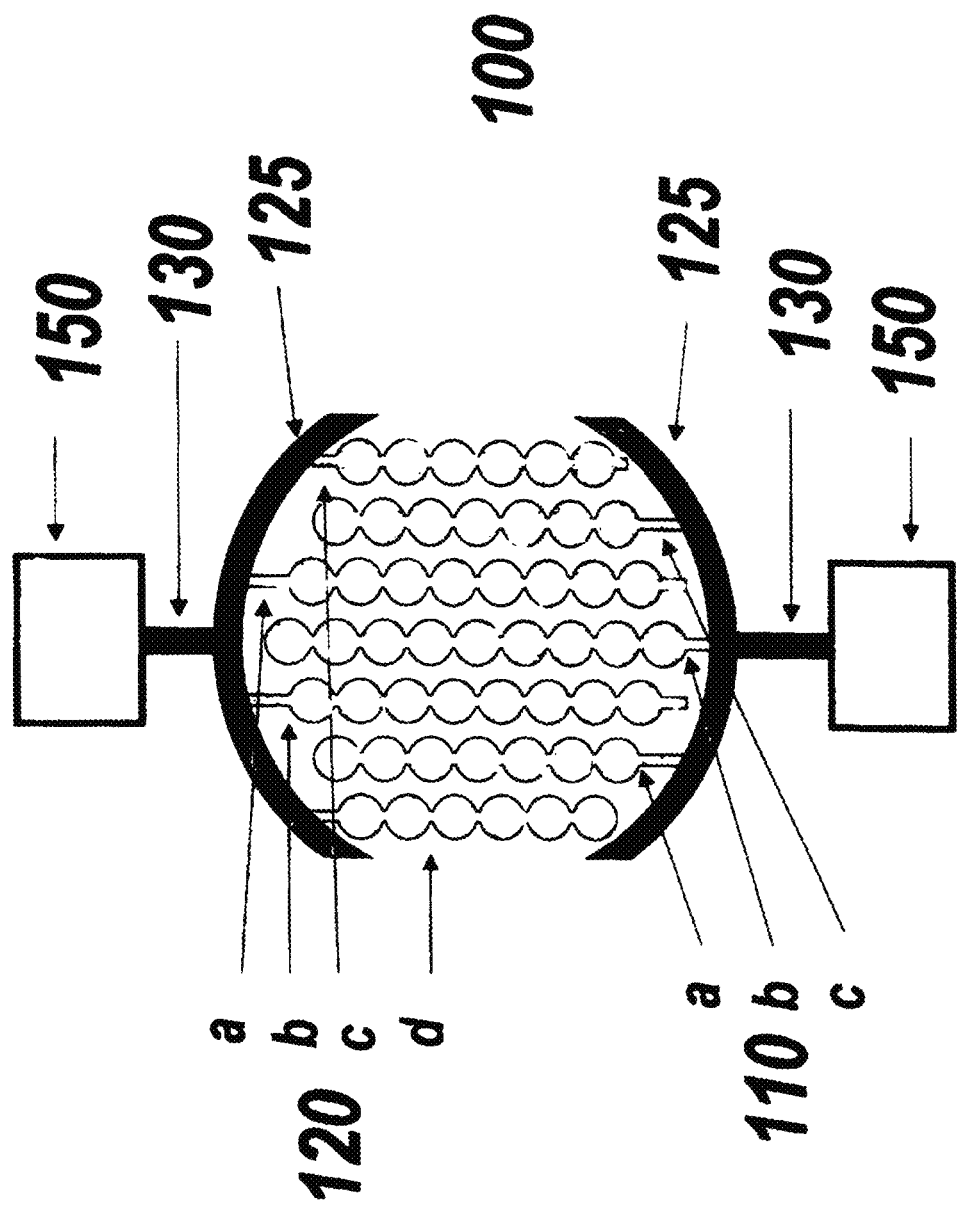
FIG. 2A is a schematic representation of a device 100 with two electrode structures of same or similar areas deposited on a substrate. First electrode structure has electrode elements 110a, 110b, 110c and second electrode structure has electrode elements 120a, 120b, 120c and 120d. Electrode elements within an electrode structure are connected to each other by arc-shaped connection electrode bus 125. Like the electrode elements, such connection-buses (125) are also made of electrically-conductive material (e.g. gold film, platinum film, gold film over a chromium or titanium film). These electrically-conductive connection-paths or connection buses (125) may have an insulating coating. Electrode elements 110a-110c and 120a-120d comprise electrode lines with connected circles added on the line. The overall area of electrode elements and gaps between electrode elements may correspond to, or may be slightly larger than, or may be slightly smaller than, the bottom of a well (e.g., a cylinder shaped well, a conical shaped well, or a cubic shaped well), for example, a 24 well-plate, a 96-well plate, or 384 well plate that are commonly used. The whole surfaces of the wells may be covered with electrodes to ensure that the cell attachment at nearly any locations of the bottom surface of the well can contribute to the impedance change. This arrangement has an advantage that non-uniform landing and attachment of cells on the bottom surface of the different wells would result in only a small variation in the impedance measured between electrode structures 110 and 120. 150 are connection pads that can be connected to an external impedance measurement circuit. 130 is the electrical connection traces that connects the connection pad to the electrode structures 110 and 120. Such connection traces can extend in any direction in the plane of the electrodes.
Figure 2B:
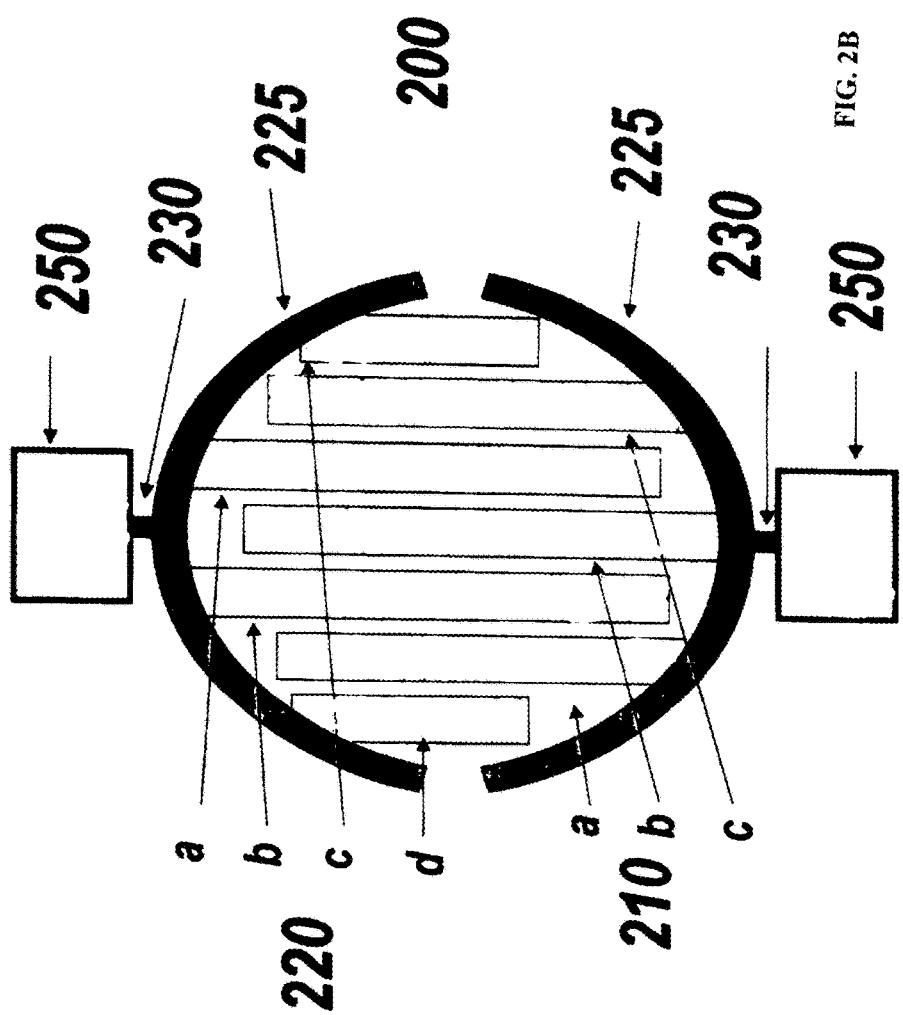
FIG. 2B is a schematic representation of a device 200 with two electrode structures of similar areas deposited on a substrate. Electrode structures 210 and 220 comprise multiple interconnected electrode elements. Electrode elements (210a-210c, 220a-220d) are rectangular lines and together form an interdigitated electrode structure unit. Similar to FIG. 2A, the electrode elements (210a-210c, 220a-220d) within each electrode structure are connected through arc-shaped, electrically conductive paths or electrode buses (225). Connection pads 250 are connected to electrode structures through the electrical connection traces 230.

Detailed descriptions of preferred embodiments of the provided herein. It is to be understood; however, that the present invention may be embodied in various forms. Therefore specific reference to various forms are provided as a basis for the claims and for teaching one skilled in the present art to employ the present invention in appropriate system, structure or manner.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "membrane" is a sheet of material.

As used herein, "biocompatible polymer" means a polymeric material that does not have deleterious effects on cells, including the viability, attachment, spreading, motility, growth, or cell division.

As used herein, "suitable for attachment" refers to structural features that permit attachment of cells thereto. A surface is "suitable for cell attachment" when a significant percentage of the cells attach or adhere to the surface within twelve hours. Preferably, at least 50% of the cells are adhered to the surface within twelve hours. More preferably, at least 70% of the cells are adhered to the surface within twelve hours of plating (i.e., adding cells to the well or fluid container). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating. To have desired surface properties for cell attachment, the surface may need to chemically-treated (e.g. treatment with an acid and/or with a base), and/or physically treated (e.g. treatment with plasma), and/or biochemically treated (e.g. coated with one or more molecules or biomolecules that promotes cell attachment).

As used herein, "impedance measurement at millisecond time resolution" refers to the ability to perform a series of at least two consecutive impedance measurements within milliseconds of one another for each and every well of the system where each well is associated with an electrode array for impedance measurement. In each instance the time between two consecutive impedance measurements are less than 300 milliseconds from one another. Preferably, consecutive impedance measurements are less than 200 milliseconds from one another. More preferably impedance measurements are less than 100 milliseconds from one another. For example, the time between two consecutive impedance measurements are 40 milliseconds from one another for each and every well of the system. To be clear, that is to say, in a time period of 40 milliseconds, the system has the ability to measure two impedance data points for each and every well of the system.

As used herein, "excitable cells" refers to a cell population that is capable of propagation and spreading action potentials to surrounding cells. These cells are able to produce and respond to electrical signals. Some excitable cells are capable of excitation-contraction coupling. Examples of "excitable cells" include cardiomyocytes, cells that beat, some skeletal muscle cells, some smooth muscle cells and some neural cells. Identification of excitable cells may be found in cell biology literature.

As used herein, "excitation-contraction coupling" refers to the physiological process of converting an electrical stimulus to mechanical response. This process is fundamental to muscle physiology, whereby the electrical stimulus is usually an action potential and the mechanical response is contraction. EC coupling can be dysregulated in many disease conditions.

As used herein, "beating cycle" refers the time between which a cardiomyocyte sequentially beats. The "beating cycle" may vary depending on organism and developmental stage of the cardiomyocyte. A beating cycle may be as short as between 100 and 200 milliseconds, translating to a beating rate of 600 to 300 beats per minute. A beating cycle may be as long as between 1000 milliseconds and 10,000 milliseconds, translating to a beating rate of 60 to 6 beats per minute.

As used herein, "biomolecular coating" or "coated with a biomolecule" refers to is a coating on a surface that comprises a molecule that is a naturally occurring biomolecule or biochemical, or a biochemical derived from or based on one or more naturally occurring biomolecules or biochemicals. For example, a biomolecular coating can comprise an extracellular matrix component (e.g., fibronectin, collagens), or a derivative thereof, or can comprise a biochemical such as polylysine or polyornithine, which are polymeric molecules based on the naturally occurring biochemicals lysine and ornithine. Polymeric molecules based on naturally occurring biochemicals such as amino acids can use isomers or enantiomers of the naturally-occurring biochemicals.

As used herein, "extracellular matrix component" refers to a molecule that occurs in the extracellular matrix of an animal. It can be a component of an extracellular matrix from any species and from any tissue type. Nonlimiting examples of extracellular matrix components include laminins, collagens fibronectins, other glycoproteins, peptides, glycosaminoglycans, proteoglycans, etc. Extracellular matrix components can also include growth factors.

As used herein, "electrode" refers to a structure having a high electrical conductivity, that is, an electrical conductivity much higher than the electrical conductivity of the surrounding materials.

As used herein "electrode structure" refers to a single electrode, particularly one with a complex structure (as, for example, a spiral electrode structure), or a collection of at least two electrode elements that are electrically connected together. All the electrode elements within an "electrode structure" are electrically connected.

As used herein, "electrode element" refers to a single structural feature of an electrode structure, such as, for example, a fingerlike or branched projection of an interdigitated electrode structure.

As used herein "electrode structure unit" refers to two or more electrode structures that are constructed to have dimensions and spacing such that they can, when connected to a signal source, operate as a unit to generate an electrical field in the region of spaces around the electrode structures. Preferred electrode structure units of the present invention can measure impedance changes due to cell attachment to an electrode surface. Non-limiting examples of electrode structure units are interdigitated electrode structure units and concentric electrode structure units.

As used herein, "electrode traces" refer to electrically conductive paths that extend from electrodes or electrode elements or electrode structures toward one end or boundary of a device or apparatus for connecting the electrodes or electrode elements or electrode structures to an impedance analyzer. The end or boundary of a device may correspond to the connection pads on the device or apparatus.

As used herein, "connection pad" refers to an area on an apparatus or a device of the present invention which is electrically connected to at least one electrode or all electrode elements within at least one electrode structure on an apparatus or a device and which can be operatively connected to external electrical circuits (e.g., an impedance measurement circuit or a signal source). The electrical connection between a connection pad and an impedance measurement circuit or a signal source can be direct or indirect, through any appropriate electrical conduction means such as leads or wires. Such electrical conduction means may also go through electrode or electrical conduction paths located on other regions of the apparatus or device.

As used herein, "interdigitated" refers to having projections coming from one direction that interlace with projections coming from a different direction in the manner of the fingers of folded hands (with the caveat that interdigitated electrode elements preferably do not contact one another).

As used herein, "high probability of contacting an electrode element" refers to if a cell is randomly positioned within the sensor area of a device or apparatus of the present invention, the probability of a cell (or particle) contacting on an electrode element, calculated from the average diameter of a cell used on or in a device or apparatus of the present invention, the sizes of the electrode elements, and the size of the gaps between electrode elements, is greater than about 50%, more preferably greater than about 60%, yet more preferably greater than about 70%, and even more preferably greater than about 80%, greater than about 90%, or greater than about 95%.

As used herein, "at least two electrodes fabricated on said substrate" refers to at least two electrodes are fabricated or made or produced on the substrate. The at least two electrodes can be on the same side of the substrate or on the different side of the substrate. The substrate may have multiple layers, the at least two electrodes can be either on the same or on the different layers of the substrate.

As used herein, "at least two electrodes fabricated to a same side of said substrate" refers to at least two electrodes are fabricated on the same side of the substrate.

As used herein, "at least two electrodes fabricated to a same plane of said substrate" refers to, if the nonconducting substrate has multiple layers, the at least two electrodes are fabricated to the same layer of the substrate.

As used herein, "electrodes have substantially same surface area" refers to the surface areas of the electrodes referred to are not substantially different from each other, so that the impedance change due to cell attachment or growth on any one of the electrodes referred to will contribute to the overall detectable change in impedance to a same or similar degree as the impedance change due to cell attachment or growth on any other of the electrodes referred to. In other words, where electrodes have substantially the same surface area, any one of the electrodes can contribute to overall change in impedance upon cell attachment or growth on the electrode. In most cases, the ratio of surface area between the largest electrode and the smallest electrode that have "substantially the same surface area" is less than 10. Preferably, the ratio of surface area between the largest electrode and the smallest electrode of an electrode structure is less than 5, 4, 3, 2, 1.5, 1.2 or 1.1. More preferably, the at least two electrodes of an electrode structure have nearly identical or identical surface area.

As used herein, "said device has a surface suitable for cell attachment or growth" refers to the electrode and/or non-electrode area of the apparatus has appropriate physical, chemical or biological properties such that cells of interest can viably attach on the surface and new cells can continue to attach, while the cell culture grows, on the surface of the apparatus. However, it is not necessary that the device, or the surface thereof, contain substances necessary for cell viability or growth. These necessary substances, e.g., nutrients or growth factors, can be supplied in a medium. Preferably, when a suspension of viable, unimpaired, excitable cells is added to the "surface suitable for cell attachment" at least 50% of the cells adhere to the surface within twelve hours. More preferably, a surface that is suitable for cell attachment has surface properties so that at least 70% of the cells are adhering to the surface within twelve hours of plating (i.e., adding cells to the chamber or well that comprises the said device). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating.

As used herein, "detectable change in impedance between or among the electrodes" refers to the impedance between or among the electrodes would have a significant change that can be detected by an impedance analyzer or impedance measurement circuit when molecule binding reaction or cell attachment or cell adhesion or cell presence occurs on the electrode surfaces. The impedance change refers to the difference in impedance values when cell attachment or cell adhesion or cell presence or molecule binding reaction occurs on the electrode surface of the apparatus and when no molecular reaction occurs on the electrode surface or no cell is present on the electrode surface. The impedance change may occur upon the presence or decay of a beat from a cardiomyocyte. Alternatively, the impedance change refers to the difference in impedance values when cells are attached to the electrode surface and when cells are not attached to the electrode surface, or when the number, type, activity, or morphology of cells attached to the electrode-comprising surface of the apparatus changes. In most cases, the change in impedance is larger than 0.1% to be detectable. Preferably, the detectable change in impedance is larger than 1%, 2%, 5%, or 8%. More preferably, the detectable change in impedance is larger than 10%. Impedance between or among electrodes is typically a function of the frequency of the applied electric field for measurement. "Detectable change in impedance between or among the electrodes" does not require the impedance change at all frequencies being detectable. "Detectable change in impedance between or among the electrodes" only requires a detectable change in impedance at any single frequency (or multiple frequencies). In addition, impedance has two components, resistance and reactance (reactance can be divided into two categories, capacitive reactance and inductive reactance). "Detectable change in impedance between or among the electrodes" requires only that either one of resistance and reactance has a detectable change at any single frequency or multiple frequencies. In the present application, impedance is the electrical or electronic impedance. The method for the measurement of such impedance is achieved by, (1) applying a voltage between or among the electrodes at a given frequency (or multiple frequencies, or having specific voltage waveform) and monitoring the electrical current through the electrodes at the frequency (or multiple frequencies, or having specific waveform), dividing the voltage amplitude value by the current amplitude value to derive the impedance value; (2) applying an electric current of a single frequency component (or multiple frequencies or having specific current wave form) through said electrodes and monitoring the voltage resulted between or among the electrodes at the frequency (or multiple frequencies, or having specific waveform), dividing the voltage amplitude value by the current amplitude value to derive the impedance value; (3) other methods that can measure or determine electric impedance. Note that in the description above of "dividing the voltage amplitude value by the current amplitude value to derive the impedance value", the "division" is done for the values of current amplitude and voltage amplitude at same frequencies. Measurement of such electric impedance is an electronic or electrical process that does not involve the use of any reagents.

As used herein, "multiple pairs of electrodes or electrode structures spatially arranged according to wells of a multi-well microplate" refers to multiple pairs of electrodes or electrode structures of a device or apparatus are spatially arranged to match the spatial configuration of wells of a multi-well microplate so that, when desirable, the device can be inserted into, joined with, or attached to a multiwell plate (for example, a bottomless multiwell plate) such that multiple wells of the multi-well microplate will comprise electrodes or electrode structures.

As used herein, "arranged in a row-column configuration" refers to that, in terms of electric connection, the position of an electrode, an electrode array or a switching circuit is identified by both a row position number and a column position number.

As used herein, "each well contains substantially same number . . . of cells" refers to the lowest number of cells in a well is at least 50% of the highest number of cells in a well. Preferably, the lowest number of cells in a well is at least 60%, 70%, 80%, 90%, 95% or 99% of the highest number of cells in a well. More preferably, each well contains an identical number of cells.

As used herein, "each well contains . . . same type of cells" means that, for the intended purpose, each well contains same type of cells; it is not necessary that each well contains exactly identical type of cells. For example, if the intended purpose is that each well contains mammalian cells, it is permissible if each well contains same type of mammalian cells, e.g., human cells, or different mammalian cells, e.g., human cells as well as other non-human mammalian cells such as mice, goat or monkey cells, etc. In some instances the "same type of cells" may initially refer to embryonic stem cells; however, the stage of differentiation into cardiomyocytes may be differ.

As used herein, "each well contains . . . serially different concentration of a test compound" means that each well contains a test compound with a serially diluted concentrations, e.g., an one-tenth serially diluted concentrations of 1 M, 0.1 M, 0.01 M, etc.

As used herein, "dose-response curve" means the dependent relationship of response of cells on the dose concentration of a test compound. The response of cells can be measured by many different parameters. For example, a test compound is suspected to be cardiotoxic if it impairs cardiomyocyte beating, whether magnitude or amplitude or frequency, or if it causes cell death. Then the response of cells can be measured by percentage of non-viable (or viable) cardiac cells after the cells are treated by the test compound.

As used herein, "microelectrode strip or electrode strip" refers to a non-conducting substrate strip on which electrodes or electrode structure units are fabricated or incorporated. The non-limiting examples of the non-conducting substrate strips include polymer membrane, glass, plastic sheets, ceramics, insulator-on-semiconductor, fiber glass (like those for manufacturing printed-circuits-board). Electrode structure units having different geometries can be fabricated or made on the substrate strip by any suitable microfabrication, micromachining, or other methods. Non-limiting examples of electrode geometries include interdigitated electrodes, circle-on-line electrodes, diamond-on-line electrodes, castellated electrodes, or sinusoidal electrodes. Characteristic dimensions of these electrode geometries may vary from as small as less than 5 micron, or less than 10 micron, to as large as over 200 micron, over 500 micron, over 1 mm. The characteristic dimensions of the electrode geometries refer to the smallest width of the electrode elements, or smallest gaps between the adjacent electrode elements, or size of a repeating feature on the electrode geometries. The microelectrode strip can be of any geometry for the present invention. One exemplary geometry for the microelectrode strips is rectangular shape—having the width of the strip between less than 50 micron to over 10 mm, and having the length of the strip between less than 60 micron to over 15 mm. An exemplary geometry of the microelectrode strips may have a geometry having a width of 200 micron and a length of 20 mm. A single microelectrode strip may have two electrodes serving as a measurement unit, or multiple such two-electrodes serving as multiple measurement units, or a single electrode structure unit as a measurement unit, or multiple electrode structure units serving as multiple electrode structure units. In one exemplary embodiment, when multiple electrode structure units are fabricated on a single microelectrode strip, these electrode structure units are positioned along the length direction of the strip. The electrode structure units may be of squared-shape, or rectangular-shape, or circle shapes. Each of electrode structure units may occupy size from less than 50 micron by 50 micron, to larger than 2 mm×2 mm.

A "compound" or "test compound" is any compound whose activity or direct or indirect effect or effects on cells is investigated in any assay. A test compound can be any compound, including, but not limited to, a small molecule, a large molecule, a molecular complex, an organic molecule, an inorganic molecule, a biomolecule or biological molecule such as but not limited to a lipid, a steroid, a carbohydrate, a fatty acid, an amino acid, a peptide, a protein, a nucleic acid, or any combination thereof. A test compound can be a synthetic compound, a naturally occurring compound, a derivative of a naturally-occurring compound, etc. The structure of a test compound can be known or unknown. In one application of the present invention, a compound is capable of, or is suspected of, modulating the beating cycle of a cardiomyocyte cell population, whether by beating amplitude or frequency. In still another application, a compound is capable of, or is suspected of, interacting with cells (for example, binding to cell surface receptor, or inhibiting certain intracellular signal transduction pathway, or activating cells).

A "known compound" is a compound for which at least one activity is known. In the present invention, a known compound preferably is a compound for which one or more direct or indirect effects on cells is known. Preferably, the structure of a known compound is known, but this need not be the case. Preferably, the mechanism of action of a known compound on cells is known, for example, the effect or effects of a known compound on cells can be, as nonlimiting examples, effects on cardiotoxicity or embryonic stem cell development, etc.

An "impedance value" is the impedance measured for electrodes in a well with or without cell present. Impedance is generally a function of the frequency, i.e., impedance values depend on frequencies at which the measurement was conducted. For the present application, impedance value refers to impedance measured at either single frequency or multiple frequencies. Furthermore, impedance has two components, one resistance component and one reactance component. Impedance value in the present application refers to resistance component, or reactance component, or both resistance and reactance component. Thus, when "impedance value" was measured or monitored, we are referring to that, resistance, or reactance, or both resistance and reactance were measured or monitored. In many embodiments of the methods of the present application, impedance values also refer to parameter values that are derived from raw, measured impedance data. For example, cell index, or normalized cell index, or delta cell index could be used to represent impedance values.

A "Cell Index" or "CI" is a parameter that can derived from measured impedance values and that can be used to reflect the change in impedance values. There are a number of methods to derive or calculate Cell Index.

A "Normalized Cell Index" at a given time point is calculated by dividing the Cell Index at the time point by the Cell Index at a reference time point. Thus, the Normalized Cell Index is 1 at the reference time point.

A "delta cell index" at a given time point is calculated by subtracting the cell index at a standard time point from the cell index at the given time point. Thus, the delta cell index is the absolute change in the cell index from an initial time (the standard time point) to the measurement time.

A "Cell Change Index" or "CCI" is a parameter derived from Cell Index and "CCI" at a time point is equal to the $1^{st}$ order derive of the Cell Index with respect to time, divided by the Cell Index at the time point. In other words, CCI is calculated as $$CCI(t) = \frac{dCI(t)}{CI(t) \cdot dt}.$$

As used herein, "primary cell" or "primary cells" refers to any non-immortalized cell that has been derived from various tissues and organs of a patient or an animal.

B. Introduction to Impedance-Based Systems and Methods Having Millisecond Time Resolution The impedance-based system and methods of the present invention fill a major technological gap in monitoring of excitation-contraction coupling and excitable cells, such as cardiomyocytes, in vitro. This is accomplished, in part, from the development of an impedance-based system and monitoring method that employs millisecond time resolution. Millisecond timer resolution permits effective monitoring of excitable cells for short durations, such as less than about 100 milliseconds. Further by coupling millisecond time resolution with longer duration time periods, both short term and long term effects of drugs, such as cell viability, changes in morphology and adhesion can also be assessed. These combination studies permit further data collection with respect to compounds such as β-2 adrenergic receptor agonists, well known and characterized modulators of heart function in vivo and in vitro, which can induce long term hypertrophic responses in cardiomyocytes, which is associated with elongated morphology of the cells. When combining long term monitoring and short term monitoring it may be desirable to provide long term monitoring coupled to intermittent short term monitoring periods.

The devices, systems and methods provided permit impedance-based monitoring of excitable cells using millisecond time resolution. It has been discovered that by developing enhanced impedance based systems, detailed analysis of excitable cells, the excitation cycle of cells and potential modulators of excitable cells can be performed. Further, by studying the excitation cycle with increased resolution embodiments of the invention permit the effective evaluation of factors that may alter normal or abnormal cycling. Without millisecond time resolution, it would not be possible to perform detailed analysis of the beating cycle of the excitable cells. For example, for cardiomyocytes, if the impedance is measured at seconds time-resolution such as a ten-second or even one-second resolution, it would not be possible to observe beating of the cardiomyocytes or resolve a beating cycle of the cardiomyocytes with an impedance measurement. The cardiomyocytes-beating-resulted impedance change would be shown as "noise" on the impedance curves measured at seconds or minutes time-resolution. Indeed, it was a surprise that the beating of the cardiomyocytes on the electrode surfaces would result in periodic change in impedance and even more surprise that the impedance measurement, when performed at appropriate time resolution of milli-seconds, could resolve such beating cycles. After we discovered that cardiomyocyte beating, when cultured on electrode surfaces, can be monitored via impedance measurement, we interpreted that such dynamic monitoring of cardiomyocyte beating is based on quantification in real time of the rhythmic changes in cardiomyocyte morphology and/or attachment as a result of the excitation contraction coupling of the electrically excitable cardiomyocytes growing on microelectrodes' surface in E-PLATES (ACEA Biosciences, San Diego, Calif.). The quantification of the rhythmic changes in cardiomyocyte morphology and/or attachment is achieved via the fast (millisecond resolution) and continuous measurement of electrode impedance. The method essentially provides a cellular cardio-gram which can provide incisive information about the status of cardiomyocytes especially upon treatment with pharmacological agents.

When combining long term impedance monitoring and short term monitoring it may be desirable to provide long term monitoring coupled to intermittent short term monitoring. In other words, while long term impedance monitoring is able to identify long term effects on excitable cells, short term impedance monitoring, such as at millisecond time resolution may be employed at particular time points to assess short term effects. In some instances, impedance monitoring with millisecond time resolution is performed at regular or irregular time intervals. In these instances, time intervals may be preprogrammed in the system or may be initiated by the user. In some instances intermittent measuring at millisecond time resolution is initiated upon the occurrence of an event, such as an event detected or determined while long term monitoring of impedance. Such events may be changes in measured impedance data, changes in optical property and the like. Monitoring at millisecond time resolution may continue until a programmed event occurs, such as expiration of a time period. After or during which, long term impedance monitoring may continue.

In some embodiments, long term and short term monitoring of excitation-contraction coupling or excitable cells is provided in combination. Exemplary methods include providing the impedance-based system with millisecond time resolution; adding excitable cells or cells suspected of excitation-contraction coupling to one or more wells; monitoring impedance of the one or more wells over a first time period, which is characterized as a longer time period, such as seconds, minutes, hours or days; monitoring impedance of the one or more wells over a second time period in millisecond time resolution; determining a characteristic, such as cell attachment, cell growth and cell viability from monitoring over the first time period; and resolving individual cycles of the excitable cells from monitoring over the second time period. In such embodiments, monitoring impedance over the second time period may be performed at regular or irregular time intervals within monitoring impedance over the first time period. Further, test agents may be added to assess their short term effects and long term effects on the cells.

Impedance monitoring using, at least in part, millisecond time resolution will be useful in the testing of compounds such as drugs for the treatment or prevention of various medical conditions or their safety. In some embodiments the systems and methods are used to test or evaluate potential compounds, drugs or treatments for cardiotoxicity data. In some embodiments potential compounds, drugs or treatments are tested for cardioprotective data. In some embodiments potential compounds, drugs or treatments are tested for potential applicability for cardiovascular treatments, including hypertension or congestive heart failure. In some embodiments potential compounds, drugs or treatments are tested for modulation of embryonic stem cell development, such as development into cardiomyocytes. In other embodiments the systems and methods are used to test or assess potential drugs or treatments for neurological data, such as beneficial or deleterious neurological effects. As will be understood by those skilled n the present art, the impedance based system and methods including millisecond time resolution permits evaluation across multiple cell populations or systems that including excitation-contraction coupling.

One skilled in the art will understand embodiments of the present invention may be used for studying a variety of excitable cells or effects thereon. As nonlimiting examples cells may be cardiac muscle cells, neurological cells, differentiating stem cells, embryonic stem cells, adult stem cells and the like. Smooth muscle cells and skeletal muscle cells that undergo excitation-contraction coupling may also be studied.

In some embodiments of the present invention the excitation cycle or beating of cardiomyocytes is studied. Cardiomyocytes are specialized muscle cells, which make up the majority of the volume of the myocardium. The myocardium also includes epithelial cells and fibroblasts. Cardiomyocytes are arranged largely in a circumferential and spiral orientation around the left ventricle, the chamber that pumps blood to the systemic circulation. Atrial myocytes, also cardiomyocytes, are smaller in diameter and less structured than their ventricular counterparts. Cardiomyocytes have five major components: cell membrane (sarcolemma) and T-tubules, for impulse conduction; sarcoplasmic reticulum, a calcium reservoir needed for contraction; contractile elements; mitochondria; and nucleus. Cellularly, cardiomyocytes may be identified by the presence of cardiac tropnin T (TnT) and atrial natriuretic peptide (ANP).

The functional intracellular contractile unit of cardiac muscle (like skeletal muscle) is the sarcomere, an orderly arrangement of thick filaments composed principally of myosin, and thin filaments containing actin. Contraction of cardiac muscle occurs by the cumulative effort of sliding of the actin filaments between the myosin filaments toward the center of each sarcomere.

Cardiomyocytes may be obtained or isolated from cardiac tissue directly, may be cultured from cardiomyocyte cells or may be differentiated from stem cells, such as embryonic stem cells. In some embodiments embryonic or adult stem cells are used. Methods for obtaining or isolating cardiomyocytes from cardiac tissue may be found in the literature.

Since embryonic stem (ES) cells are self renewing cells in culture they can serve as an excellent source for continuous production of cardiomyocytes. These derived cardiomyocytes, which behave in every way like normal cardiomyocytes isolated from the heart tissue itself, addresses the ever important supply problem and for the first time allows for assessment of cardiac function and its modulation by lead candidate drugs and compounds in relatively large scale. Furthermore, because the technology exists to selectively knockout or express trans-genes in ES cells, it provides an excellent model system to study the role of certain genes in cardiac development and function without concern of adverse affects on overall embryonic development in transgenic animals. Further, the ability to express transgenes in ES cells has been utilized as a way to enrich for preparation of cardiomyocytes that are 100% pure. For example, the gene encoding GFP has been cloned downstream of a cardiac-specific promoter and then introduced into ES cells. Embryoid cells which ultimately differentiate into cardiomyocytes express the GFP transgenes and can be easily identified and isolated by cell sorting techniques and therefore an enriched cardiomyocyte population can be obtained.

C. Impedance-Based Systems Having Millisecond Time Resolution

In preferred embodiments the system for monitoring impedance of excitable cells in vitro includes a device for monitoring cell-substrate impedance, an impedance analyzer capable of impedance measurements at millisecond time resolution, electronic circuitry that can engage the device and selectively connect two or more electrode arrays of the device to the impedance analyzer and a software program that controls the electronic circuitry and records and analyzes data obtained from the impedance analyzer. By providing the impedance based system with millisecond time resolution, excitation-contraction coupling cells can be efficiently monitored and studied. Accordingly, the systems provided herein are able to identify and evaluate changes in excitation-contraction events, which may be used for high throughput analysis of potential therapeutics. Millisecond time resolution measurements may be coupled with longer term impedance monitoring, such as longer than seconds, hours or days. In some embodiments, long term impedance monitoring is performed with intermittent periods of impedance monitoring at millisecond time resolution.

Embodiments of the device for monitoring substrate impedance include a nonconductive substrate having one or more individually addressable electrode arrays fabricated thereon and one or more wells. A surface of the substrate may be suitable for cell attachment, wherein the cell attachment results in a detectable change in impedance between electrodes within the array. Preferably, the nonconducting substrate is planar, and is flat or approximately flat. The substrates may be constructed from a variety of nonconductive materials known in the present art, including, but not limited to, silicon dioxide on silicon, silicon-on-insulator (SOI) wafer, glass (e.g., quartz glass, lead glass or borosilicate glass), sapphire, ceramics, polymer, fiber glass, plastics, e.g., polyimide (e.g. Kapton, polyimide film supplied by DuPont), polystyrene, polycarbonate, polyvinyl chloride, polyester, polypropylene and urea resin. Preferably, the substrate is biocompatible with excitable cells; however, materials that are not biocompatible can be made biocompatible by coating with a suitable material, such as a biocompatible polymer or coating. Further, attachment or growth along the substrate or electrodes may be enhanced by precoating the substrate with a protein or compound that facilitates attachment or growth. Such compounds may be chosen according to techniques known in the cellular biology arts; however, in some embodiments fibronectin is effective. Alternatively, the substrate may be chemically modified to display reactive groups that enhance cell attachment, particularly ES cells or cardiomyocytes.

Each electrode array includes two or more electrode structures that are constructed to have dimensions and spacing such that they can, when connected to a signal source, operate as a unit to generate an electrical field in the region of spaces around the electrode structures. Preferably the electric field is substantially uniform across the array. An electrode structure refers to a single electrode, particularly one with a complex structure. Specifically, an electrode array includes two electrode structures, each of which includes multiple electrode elements, or substructures, which branch from the electrode structure. In preferred embodiments, the electrode structures of each of the two or more electrode arrays of a device have substantially the same surface area.

Each of the two electrode structures of an electrode array is connected to a separate connection pad that is preferably located at the edge of the substrate. Specifically, for each of the two or more electrode arrays of the device, preferably the first of the two electrode structures is connected to one of the two or more connection pads, and the second of the two electrode structures is connected to another of the two or more connection pads. Preferably, each array of a device is individually addressed, meaning that the electrical traces and connection pads of the arrays are configured such that an array can be connected to an impedance analyzer in such a way that a measuring voltage can be applied across a single array at a given time by using switches (such as electronic switches).

Preferably, each electrode array of the device has an approximately uniform electrode resistance distribution across the entire array. By "uniform resistance distribution across the array" is meant that when a measurement voltage is applied across the electrode structures of the array, the electrode resistance at any given location of the array is approximately equal to the electrode resistance at any other location on the array. Preferably, the electrode resistance at a first location on an array of the device and the electrode resistance at a second location on the same array does not differ by more than 30%. More preferably, the electrode resistance at a first location on an array of the device and the electrode resistance at a second location on the same array does not differ by more than 15%. Even more preferably, the electrode resistance at a first location on an array of the device and a second location on the same array does not differ by more than 5%. More preferably yet, the electrode resistance at a first location on an array of the device and a second location on the same array does not differ by more than 2%.

Preferred arrangements for electrode elements and gaps between the electrodes and electrode buses in a given electrode array are used to allow all cells, no matter where they land and attach to the electrode surfaces and to contribute similarly to the total impedance change measured for the electrode array. Thus, it is desirable to have similar electric field strengths at any two locations within any given array of the device when a measurement voltage is applied to the electrode array. At any given location of the array, the field strength is related to the potential difference between the nearest point on a first electrode structure of the array and the nearest point on a second electrode structure of the array. It is therefore desirable to have similar electric potential drops across the electrode elements and across the electrode buses of a given array. Based on this requirement, it is preferred to have an approximately uniform electrode resistance distribution across the whole array where the electrode resistance at a location of interest is equal to the sum of the electrode resistance between the nearest point on a first electrode structure (that is the point on the first electrode structure nearest the location of interest) and a first connection pad connected to the first electrode structure and the electrode resistance between the nearest point on a second electrode structure (that is the point on the first electrode structure nearest the location of interest) and a second connection pad connected to the second electrode structure.

Preferably, devices of the present invention are designed such that the arrays of the device have an approximately uniform distribution across the whole array. This can be achieved, for example, by having electrode structures and electrode buses of particular spacing and dimensions (lengths, widths, thicknesses and geometrical shapes) such that the resistance at any single location on the array is approximately equal to the resistance at any single other location on the array. In most embodiments, the electrode elements (or electrode structures) of a given array will have even spacing and be of similar thicknesses and widths, the electrode buses of a given array will be of similar thicknesses and widths, and the electrode traces leading from a given array to a connection pad will be of closely similar thicknesses and widths. Thus, in these preferred embodiments, an array is designed such that the lengths and geometrical shapes of electrode elements or structures, the lengths and geometrical shapes of electrode traces, and the lengths and geometrical shapes of buses allow for approximately uniform electrode resistance distribution across the array.

In some preferred embodiments of impedance measurement devices, electrode structures comprise multiple electrode elements, and each electrode element connects directly to an electrode bus. Electrode elements of a first electrode structure connect to a first electrode bus, and electrode elements of a second electrode structure connect to a second electrode bus. In these embodiments, each of the two electrode buses connects to a separate connection pad via an electrical trace. Although the resistances of the traces contribute to the resistance at a location on the array, for any two locations on the array the trace connections from the first bus to a first connection pad and from the second bus to a second connection pad are identical. Thus, in these preferred embodiments trace resistances do not need to be taken into account in designing the geometry of the array to provide for uniform resistances across the array.

In preferred embodiments of the present invention, a device for monitoring cell-substrate impedance has two or more electrode arrays that share a connection pad. Preferably one of the electrode structures of at least one of the electrode arrays of the device is connected to a connection pad that also connects to an electrode structure of at least one other of the electrode arrays of the device. Preferably for at least two arrays of the device, each of the two or more arrays has a first electrode structure connected to a connection pad that connects with an electrode structure of at least one other electrode array, and each of the two or more arrays has a second electrode structure that connects to a connection pad that does not connect with any other electrode structures or arrays of the device. Thus, in preferred designs of a device there are at least two electrode arrays each of which has a first electrode structure that is connected to a common connection pad and a second electrode structure that is connected to an independent connection pad.

In some preferred embodiments of the present invention, each of the electrode structures of an array is connected to an electrode bus that is connected to one of the two or more connection pads of the device via an electrically conductive trace. In preferred embodiments, each of the two electrode structures is connected to a single bus, such that each array connects to two buses, one for each electrode structure. In this arrangement, each of the two buses connects to a separate connection pad of the substrate.

The electrically conductive traces that connect a bus with a connection can be fabricated of any electrically conductive material. The traces can be localized to the surface of the substrate, and can be optionally covered with an insulating layer. Alternatively the traces can be disposed in a second plane of the substrate. Description of arrangements and design of electrically conductive traces on impedance measurement devices can be found in U.S. Pat. No. 7,470,533, herein incorporated by reference for all disclosure on fabrication and design of electrically conductive trace on substrates.

Appropriate electronic connection means such as metal clips engaged onto the connection pads on the substrate and connected printed-circuit-boards can be used for leading the electronic connections from the connection pads on the devices to external electronic circuitry (e.g. an impedance analyzer). Description of the design of cell-substrate impedance devices and their manufacture can be found in U.S. Pat. No. 7,470,533, herein incorporated by reference for all description and disclosure of the design, features, and manufacture of impedance device comprising electrode arrays.

Descriptions of electrode arrays used for impedance measurement that apply to the devices of the present invention are described in U.S. Pat. No. 7,470,533, herein incorporated by reference for all disclosure relating to electrode arrays (or structural units), electrode structures, electrode materials, electrode dimensions, and methods of manufacturing electrodes on substrates.

Preferred electrode arrays for devices of the present invention include arrays comprising two electrode structures, such as, for example, spiral electrode arrays and interdigitated arrays. In some preferred devices of the present invention, electrode arrays are fabricated on a substrate, in which the arrays comprises two electrode structures, each of which comprises multiple circle-on-line electrode elements, in which the electrode elements of one structure alternate with the electrode elements of the opposite electrode structure. Electrode arrays may be provided in configurations, such as interdigitated, circle-on-line, diamond-on-line, concentric, sinusoidal and castellated.

Preferably, the electrode elements (or electrode structures) of an array of the present device of the present invention are of approximately equal widths. Preferably the electrode elements (or electrode structures) of an array of the present device of the present invention are greater than 20 microns and less than 500 microns in width, more preferably from about 50 to about 300 microns in width.

Preferably, the electrode elements (or electrode structures) of an array of the present device of the present invention are approximately evenly spaced. Preferably, the gap between electrode elements (or electrode structures) of an array of the present device of the present invention is less than 100 microns and more than 5 microns in width, more preferably from about 10 to about 80 microns in width.

A device of the present invention can include one or more fluid-impermeable receptacles which serve as fluid containers or wells. Such receptacles may be reversibly or irreversibly attached to or formed within the substrate or portions thereof (such as, for example, wells formed as in a microtiter plate). In another example, the device of the present invention includes microelectrode strips reversibly or irreversibly attached to plastic housings that have openings that correspond to electrode structure units located on the microelectrode strips. Suitable fluid container materials comprise plastic, glass, or plastic coated materials such as a ceramic, glass, metal, etc. Descriptions and disclosure of devices that comprise fluid containers can be found in U.S. Pat. No. 7,470,533, herein incorporated by reference for all disclosure of fluid containers and fluid container structures that can engage a substrate comprising electrodes for impedance measurements, including their dimensions, design, composition, and methods of manufacture.

In preferred embodiments, each electrode array on the substrate of a device of the present invention is associated with a fluid-impermeable container or receptacle, such as, for example, a well. Preferably, the device of the present invention is assembled to a bottomless, multiwell plastic plate or strip with a fluid tight seal. The device is assembled such that a single array of the substrate is at the bottom of a receptacle or well. Preferably, each array of a device is associated with a well of a multiwell plate. In some preferred embodiments, a multiwell device for cell-substrate impedance measurement has "non-array" wells that are attached to the substrate but not associated with arrays. Such wells can optionally be used for performing non-impedance based assays, or for viewing cells microscopically.

The design and assembly of multiwell impedance measurement devices is described in U.S. Pat. No. 7,470,533, and also in U.S. Pat. No. 7,192,752, both herein incorporated by reference for disclosure of multiwell impedance measurement devices, including their design, composition, and manufacture. A device of the present invention preferably has between 2 and 1,536 wells and more preferably between 4 and 384 wells. In some embodiments the device includes 6 wells, 16 wells, 32 wells, 96 wells or 386 wells.

In some preferred embodiments, commercial tissue culture plates can be adapted to fit a device of the present invention. Bottomless plates may also be custom-made to preferred dimensions. Preferably, well diameters are from about 1 millimeter to about 20 millimeters, more preferably from about 2 millimeters to about 8 millimeters at the bottom of the well (the end disposed on the substrate). The wells can have a uniform diameter or can taper toward the bottom so that the diameter of the container at the end in contact with the substrate is smaller than the diameter of the opposing end.

In the system for monitoring impedance of excitable cells the impedance analyzer engages connection pads of one or more multi-well devices to measure impedance. In one embodiment of the above system, the impedance analyzer is capable of measuring impedance between 0.1 ohm and $10^5$ ohm in frequency range of 1 Hz to 1 MHz. The impedance analyzer is preferably capable of measuring both resistance and reactance (capacitive reactance and inductive reactance) components of the impedance. In a preferred embodiment of the above system, the impedance analyzer is capable of measuring impedance between 1 ohm and $10^3$ ohm in frequency range of 1.00 Hz to 300 kHz.

In preferred embodiments the impedance analyzer is capable of impedance measurements at millisecond time resolution. The required or desired time resolution may vary depending on the excitation cycle of the excitable cell. Excitable cells having shorter excitation cycles would tend to require faster time resolution. In some embodiments 500 millisecond time resolution is sufficient, such that at least two consecutive impedance measurements are between about 300 milliseconds and about 500 milliseconds apart. In preferred embodiments, impedance measurement at millisecond time resolution includes at least two consecutive impedance measurements less than 100 milliseconds apart. In some instances the at least two consecutive impedance measurements are less than 50 milliseconds or less than 40 milliseconds apart. In some instances the at least two consecutive impedance measurements are less than 20 milliseconds apart. In some instances at least two consecutive impedance measurements are less than 10 milliseconds apart. In some instances millisecond time resolution includes two consecutive impedance measurements between 1 millisecond and 5 milliseconds, between 5 milliseconds and 10 milliseconds, between 10 milliseconds and 20 milliseconds, between 20 milliseconds and 40 milliseconds, or between 40 milliseconds and 50 milliseconds apart. In some instances millisecond time resolution includes at least two consecutive impedance measurements between 50 milliseconds and 100 milliseconds apart. In some instances millisecond time resolution includes at least two consecutive impedance measurements between 100 milliseconds and 150 milliseconds or between 150 and 300 milliseconds apart.

Millisecond time resolution of impedance-based devices provides a significant technical step over traditional impedance measuring devices, which are typically limited to second or minute resolution. That is, substantial reconfiguration of a traditional impedance-based system is required to obtain millisecond time resolution. Advances in multiple steps are required to achieve millisecond time resolution, including the impedance measurement circuitry together with electronic switching circuitry. Technological advances are further required when performing millisecond time resolution over multiple wells, such as 4 wells, 8 wells, 16 wells or 96 wells. For example, if the system comprises a device having 96 wells, the system hardware and software should be capable of, for a given time period, measuring the impedances of all 96 wells with millisecond time resolution between two adjacent or consecutive impedance measurement points for each and every well. Thus, comparing two impedance analyzers, one for impedance measurement of 96 wells with millisecond resolution and another for impedance measurement of a single well with millisecond time resolution, the one for 96 well measurement is effectively 96-times faster than one for a single well measurement since it is required to have a capability for performing impedance measurement for all 96 wells with millisecond time resolution. Similarly, if a 96 well device is provided, a group of wells, such as a group of 2, 4, 6, 12, 24 or 48 wells, may be measured in millisecond time resolution. Preferably, the time difference between two adjacent measurement points for each and every given well is less than 500 milliseconds. More preferably, the time difference between two adjacent measurement points for each and every given well is less than 300 milliseconds. Still more preferably, the time difference between two adjacent measurement points for each and every given well is less than 100 milliseconds. Still more preferably, the time difference between two adjacent measurement points for each and every given well is less than 40 milliseconds. Still more preferably, the time difference between two adjacent measurement points for each and every given well is less than 20 milliseconds. Still more preferably, the time difference between two adjacent measurement points for each and every given well is less than 10 milliseconds.

A number of improvements in the impedance measurement circuitry, electronic switching circuitry, communication between impedance measurement circuitry and software can be used to achieve such millisecond time resolution. For instance, improvement likely requires the use of fast processing electronic chips for analogue-to-digital conversion, for parallel digital signal processing and data calculation with field-programmable gate array (FPGA) and for fast communication between the impedance measurement circuitry and software. Another example of improvements includes the use of multiple analogue-to-digital (AD) conversion channels so that analog electronic signals from multiple channels can be converted to digital signals simultaneously. Such parallel AD conversion is important, particular for the system having multiple wells, each of which's measurement time resolution is required to be in the millisecond resolution. And, a very important is to replace previous working mode of "measurement of one-well's impedance at a time" with a mode of "measurement of multiple-wells' impedances at a time". In "one-well at a time" mode, when the software issue a command for measuring one well's impedance, the measurement circuitry would perform the measurement for one well including signal generation to the well, converting the voltage signal and the electric current signal for the well to digital signal, digitally processing the signals to do impedance calculation and sending the well's impedance data to the computer over the communication line between the impedance measurement circuitry and the computer. The system will not perform any measurement for another well until the completion of the measurement of this well and until receiving another command for the measurement of another well. In "multiple-wells at a time" mode, the software would issue a command for measuring multiple wells' impedances. The measurement circuitry would simultaneously or nearly simultaneously perform signal conversion, signal processing and impedance calculation for multiple wells. The multiple impedance data for the multiple wells would be sent over the communication lines to the computer sequentially with one well's data at the same time or simultaneously with more than one well's data being sent at a time. In this "measurement of multiple-wells' impedances at a time" mode, the system may be performing multiple tasks simultaneously, for example, while one well's impedance data is being measured and calculated, another well's impedance data may be communicated and sent over the communication lines to the computer.

With millisecond time resolution for impedance measurement, it becomes possible to resolve individual beating cycles of cardiomyocytes cultured on electrodes. Whilst theoretically one needs at least two data points for each beating cycle, in practice more than 2 data points are needed for each beating cycle. For example, if cells have a beating rate of 60 beats per minute, i.e, one beat per second. It would be preferred to have a time resolution of at least 200 milliseconds so that each beating cycle consists of 5 data points. More preferably, the measurement time resolution is 100 milliseconds. Still more preferably, the time resolution is 50 milliseconds or less.

One skilled in the art will understand that the cell-substrate impedance measurement or monitoring system with millisecond time resolution can be used to efficiently and simultaneously perform multiple assays by using circuitry of the device station to digitally switch from recording from measuring impedance over an array in one well to measuring impedance over an array in another well. Similarly, groups of wells may be monitored simultaneously and switching between occur between designated groups. In one embodiment of the above system, the system under software control is capable of completing an impedance measurement for an individual well at a single frequency within milliseconds, such as less than 100 milliseconds, less than 40 milliseconds, less than 20 milliseconds, less than 10 milliseconds or between 1 millisecond and 40 milliseconds. In some embodiments the user may choose the frequency of measurement for millisecond time resolution.

A multiple-well cell-substrate impedance measuring device in a system of the present invention can be any multiple-well cell-substrate impedance measuring device in which at least two of the multiple wells comprise an electrode array at the bottom of the well, and in which at least two of the multiple wells comprise an electrode array are individually addressed. In one embodiment of the above system, the multi-well device takes the form of a specialized microtiter plate which has microelectronic sensor arrays integrated into the bottom of the wells.

A device used in a system of the present invention, when connected to an impedance analyzer, can measure differences in impedance values that relate to cell behavior. For example, a cell-substrate impedance measuring device used in a system of the present invention can measure differences in impedance values when cells are attached to the electrode array and when cells are not attached to the electrode array, or can detect differences in impedance values when the number, type, activity, adhesiveness, or morphology of cells attached to the electrode-comprising surface of the apparatus changes. Further, by using millisecond time resolution differences in impedance may be detected or monitored that relate to excitation-contraction coupling, including the beating of cardiomyocytes or stem cells differentiating into cardiomyocytes, and the signaling between neurological cells. Impedance monitoring of the excitation cycle of excitable cells may be determined and monitored before, during or after adding a test compound, which is suspected of affecting the excitation cycle. Thus, by monitoring the excitation cycle of the excitable cell before, during or after adding a test compound the system provides data corresponding to the potential affect of the compound on the cardiovascular system, the heart, the nervous system, and the like. In some embodiments monitoring the excitation cycle of the cell before, during or after adding a compound provides cardiotoxicity data useful in drug screening.

In some embodiments a device station or electromechanical apparatus or assembly capable of interfacing multiwell devices can include one or more platforms or one or more slots for positioning one or more multiwell devices. The one or more platforms or one or more slots can comprise sockets, pins or other devices for electrically connecting the device to the device station. The device station or electromechanical apparatus or assembly capable of interfacing multiwell devices preferably can be positioned in a tissue culture incubator during cell impedance measurement assays. It can be electrically connected to an impedance analyzer and computer that are preferably located outside the tissue culture incubator.

The device station or electromechanical apparatus or assembly capable of interfacing multiwell devices includes electronic circuitry that can connect to the impedance monitoring device and an impedance analyzer and electronic switches that can switch on and off connections to each of the two or more electrode arrays of the multiwell devices used in the system. The switches of the device station or electromechanical apparatus or assembly capable of interfacing multiwell devices are controlled by a software program, each of which has been improved to provide millisecond time resolution. The software program directs the device station to connect arrays of the device to an impedance analyzer and monitor impedance from one or more of the electrode arrays. During impedance monitoring, the impedance analyzer can monitor impedance at one frequency or at more than one frequency. Preferably, impedance monitoring is performed at more than one time point for a given assay, and preferably, impedance is monitored using at least two time points. The device station can connect individual arrays of a device to an impedance analyzer to monitor one, some, or all of the arrays of a device for a measurement time point. In some preferred embodiments of the present invention, the device station software is programmable to direct impedance monitoring of any of the wells of the device that comprise arrays at chosen time intervals.

The software of the impedance monitoring system can also store and display data. Data can be displayed on a screen, as printed data, or both. Preferably the software can allow entry and display of experimental parameters, such as descriptive information including cells types, compound concentrations, time intervals monitored, etc.

Preferably, the software can also analyze impedance data. In preferred embodiments, the software can calculate a cell index (CI) for one or more time points for one or more wells of the multiwell device. In some preferred embodiments, the software can calculate a cell change index (CCI) from impedance measurements of one or more wells of the multiwell device. The software can preferably generate plots of impedance data and impedance values, such as but not limited to CI or CCI, with respect to time. The software may perform other analysis as well, such as calculate cell number from CI, generate dose-response curves based on impedance data, calculate IC values based on impedance values, and calculate kinetic parameters of the excitation cycle cell based on impedance values and impedance value curves. In some embodiments the beating cycle of a cardiomyocyte population is determined, which may include initiation and decay of individual beats. Peaks may be derived from the detection of vectors associated with initiation of beating or beating decay. Peaks may be derived with other methods. In further embodiments the change in beating cycle of a cardiomyocyte population is determined in response to a stimulus such as a pharmacological agent. The software of the impedance monitoring system can also store and display analyses of the data, such as calculated impedance values and kinetic parameters derived therefrom, Data can be displayed on a screen, as printed data, or both. Data may be stored on a hard drive for exportation into compatible programs for further analysis or data storage Further information regarding how to calculate a cell index, cell change index, normalized cell index, and delta cell index may be found in U.S. patent application Ser. No. 11/235,938, and U.S. Pat. No. 7,470,533, the contents of which are herein incorporated by reference with respect to the cell index, cell index number, cell change index, and cell change index number. However each is briefly summarized.

The cell index obtained for a given well reflects: 1) how many cells are attached to the electrode surfaces in this well, 2) how well cells are attached to the electrode surfaces in the well. In this case, a zero or near-zero "cell index or cell number index" indicates that no cells or very small number of cells are present on or attached to the electrode surfaces. In other words, if no cells are present on the electrodes, or if the cells are not well-attached onto the electrodes cell index=0. A higher value of "cell number index" indicates that, for same type of the cells and cells under similar physiological conditions, more cells are attached to the electrode surfaces. Thus Cell Index is a quantitative measure of cell number present in a well. A higher value of "cell index" may also indicate that, for same type of the cells and same number of the cells, cells are attached better (for example, cells spread out more, or cell adhesion to the electrode surfaces is stronger) on the electrode surfaces.

A "Normalized Cell Index" at a given time point is calculated by dividing the Cell Index at the time point by the Cell Index at a reference time point. Thus, the Normalized Cell Index is 1 at the reference time point. Normalized cell index is cell index normalized against cell index at a particular time point. In most cases in the present applications, normalized cell index is derived as normalized relative to the time point immediately before a compound addition or treatment. Thus, normalized cell index at such time point (immediately before compound addition) is always unit one for all wells. One possible benefit for using such normalized cell index is to remove the effect from difference in cell number in different wells. A well having more cells may produce a larger impedance response following compound treatment. Using normalized cell index, it helps to remove such variations caused by different cell numbers.

A "delta cell index" at a given time point is calculated by subtracting the cell index at a standard time point from the cell index at the given time point. Thus, the delta cell index is the absolute change in the cell index from an initial time (the standard time point) to the measurement time.

The time-dependent cellular response (including cardiotoxicity response) may be analyzed by deriving parameters that directly reflect the changes in cell status. For example, time dependent cellular response may be analyzed by calculating the slope of change in the measured impedance responses (that is equivalent to the first order derivative of the impedance response with respect to time, impedance response here can be measured impedance data or derived values such as cell index, normalized cell index or delta cell index). In another example, the time-dependent cellular responses (including cardiotoxic responses) may be analyzed for their higher order derivatives with respect to time. Such high order derivatives may provide additional information as for how cells responding to different compounds and as for the mechanisms of compound action.

Thus CCI is the normalized rate of change in cell index. CCI values can be used to quantify the cell status change. For cells in an exponential growth under regular cell culture condition, the cell index determined by a cell-substrate impedance monitoring system described herein is expected to be a proportionate measure of the cell number in the well since the cell morphology and average extent of cell adhesion to the electrode surfaces among the whole cell population do not exhibit significant changes over time.

After measuring and recording time dependent impedance data for excitable cells cultured on electrodes, various methods can be used for determining beating cycle peaks. For example, time dependent impedance values or cell index values for a well are analyzed by deriving their first order derivatives and second order derivatives using numerical methods. The beating cycle peaks are those data points where the first order derivatives of impedance values or cell index values are zero or close to zero in its absolute value. If the beating cycle peak is a positive peak (i.e. peak corresponds to a maximum value in measured impedance or cell index over the beating cycle), then the peak would correspond to the data points where the second order derivatives of the impedance values or cell index values is negative and where the first order derivatives of the impedance values or cell index values is zero or close to zero in its absolute value. If the beating cycle peak is a negative peak (i.e. peak corresponds to a minimum value in measured impedance or cell index over the beating cycle), then the peak would correspond to the data points where the second order derivatives of the impedance values or cell index values is positive and where the first order derivatives of the impedance values or cell index values is zero or close to zero in its absolute value. In another example, the method of determining a beating cycle peak is to search for the data point where the trend of the data changes direction from "increasing" to "decreasing" with time (for a positive peak), or from "decreasing" to "increasing" (for a negative peak). After the identification of the beating cycle peaks, the impedance or cell index values at such peak time points are the magnitude or amplitude of the beating cycle peaks.

After determining the beating cycle peaks, various methods can be used to calculate the beating rate. The beating rate can be determined by dividing a unit time (e.g., 1 minute) by the time period between two adjacent peaks. For example, if two adjacent peaks are separated by 500 milliseconds, then the beating rate for this 500 milliseconds can be determined as 120 beats per minute. Another method is simply to count how many peaks in a unit time by software. For example, if there are 2 peaks in one second interval, then the beating rate should be 2 beats per second, or 120 beats per minute.

D. Assessing or Quantifying Excitable Cells, Excitation Contraction-Coupling and Cardiomyocytes In Vitro In another aspect of the present invention a method for assessing or quantifying excitable cells in vitro is provided. The methods including detecting or monitoring excitable cells using impedance monitoring with millisecond time resolution. In preferred embodiments, the method includes providing the impedance based system having millisecond time resolution system, adding excitable cells to one or more wells of the device, monitoring impedance of the one or more wells with millisecond time resolution, and resolving individual cycles of the excitable cells. In some embodiments monitoring impedance further includes determining cell indices from impedance values, calculating average rate of excitation events per unit time (such as beats per unit time when using cardiomyocytes), determining amplitude intensity or average amplitude intensity in a unit time, and/or determining the length of time between excitation cycles (or beating cycles). These additional determinations may be compared to further assess excitable cells.

The methods have particular utility with cells that are known or suspected to be capable of or undergo excitation-contraction coupling, such as cardiomyocytes. Thus the methods may monitor, detect or determine excitation contraction-coupling of excitable cells. Further, even minor variations in excitation-contraction coupling may be detected.

Preferably impedance measurements are performed with millisecond time resolution. In some embodiments, two consecutive impedance measurements are performed at less than 300 milliseconds apart. In further embodiments, at least two consecutive impedance measurements are performed less than 100 seconds apart. In further embodiments, at least two consecutive impedance measurements are performed less than 40 milliseconds apart. In further embodiments, at least two consecutive impedance measurements are performed less than 10 milliseconds apart. In some embodiments at least two impedance measurements are between 1 millisecond and 50 milliseconds apart.

Cardiomyocytes are a subset of cells that are involved in excitation-contraction coupling. Embodiments of the present invention include applications for studying cardiomyocyte activity, function and its modulation. By monitoring the continuous rhythmic beating of cardiomyocytes, methods of the present invention allow the study of cardiomyocytes themselves as well as screening for pharmacological agents which may alter cardiomyocyte rhythmic beating. Thus the methods permit screening of compounds or conditions that affect cardiomyocyte function or induce cardiotoxicity. Specifically, methods may assess or quantify cardiomyocyte beating in vitro using impedance-based technology having millisecond time resolution. In preferred embodiments, the methods are based on quantification in real time of the rhythmic changes in cardiomyocyte morphology as a result of the excitation contraction coupling of the electrically excitable cardiomyocytes growing on microelectrodes' surface in E-PLATES (ACEA Biosciences, Inc. San Diego, Calif.). Thus quantification of the rhythmic changes in cardiomyocyte morphology is achieved via the measurement of electrode impedance, which may be performed with millisecond time resolution. In summary, some methods provide a cellular cardio-gram, which can provide incisive information about the status of cardiomyocytes especially upon treatment with pharmacological agents.

Cardiomyocytes used in the present invention may be any known or experimental cardiomyocyte population. Human cardiomyocytes will be particularly desirable when studying the effect of pharmacological agents for human use; however, cardiomyocytes may also be murine or mouse, rat, rabbit, dog, and the like. Further, the cardiomyocytes may be primary cardiomyocytes isolated from cardiac tissue or may be cultured cardiomyocytes, which are cultured over time. In some embodiments, ES cells destined to differentiate into cardiomyocytes are used. Isolated primary cardiomyocytes as well as ES-derived cardiomyocytes retain the ability to beat in culture. Thus, these cells provide a desirable model system to study cardiomyocyte function in vitro.

Cardiomyocytes have an innate ability to undergo mechanotransduction. In other words, the spontaneous force generated from the beating cardiomyocyte is translated to intracellular biochemical signals. Membrane receptors such as integrins, ion channels and other proteins have been shown to play a crucial role in cardiac mechanotransduction and lead to a continuous and rhythmic dynamics of the cardiac actin cytoskeleton and morphology. Because the impedance-based system can sensitively and precisely detect transient changes in morphology and adhesive capacity of the cells, it can be used to monitor cardiac function in vitro. Further, the development of millisecond time resolution permits impedance monitoring of the cardiomyocyte beating cycle as well as fluctuations, even minor alterations, in response to external stimuli.

Exemplary steps involved in using an impedance-measurement system for measurement of cardiomyocyte function include: providing a system for monitoring impedance of excitable cells, in vitro, which is capable of millisecond time resolution, optionally coating wells of the device with either fibronectin or other matrix proteins; seeding either embryonic stem cells (ES cells) of mammalian origin or primary cardiomyocytes at sufficient seeding densities into the wells of the device; allowing the cells to attach and spread; after a period of time unique to ES-derived cardiomyocytes or primary cardiomyocytes, monitoring cardiomyocyte beating using the impedance-monitoring system to monitor electrode impedance by using millisecond kinetic readout to resolve the individual beat cycles of the cells.

The millisecond kinetic readout requires the impedance measurement system be capable of obtaining impedance measurement data at millisecond time resolution. Preferably, the time difference between two consecutive impedance measurements for a well is within the range of milliseconds (e.g., less than 300 millisecond, less than 100 milliseconds, less than 50 milliseconds, less than 20 milliseconds, less than 10 milliseconds, or less than or about 1 millisecond). Due to the fast nature of beating cycles of cells, millisecond kinetic readout is required for proper resolution. Thus, the time resolution for the impedance measurement should allow the system to perform measurement using at least two time points for each beat cycle, or at more than two points for each beating cycle. In some embodiments, three, four, five or even ten, or fifteen or twenty or more time points within each beating cycle are obtained.

Embodiments of the present invention include methods of assessing or quantifying cardiomyocytes include providing the system for monitoring impedance of excitable cells in vitro, which includes millisecond time resolution, adding cardiomyocytes to one or more wells, monitoring impedance of the one or more wells, such as using millisecond time resolution, and resolving excitation cycle or beating cycle of the cardiomyocytes In further embodiments, the method also includes determining cell indices from impedance values, optionally calculating average rate of beats per unit time, average amplitude intensity in a unit time as well as the average length of time between the beats. In preferred embodiments, millisecond time resolution permits measurement of at least two consecutive impedance measurements within a beating cycle. In some embodiments at least three consecutive impedance measurements are performed with millisecond time resolution.

Isolated primary cardiomyocytes as well as ES-derived cardiomyocytes retain the ability to beat in culture. These cells provide an excellent model system to study cardiomyocyte function in vitro, especially with regards to cardiotoxicity. A number of cardiotoxic drugs are known to affect certain heart channels, such as the ERG channels, that are involved in excitation-contraction coupling of cardiomyocytes. Cardiomyocytes have an innate ability to undergo mechanotransduction, that is that the spontaneous force generation of the beating cardiomyocyte is translated to intracellular biochemical signals. Membrane receptors such as integrins, ion channels and other proteins have been shown to play a crucial role in cardiac mechanotransduction and lead to a continuous and rhythmic dynamics of the cardiac actin cytoskeleton and morphology. Because the impedance-based system can sensitively and precisely detect transient changes in morphology and adhesive capacity of the cells, thus it can be used to monitor cardiomyocyte beating in vitro.

Another exemplary method for impedance based measurement of cardiomyocyte beating includes: providing a single-well or multi-well device that comprise microelectrode arrays in well(s) of the device, which can be used for monitoring cell-substrate impedance; optionally coating wells of the device with either fibronectin or other matrix proteins; seeding either embryonic stem cells (ES cells) of mammalian origin or primary cardiomyocytes at specific seeding densities to the wells of the device; allowing the cells to attach and spread; after a specified period of time unique to ES-derived cardiomyocytes or primary cardiomyocytes, monitoring cardiomyocyte beating using the impedance-monitoring system to monitor electrode impedance by using millisecond kinetic readout to resolve the individual beat cycles of the cells.

In another exemplary embodiment for measurement of cardiomyocyte function the method includes: optionally coating E-PLATES with either fibronectin or other matrix proteins; seeding either ES cells of mammalian origin or primary cardiomyocytes at specific seeding densities; allowing the cells to attach and spread; after a specified period of time unique to ES-derived cardiomyocytes or primary cardiomyocytes, monitoring cardiomyocyte beating using an impedance-based system by using millisecond kinetic readout to resolve the individual beat cycles of the cells.

Dynamic monitoring of cardiomyocyte beating is based on quantification in real time of the rhythmic changes in cardiomyocyte morphology as a result of the excitation contraction coupling of the electrically excitable cardiomyocytes growing on microelectrodes' surface of E-PLATES. The quantification of the rhythmic changes in cardiomyocyte morphology is achieved via the fast, millisecond resolution and continuous measurement of electrode impedance. The method essentially provides a cellular cardio-gram which can provide incisive information about the status of cardiomyocytes especially upon treatment with pharmacological agents. An exemplary method includes providing a device for measuring cell-substrate impedance operably connected to an impedance analyzer, wherein the device includes at least one well optionally coated with fibronectin to expedite attachment; adding cells to the at least one well, where the cells can be mouse or human or other mammalian ES cells or adult stem cells destined to differentiate into cardiomyocytes or primary cardiomyocytes isolated directly from the heart of an experimental system including mice, rats, rabbits or dog; monitoring impedance of the at least one well at time intervals over a period of time and optionally determining cell indices from impedance values; optionally calculating average rate of beats per unit time, average amplitude intensity in a unit time as well as the average length of time between the beats.

Certain cardiotoxic drugs can illicit their effect by affecting the morphological aspects of cardiomyocyte morphology. For example, it is well known that compounds such as β-2 adrenergic receptor agonists can induce morphological changes resulting in an elongated cardiomyocyte morphology, otherwise known as hypertrophy. Morphological changes can occur immediately in the order of minutes as with certain GPCR agonists or can be of longer duration detectable over several days. The time resolution of the impedance-based system can be used to distinguish between different kinds of morphological effects. The steps involved in using an impedance-monitoring system for measurement of morphological modulation of cardiomyocytes may include: optionally coating E-PLATES with either fibronectin or other matrix proteins; seeding either embryonic stem cells (ES cells) of mammalian origin, mammalian adult stem cell-derived cardiomyocytes or primary cardiomyocytes isolated directly from mammalian heart tissue at specific seeding densities to the wells of the device; allowing the cells to attach and spread; monitoring cardiomyocyte viability over time using the impedance-monitoring system at prespecified intervals of time for 12, 24, 48, 72 hours or longer; at certain times after cell seeding, treat the cell with agents that may cause morphology changes at one or more concentration; using the vehicle that the agent is dissolved in as a control; continuing to monitoring the cardiomyocytes at 1 minute intervals for at least 1-2 hours to capture any immediate morphological changes and continue to monitor at 30 minutes intervals of time for additional 12, 24, 48, 72 hours or longer to detect long term morphological changes; and quantifying the extent of morphological change by normalizing the cell index values immediately prior to agent addition and determine the normalized cell index at a given time point after agent addition. The extent of morphological change can be expressed as EC-50 value which quantifies the activity of the agent with respect to the cardiomyocyte shape changes.

Once regular cardiomyocyte beating can be effectively monitored compounds may be added to the wells to assess whether or not beating frequency is altered, beating amplitude is altered and the like. Thus, compounds that adversely affect the normal cardiomyocyte beating are suspected of being cardiotoxic. However, cardioprotective agents can also be assessed by adding an agent suspected of being cardioprotective to the well and inducing a cardiotoxic response.

Accordingly, methods of identifying or screening for potential agents that modulate ES-derived cardiomyocyte beating or primary cardiomyocyte beating by monitoring and measuring the excitation-contraction coupling of cardiomyocytes upon treatment with pharmacological agents are also provided. The methods may include providing the system for monitoring impedance at millisecond resolution of excitable cells in vitro, adding ES cells or primary cardiomyocytes to two or more wells, adding a test agent suspected of modulating ES-derived or primary cardiomyocyte beating to a first well to provide a test well and either no agent or a control agent to a second well to form a control well, monitoring impedance of the two or more wells at different or similar time intervals using millisecond time resolution at least in part, and optionally determining cell indices from impedance values, generating an impedance-based curve or optionally a cell index curve for each of the test well and control well, and comparing the impedance-based curves or optionally the cell index curves between the test well and the control well. If significantly different, the test agent is concluded to modulate cardiomyocyte function. In preferred embodiments, the impedance-based curves may be direct measurement of cardiomyocyte excitation-contraction coupling; however, the methods may also include long term monitoring of the viability and or morphology of the cardiomyocytes. The methods may show whether the test agent increases cardiomyocyte beating, which is indicative of increased heart rate, or whether the cardiomyocyte beating is slowed, which is indicative of lowered heart rate.

In another exemplary embodiment a method for screening for modulators of cardiomyocyte beating using an impedance-measurement system in vitro may include: providing a single-well or multi-well device that comprise microelectrode arrays in well(s) of the device, which can be used for monitoring cell-substrate impedance; optionally coating wells of the device with either fibronectin or other matrix proteins; seeding either embryonic stem cells (ES cells) of mammalian origin, mammalian adult stem cell-derived cardiomyocytes or primary cardiomyocytes at specific seeding densities to the wells of the device; allowing the cells to attach and spread; after a specified period of time unique to ES-derived cardiomyocytes or primary cardiomyocytes, monitoring cardiomyocyte beating using the impedance-monitoring system to monitor electrode impedance by using millisecond kinetic readout to resolve the individual beat cycles of the cells; and adding the pharmacological agents at one or more doses and continue monitoring the cardiomyocyte beating frequency. Preferably, the step of monitoring impedance of beating is performed immediately prior to addition of pharmacological agent, in order to obtain a baseline of the cardiomyocyte beating frequency using fast measurement software and hardware to ensure milli-second kinetic readout signals.

In another exemplary embodiment, a method of screening for modulators of cardiomyocyte beating using an impedance-based system in vitro includes seeding cardiomyocytes, in E-PLATES exactly as described in the previous exemplary embodiment; however, prior to addition of pharmacological agent, obtaining a baseline of the cardiomyocyte beating frequency using the impedance measurement system with millisecond time resolution; and adding the pharmacological agents at one or more doses and continue monitoring the cardiomyocyte beating frequency.

It is well established that certain pharmacological treatments and disease conditions can result in cardiac hypertrophy or atrophy culminating in changes in the morphology of cardiomyocyte. Cell substrate impedance can be used to precisely measure and quantify these changes in cell morphology and shape. Certain treatments can also affect the differentiative process of ES cells to cardiomyocytes which may involve specific morphological and adhesive changes. In some embodiments the present invention is directed to a method to screen for potential agents that may modulate the morphology of ES-derived cardiomyocyte, adult stem cell-derived cardiomyocyte or primary cardiomyocyte or its differentiation. The agent may include but is not limited to compounds, drugs, peptides, proteins, antibodies, siRNA, shRNA, miRNA, cDNA, lipids and any combination thereof. The method includes providing a device for measuring cell-substrate impedance operably connected to an impedance analyzer, wherein the device includes at least two wells; adding ES cells, adult stem-cell derived cardiomyocytes or primary cardiomyocytes to at least two wells; monitoring impedance of the at least two wells at different or similar time intervals over a period of time and optionally determining cell indices from impedance values; generating an impedance-based curve or optionally a cell index curve for each of the at least one known factor and the control; comparing the impedance-based curves or optionally the cell index curves between the at least one known biologically active agent well and the control well; the impedance-based curves could be direct measurement of changes in cell morphology and if significantly different, concluding that the biologically active agent modulates cardiomyocyte function. Optionally, impedance-based curves or optionally cell index curves are used to calculate the compound dose-dependent changes in cardiomyocyte morphology and generate an EC-50 value for the potency of the compound.

The method of the present invention is to devise a label-free cell-based assay system for continuous monitoring of cardiomyocyte viability, the rhythmic beating of cardiomyocytes and cardiomyocyte morphology and differentiation and to screen for pharmacological agents which may modulate these processes and induce cardiotoxicity. In some embodiments, viability is monitored based on long term impedance monitoring of cardiomyocytes seeded in microelectronic plates (E-Plates). Viable cells will continue to generate impedance signal and any changes in viability, especially due to cytotoxic or cardiotoxic drugs will be reflected by changes in impedance. In one respect, the method includes providing a device for measuring cell-substrate impedance operably connected to an impedance analyzer, wherein the device includes at least one well optionally coated with fibronectin to expedite attachment; adding cells to the at least one well, where the cells can be mouse or human or other mammalian ES cells or adult stem cells destined to differentiate into cardiomyocytes or primary cardiomyocytes isolated directly from the heart of an experimental system including mice, rats, rabbits or dog; monitoring impedance of the at least one well over a period of time and optionally determining cell index from impedance values; In another aspect, the method includes providing a device for measuring cell-substrate impedance operably connected to an impedance analyzer, wherein the device includes at least two wells optionally coated with fibronectin to expedite attachment; adding cells to the at least two wells, where the cells can be mouse or human or other mammalian ES cells or adult stem cells destined to differentiate into cardiomyocytes or primary cardiomyocytes isolated directly from the heart of an experimental system including mice, rats, rabbits or dog; monitoring impedance of the at least two wells over a period of time and optionally determining cell index from impedance values. Treating at least one well with an agent; where the agent could include but is not limited to a compound, peptide, protein, antibody, siRNA, shRNA, lipid or any combination of thereof and the other well is treated with an appropriate control; continue monitoring of control and treated well over a period of time preoptimized for the experiment of interest; concluding that the factor may affect cell viability if the impedance or alternatively the cell index of the treated well is significantly different than the impedance or cell index of the treated well.

In other preferred embodiments short term measurement using millisecond time resolution is combined with longer term impedance monitoring, such as over seconds, hours, days and the like. Certain cardiotoxic drugs can directly affect the viability of cardiomyocytes. Thus, long term impedance monitoring may be used to assess loss of viability of cardiomyocytes. An exemplary long term method to assess loss of viability includes: optionally coating E-PLATES with either fibronectin or other matrix proteins; seeding either embryonic stem cells (ES cells) of mammalian origin, mammalian adult stem cell-derived cardiomyocytes or primary cardiomyocytes isolated directly from mammalian heart tissue at seeding densities to the wells of the device; allowing the cells to attach and spread; monitoring cardiomyocyte viability over time using the impedance-monitoring system to monitor electrode impedance at pre-specified intervals of time for specified length of time such as 12, 24, 37, 48, 72 hours or longer; at certain time after cell seeding, treating the cell with a cytotoxic agent at one or more concentration; using the vehicle that the agent is dissolved in as a control; continue monitoring the cardiomyocytes at pre-specified intervals of time for specified length of time such as additional 12, 24, 48, 72 hours or longer, quantify the extent of cardiotoxicity by normalizing the cell index values immediately prior to agent addition and determining the normalized cell index at a given time point after agent addition; alternatively the rate of cytotoxicity can also be quantified for a given time period after compound addition for a given agent concentration or a group of concentrations. The extent of cytotoxicity can be expressed as IC-50 value which quantifies the activity of the agent with respect to the cardiomyocytes.

In another aspect of the present invention, direct optical monitoring of cardiomyocytes is used to quantify and measure the beating of cardiomyocytes. The method includes providing a device for optically monitoring cells and monitoring cell morphology operably connected to an optical measurement system, where the device includes at least two wells optionally coated with fibronectin to expedite attachment; adding cells to the at least two wells, where the cells can be mouse or human or other mammalian ES cells destined to differentiate into cardiomyocytes or primary cardiomyocytes isolated directly from the heart of an experimental system including mice, rats, rabbits or dog; optically monitoring the cells of at least two wells at time intervals over a period of time via the optical measurement system; optionally calculating average rate of beats per unit time, average amplitude intensity in a unit time as well as the average length of time between the beats. The device for such optical measurement of cells may include microtiter plates. The optical system may include optical magnification instrument such as microscope, optical CCD camera, optical-signal processing algorithm to quantify cell beating and to derive cell-beating parameters (such as calculating average rate of beats per unit time, average amplitude intensity in a unit time as well as the average length of time between the beats) based on cell morphology images.

On skilled in the art will recognize that any agent may be tested. The agent may be a biologically active agent. Exemplary test agents include compounds, drugs, peptides, proteins, antibodies, antibody fragments, siRNA, shRNA, miRNA, cDNA, lipids and any combination thereof. Optionally, impedance-based curves or optionally cell index curves are used to calculate average rate of beats of cardiomyocytes per unit time, average amplitude intensity in a unit time as well as the average length of time between beats, comparison of these optionally derived parameters is made between the test well and the control well, and if significant differences exist, one may optionally conclude that the test agent modulates cardiomyocyte functions.

The study of cardiomyocyte function and modulation has particular utility in the biomedical arts. For example, the methods of the present invention may be used to assess whether a potential agent is cardiotoxic, cardioprotective and the like. If normal cardiomyocyte beating is altered, the result likely demonstrates the potential agent is cardiotoxic. Such information would permit effective screening prior to testing in live animals or in humans. Further, by coupling millisecond time resolution over extended time periods, the methods may assess short term and long term effects on cardiomyocytes. Since it is well established that certain pharmacological treatments and disease conditions can result in cardiac hypertrophy or atrophy culminating in changes in the morphology of cardiomyocyte, the systems and methods are able to precisely measure and quantify these changes in cell morphology and shape. Thus the methods and systems have particular utility in the areas of biomedical research.

In some embodiments, potential agents are tested to assess whether they are cardioprotective, or protect against adverse affects. In such embodiments the agent suspected of being cardioprotective is added to the cardiomyocytes prior to, simultaneously or after adding a cardiotoxic agent or a cardiotoxic event. Thus, a cardioprotective agent may prevent abnormal shifts in beating cycle, which would naturally occur in the presence of a cardiotoxic agent. In further embodiments, cardiomyocytes having abnormal beating cycles are treated with potential agents to assess whether normal beating may be induced, such as through administration of a cardioprotective pharmacological agent.

Certain treatments can also affect the differentiative process of ES cells to cardiomyocytes which may involve specific morphological and adhesive changes. In another aspect of the present invention a method is provide to screen or potential agents that may modulate the morphology of ES-derived cardiomyocyte, adult stem cell-derived cardiomyocyte or primary cardiomyocyte or its differentiation.

Impedance-based curves and optionally cell index curves may be used to calculate average rate of beats per unit time, average amplitude intensity in a unit time as well as the average length of time between the beats. Significant difference between measurements or data of a test well and a control well support a finding that the biologically active agent within the test well modulates cardiomyocyte function.

E. Assessing the Developmental or Functional Consequence of Gene Knockout and Transgene Expression in Embryonic Stem Cell-Derived Cardiomyocytes Embodiments of the present invention also include assessing the developmental consequence of genetically manipulated ES cells or their derived cardiomyocytes. ES cells offer a suitable experimental model system that is amenable to genetic manipulation. Therefore, specific genes can be targeted in knockout experiment as well as genes can be expressed in a developmental or stage specific manner under the control of special promoters. The impedance-based measurement system with millisecond time resolution can be used to evaluate the role of these genes in cardiac development and or function.

Steps involved in assessing the developmental and functional effect of gene knockout or transgene expression may include: obtaining ES cells harboring specific knockout of genes or which expresses a particular transgene; provide the system for monitoring impedance of excitable cells having millisecond time resolution; optionally coating wells of the device with either fibronectin or other matrix proteins; seeding the embryonic stem cells (ES cells) of mammalian origin at desired seeding densities into the wells of the device; allowing the cells to attach and spread; after a time period unique to ES-derived cardiomyocytes or primary cardiomyocytes, and monitoring cardiomyocyte beating using the impedance-monitoring system using millisecond kinetic readout to resolve the individual beat cycles of the cells. If a particular gene is required for development of cardiomyocytes from ES cells, it is likely that the knockout of that gene will either block or delay the differentiation of ES cells to cardiomyocytes. Since the impedance-based measurement system is capable of functional monitoring of cardiomyocyte, it can be used as a specific way to monitor the effect of either gene knockout or transgene expression on cardiomyocyte function. In alternative embodiments, the ES cells can be transfected with specific siRNA to "knockdown" the product of a particular transcript and then monitor cardiomyocyte differentiation and function in vitro using the impedance-based measurement system with millisecond time resolution.

In other exemplary embodiments an impedance-based measurement system is used to evaluate the role of genes in cardiac viability, morphology, development and or beating function. The steps involved in assessing the developmental and functional effect of gene knockout or transgene expression may include: obtaining ES cells harboring specific knockout of genes or which expresses a particular transgene; providing a single-well or multi-well device that comprise microelectrode arrays in well(s) of the device, which can be used for monitoring cell-substrate impedance; optionally coat wells of the device with either fibronectin or other matrix proteins; seeding the embryonic stem cells (ES cells) of mammalian origin or adult stem cells of mammalian origin at specific seeding densities to the wells of the device; allowing the cells to attach and spread and monitor the growth and viability of the cells using the impedance-based system; after a specified period of time unique to ES-derived cardiomyocytes or primary cardiomyocytes, monitoring cardiomyocyte beating using the impedance-monitoring system to monitor electrode impedance by using milli-second kinetic readout to resolve the individual beat cycles of the cells. If a particular gene is required for development of cardiomyocytes from ES cells, it is likely that the knockout of that gene will either affect the viability of the cells or block or delay the differentiation of ES cells to cardiomyocytes. Since the impedance-based measurement system is capable of functional monitoring of cardiomyocyte both in long term assays and short term assays, it can be used as a specific way to monitor the effect of either gene knockout or transgene expression on cardiomyocyte function. In related embodiments, the ES cells can be transfected with specific siRNA to "knockdown" the product of a particular transcript and then monitor cardiomyocyte viability, differentiation and function in vitro using the impedance-based measurement system.

In another exemplary embodiment, steps involved in assessing the developmental and functional effect of gene knockout or transgene expression using an impedance-based system in vitro are provided, which include: obtaining ES cells harboring specific knockout of genes or which expresses a particular transgene; optionally coating E-PLATES with either fibronectin or other matrix proteins; seeding either ES cells of mammalian origin or primary cardiomyocytes at specific seeding densities; allowing the cells to attach and spread; and after a specified period of time unique to ES-derived cardiomyocytes or primary cardiomyocytes, monitoring cardiomyocyte beating using the impedance-based system by using millisecond kinetic readout to resolve the individual beat cycles of the cells. If a particular gene is required for development of cardiomyocytes from ES cells, it is likely that the knockout of that gene will either block or delay the differentiation of ES cells to cardiomyocytes. Since the impedance-based system is capable of functional monitoring of cardiomyocyte, it can be used as a specific way to monitor the effect of either gene knockout or transgene expression on cardiomyocyte function. Alternatively, the ES cells can be transfected with specific siRNA to "knockdown" the product of a particular transcript and then monitor cardiomyocyte differentiation and function in vitro using the impedance-based system.

In another aspect, the present invention is directed to method to establish an assay to assess the effect of gene knockout or transgene expression in ES cells differentiated to cardiomyocytes and functionally monitored by the impedance-based system. The method includes providing a device for measuring cell-substrate impedance operably connected to an impedance analyzer, wherein the device includes at least two wells; adding wildtype ES cells as control to at least 1 well and ES cells with a gene knockout or a transgene in at least 1 other well; monitoring impedance of the at least two wells at time intervals over a period of time and optionally determining cell indices from impedance values; comparing the impedance-based curves or optionally the cell index curves between the control well and the well containing the ES cells harboring a knockout of a specific gene or expressing a specific transgene; and if significantly different, concluding that the gene knockout or the transgene can affect either cardiomyocyte viability, morphology from ES cells or cardiomyocyte function as monitored by observing the excitation-contraction coupling.

As above, in preferred embodiments, the time difference between two consecutive impedance measurement for a well is in the range of milliseconds (e.g., less than 500 milliseconds, less than 300 milliseconds, less than 100 milliseconds, less than 10 milliseconds, or less than about 1 millisecond or faster). The millisecond kinetic readout is required to resolve the individual beat cycles of the cells. Thus, the time resolution for the impedance measurement should allow the system to perform measurement using at least two time points for each beat cycle. In some embodiments more than two time points are resolved for each beating cycle.

EXAMPLES

Example 1

Impedance Monitoring of Attachment, Growth and Viability of Mouse ES Cell-Derived Cardiomyocytes Since isolated primary cardiomyocytes, ES-derived cardiomyocytes and adult stem cell-derived cardiomyocytes can be maintained in culture, these cells provide a desirable model system to study cardiomyocytes as well as cardiomyocyte modulation. The present example demonstrates the use of the ACEA RT-CES system to measure and monitor the attachment, growth and viability of mouse ES-derived cardiomyocytes which were seeded at different seeding densities.

Mouse ES cells were seeded at a density ranging from 3000 cells to 50,000 cells per well in E-PLATES (Acea Biosciences, San Diego, Calif.) precoated with fibronectin. The attachment, growth and viability of the cells were monitored on RT-CES system measuring impedance signal in the form of cell index every 30 minute for 48 hours. At about 48 hrs after cell seeding, the growth of the cells had ceased and the appearance of beating cardiomyocytes were evident as judged by looking at the cells inside the E-PLATE under the microscope.

Figure 3:
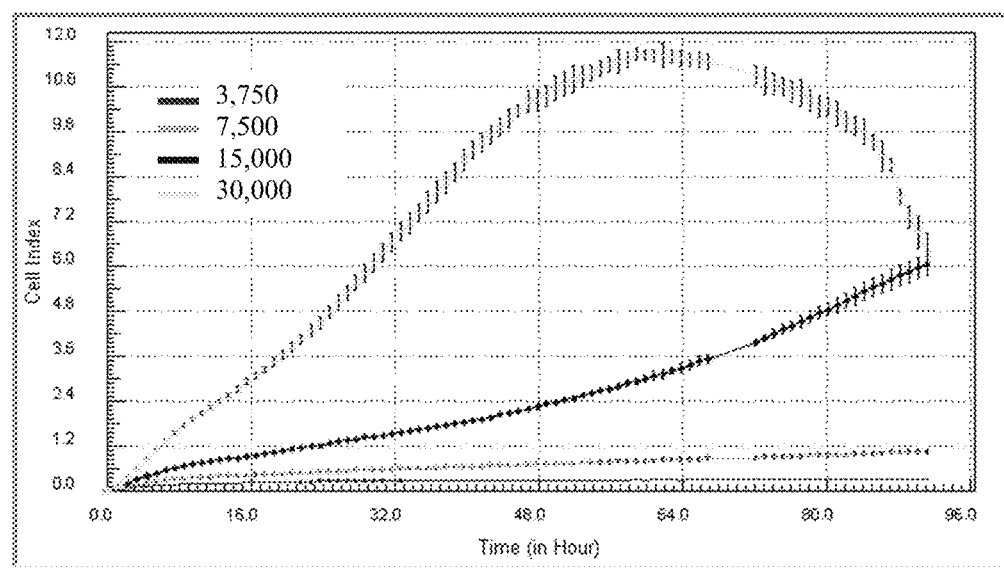
FIG. 3 shows the cell index curves measured on RT-CES system for 4 different seeding densities (3750, 7500, 15,000 and 30,000 cells per well) of mouse ES-derived cardiomyocytes. In this example, the impedance measurement was taken with a time resolution of 1 hour between any two consecutive data points for each well.

FIG. 3 shows the cell index curves measured on RT-CES system for 4 different seeding densities (3750, 7500, 15,000 and 30,000 cells per well) of mouse ES-derived cardiomyocytes. For such long term measurement, cell electrode impedance and corresponding cell indices were measured at about 15 minute intervals. Based on the cell index growth and viability curves, it is evident that the extent of the impedance signal correlates well with the seeding density of viable ES-derived cardiomyocytes.

Example 2

Detection of Cardiotoxic Effects Using Real Tim Impedance Monitoring

Figure 4A:
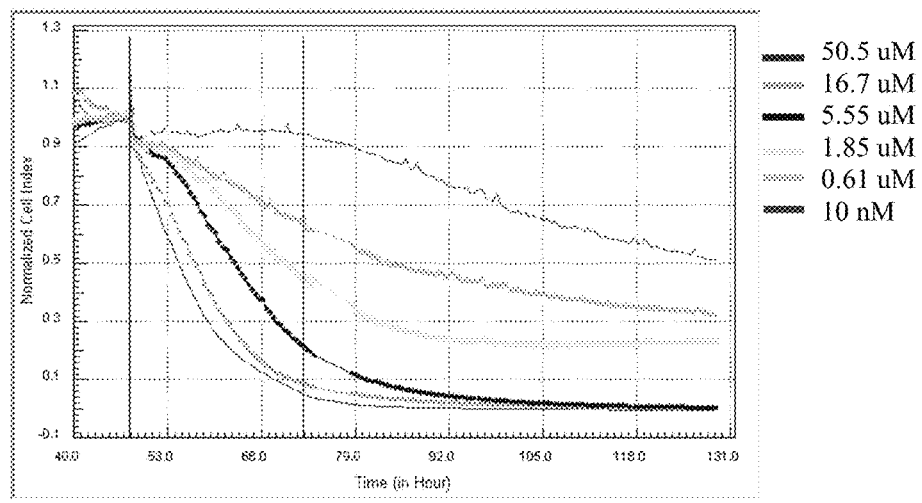
FIG. 4A provides a plot of normalized cell index values for cells in different wells treated with different concentrations of sodium dichromate dehydrate (SDD).
Figure 4B:
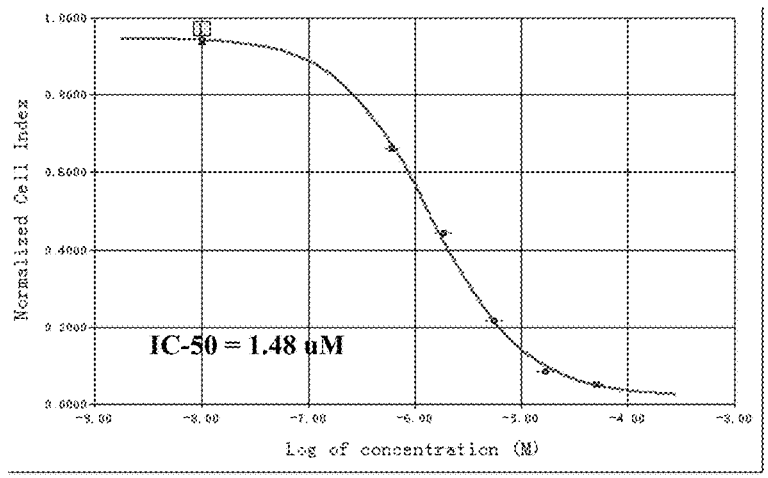
FIG. 4B provides the corresponding sigmoidal curve for deriving the IC-50 of the compound.

As an example, we describe here the use of the ACEA RT-CES system to measure and monitor the attachment and growth of mouse ES cells derived cardiomyocytes and subsequently treated with a cytotoxic agent (FIG. 4).

Mouse ES-derived cardiomyocytes were seeded at a density of 25,000 cells per well in E-PLATES precoated with fibronectin. The attachment and growth of cells were monitored on RT-CES system for 72 hours and then treated with increasing doses of the compound of sodium dichromate dehydrate which is known to induce cytotoxicity. According to FIG. 4A the plot of normalized cell index for cells in different wells treated with different concentrations of sodium dichromate dehydrate (SDD), SDD causes a concentration dependent decrease in viability of ES-derived cardiomyocytes. To quantify the extent of sodium dichromate dehydrate activity against the cardiomyocytes, the normalized cell indices at 24 hrs after compound treatment were plotted against the log of the corresponding sodium dichromate dehydrate concentrations. From the sigmoidal curve, shown in FIG. 4B, half maximal activity or IC-50 value of 1.48 uM was derived for the compound.

Example 3

Figure 5A:
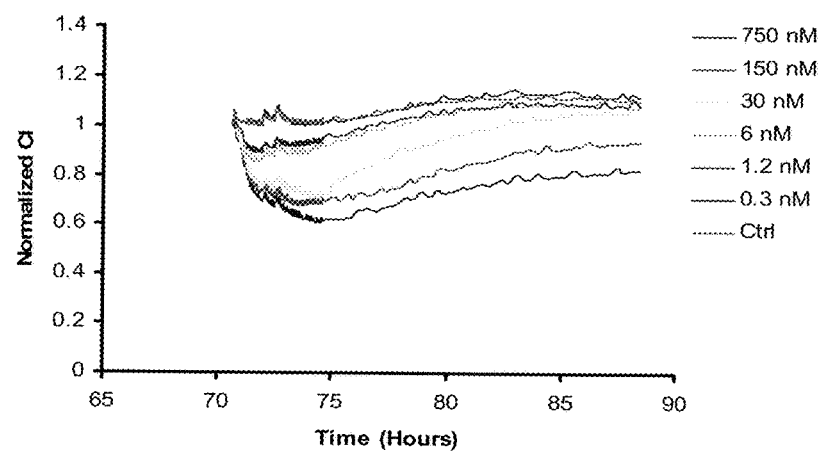
FIG. 5A provides a graph of normalized impedance data over time showing shifts in morphology in response to isproteranol, a β2 adrenergic receptor agonist.

Real Time Monitoring of Mouse ES Cell-Derived Cardiomyocytes and Inducing Hypertrophy As an example, we describe here the use of the ACEA RT-CES system to measure and monitor the attachment and growth of mouse ES cells derived cardiomyocytes and subsequently treated with isoproteranol, a β2 adrenergic receptor agonist known to induce hypertrophy (FIG. 5A).

Figure 5B:
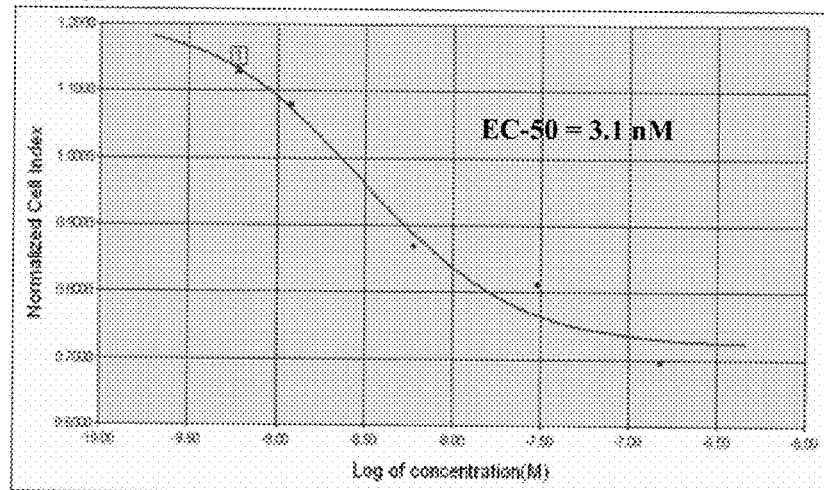
FIG. 5B shows a plot of the normalized cell indices against the log of the corresponding isoproteranol concentrations to calculate the EC-50.

Mouse ES-derived cardiomyocytes were seeded at a density of 25,000 cells per well in E-PLATES precoated with fibronectin. The attachment and growth of the cells were monitored on RT-CES system for 72 hours and then treated with increasing doses of the compound isoproteranol. According to FIG. 5A, isoproteranol causes a concentration dependent change in cell index readings. The timing of the cell index change is consistent with a change in the morphology of the cells which we have shown previously for other GPCR agonists in primary cells (Yu et al (2006): Real-time monitoring of morphological changes in living cells by electronic cell sensor arrays: an approach to study G protein-coupled receptors; Analytical Chemistry, Vol 78, pages 35-43). To quantify the extent of isoproteranol-induced morphological changes in mouse ES-derived cardiomyocytes, the normalized cell indices were plotted against the log of the corresponding isoproteranol concentrations (FIG. 5B). From the sigmoidal curve generated a half maximal activity or IC-50 value of 3.1 nM was derived for the compound.

Example 4

Real Time Impedance Monitoring with Millisecond Resolution of Beating Cardiomyocytes As an example, we describe here the use of an improved impedance-based system with millisecond time resolution to measure and monitor the beating of cardiomyocytes using fast kinetic software.

Figure 6:
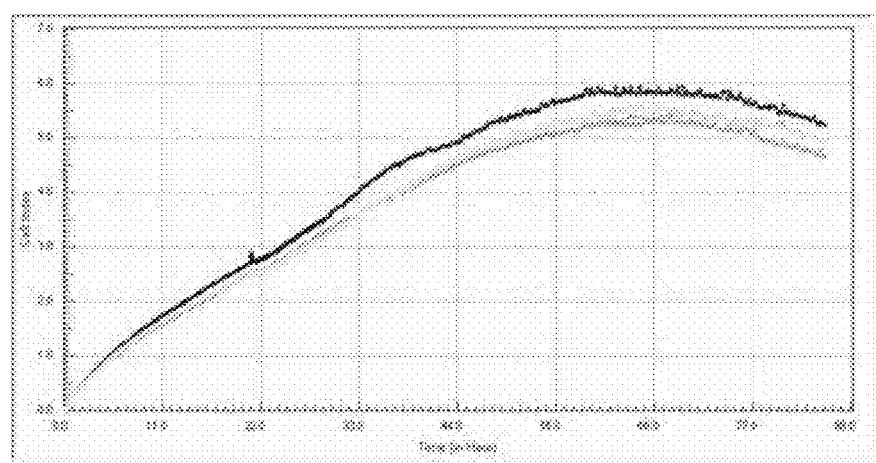
FIG. 6 shows the cell index curves measured on RT-CES system for 4 individual wells, with cell culture medium as background starting from cell seeding to about 86 hrs after cell seeding. For such long term measurement, cell electrode impedance and corresponding cell indices were measured at about 15 minute intervals. Thus for each well, the impedance measurement was performed with a time resolution of 15 minutes.

Mouse ES cells were seeded at a density of between 3,000 to 50,000 cells per well in E-PLATES precoated with fibronectin. The attachment and growth of the cells were monitored on RT-CES system. FIG. 6 shows the cell index curves measured on RT-CES system for 4 individual wells, with cell culture medium as background starting from cell seeding to about 86 hrs after cell seeding. For such long term measurement, cell electrode impedance and corresponding cell indices were measured at about 15 minute intervals. As evidenced on these plots, the cell index curves were rather smooth up to about 44-48 hrs, after which there were "noises" or "small-spikes" on the cell index curves. Such spikes were most evident after about 60 hrs. We now understand the origins of such "small-spikes" and interpret that such spikes in the impedance or cell index readout are associated with the beating of the cells. During the synchronized beating of the cells, the cell morphology and cell adhesion/attachment to the electrodes change regularly in synchrony with the cell beating. Such regular or periodic changes in cell morphology and cell adhesion/attachment are then reflected in the changes in cell-electrode or cell-substrate impedances.

Figure 7A:
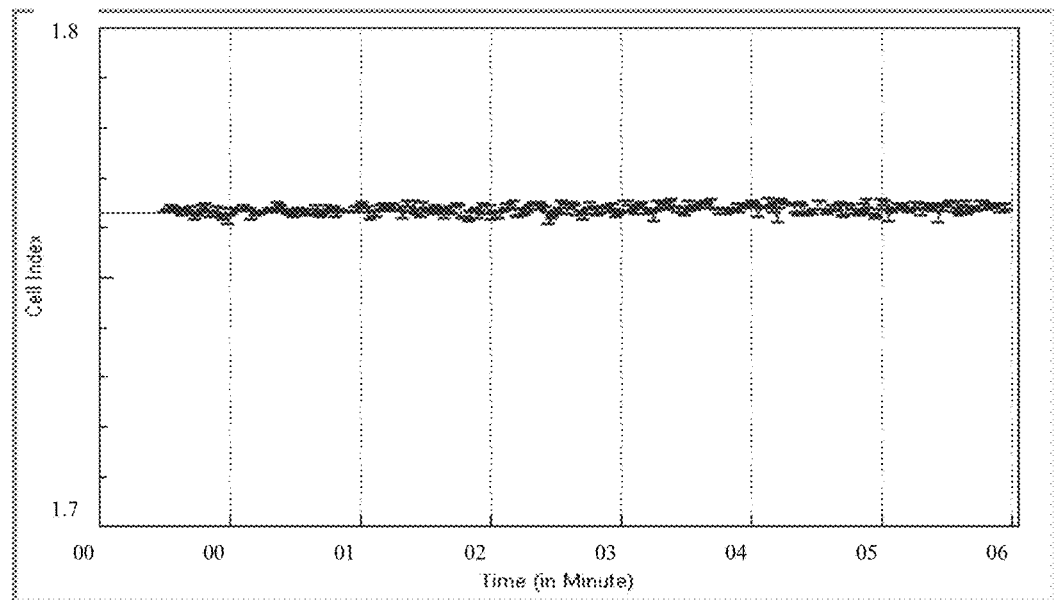
FIGS. 7A-D provides a series of graphs showing cardiomyocyte beating throughout attachment and growth phases.
Figure 7B:
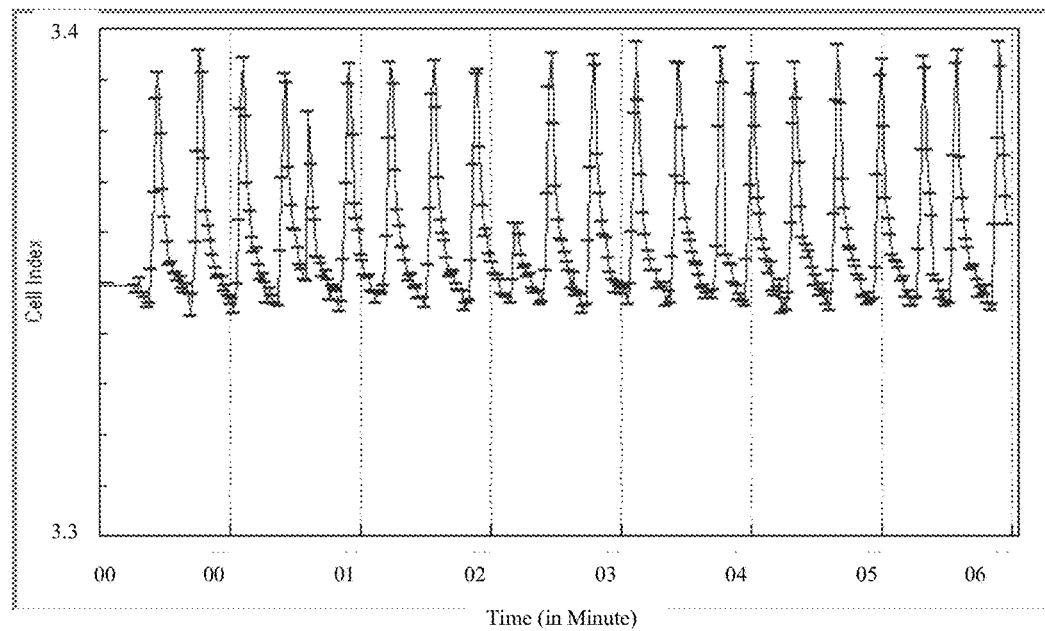
Figure 7C:
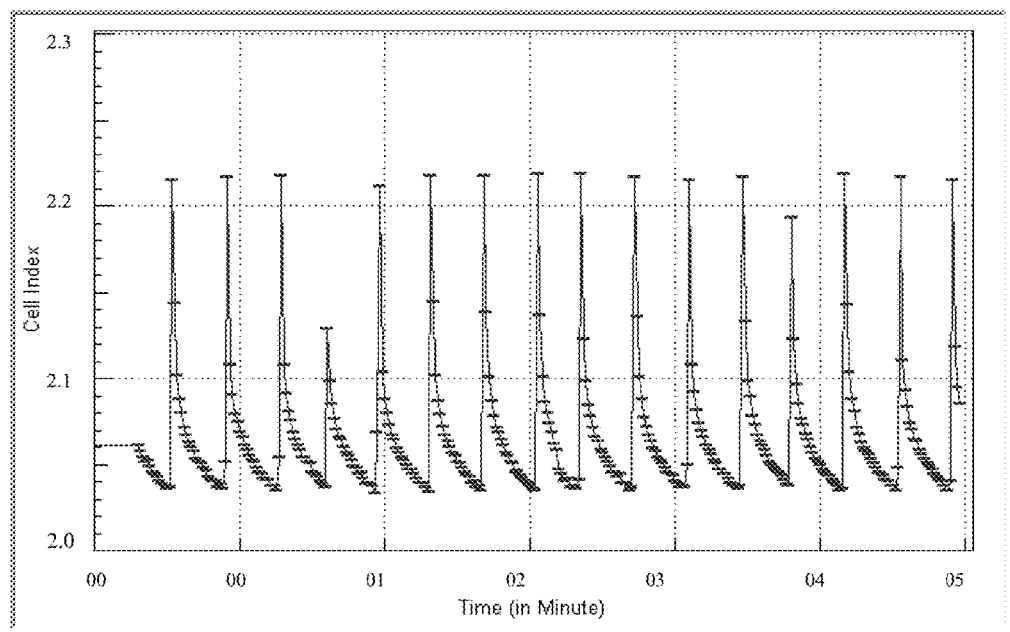
Figure 7D:
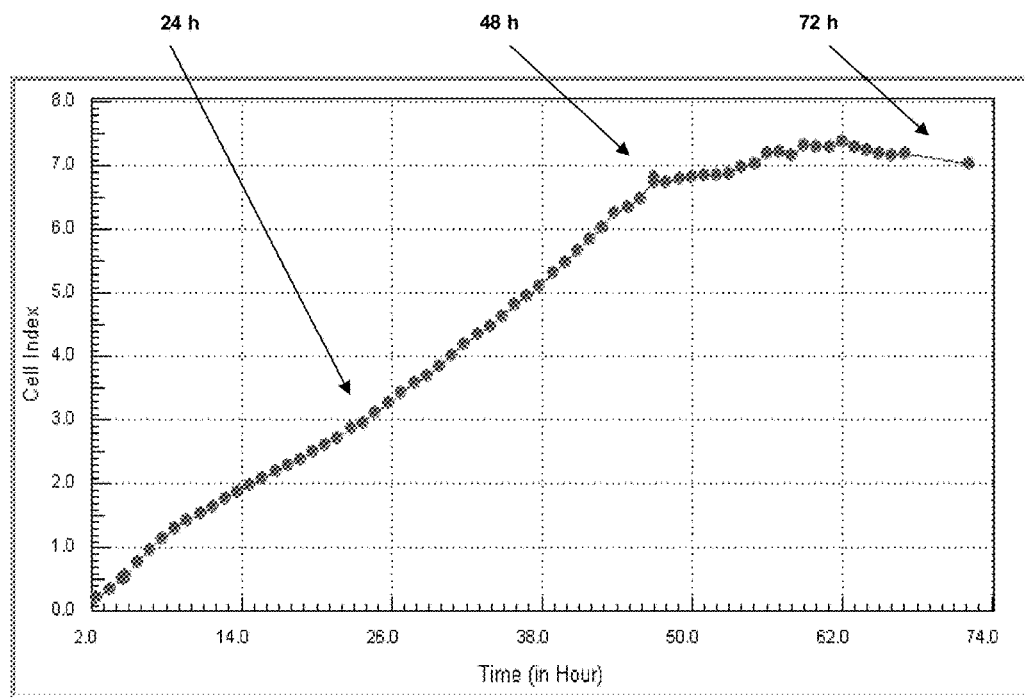

In order to monitor beating of cardiomyocytes, a specially designed software and measurement circuit hardware that are capable of millisecond impedance data acquisition (e.g., typically with time resolution between consecutive impedance measurement for a same well being less than 40 milliseconds) was used to monitor the quick rhythmic beating of the cardiomyocytes. For such measurement, the background electrode impedance is measured with the cells inside the wells (note, this is in contrast with FIGS. 3 and 6, where the background measurement is performed using cell culture media). The software was used to measure cardiomyocyte beating at distinct stages throughout its attachment and growth phases (FIG. 7). For a baseline reference, the impedance measurement was done on the ES cells at 24 hours where the cells had not fully spread and formed a tight monolayer and even though the cells appear to beat when visualized under a microscope, they do so asynchronously and as a result no net beating signal is detected (FIG. 7A). For plot, impedance readout has been converted into dimensionless cell indices. FIGS. 7B and 7C shows that ES cells that had fully spread and formed tight junctions with neighboring cells at 48 hours and 72 hours respectively, show regular impedance-spikes which correlate with the beating frequency of cardiomyocytes as judged by microscopic observation.

To use the measured cell index curves, it is important to further derive various physiologically relevant parameters. Several important parameters may include, the beating rate of the cardiomyocytes (i.e., how many times the cells beat within a unit of time for example, a minute), the beating amplitude (i.e. the magnitude of the beating of cells in terms of impedance change) the average amplitude intensity in a unit time as well as the average length of time between the beats, time of rise for a beat, time of decay for a beat. Because of the unique and complex nature of the impedance readout signals (smaller signal amplitude, sampling time resolution may be limited by the hardware and the software used), appropriate methods or techniques are required for analyzing cell index curves to derive the above mentioned parameters.

For deriving the beating rates of cardiomyocytes, one method may be by counting how many peaks there are within a given time frame (for example, one minute). For this approach to work, the sampling time resolution has to be sufficiently high so that the each beat of the cells does show a peak on the recorded cell index curves. In addition, determining a peak "automatically" also require some algorithm. For example, each peak would have to have one "rise" in cell index and also one "decay" in cell decay. Each "rise"-and-"decay" pair forms a single peak. The algorithm needs to determine such "rise" and "decay" portions of the curves and then counts a peak.

Figure 8A:
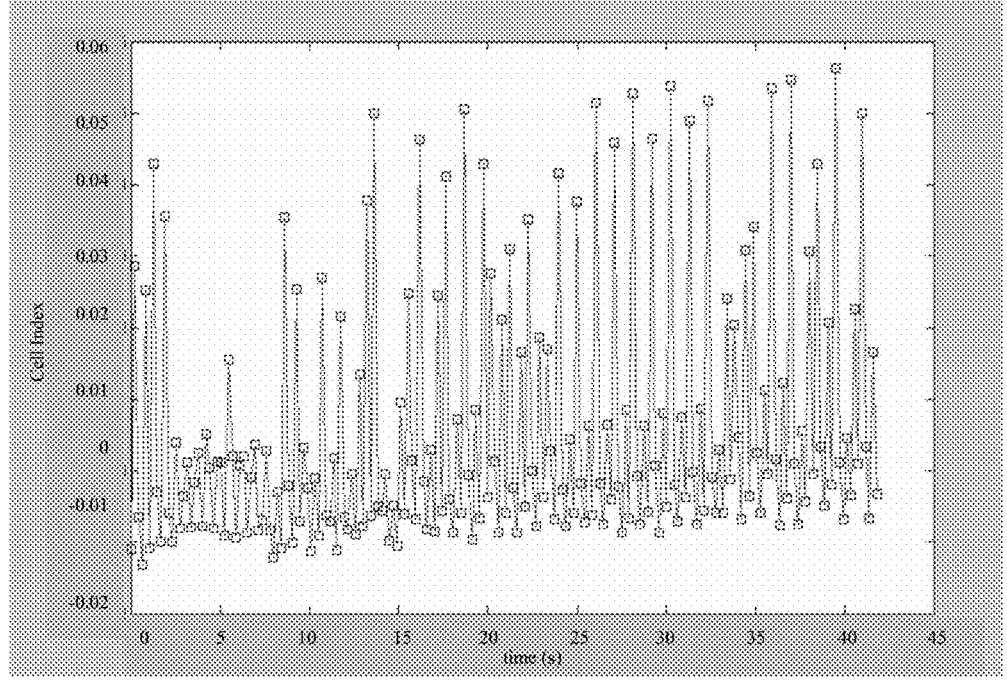
FIG. 8A and FIG. 8B are a pair of cell index curves and the corresponding beat rate derived from Fourier transformation of impedance values
Figure 8B:
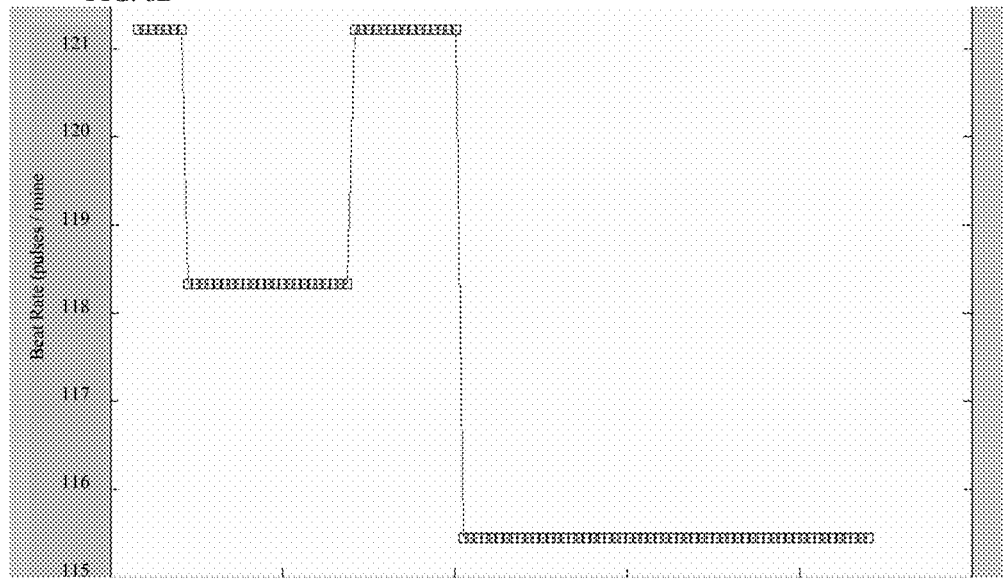

Another method to derive or count the beating rates of cardiomyocytes is to perform a detailed signal analysis to derive the frequency components of the cell index curves and to derive the magnitude of each frequency components. One method of signal analysis is Fourier transform of the cell index curve (of the time domain). Like above method, the sampling time-resolution needs to be sufficiently high so that each beat of the cells has at least three time points being measured. After performing Fourier transform, we would look for the frequency components having the largest magnitude and such frequency would correspond to, or be very close to, the beating frequency. In addition, for such analysis, giving a fixed sampling time resolution, the more time points sampled for analysis, the more accurate it is for the analyzed beating frequency. FIG. 8A and FIG. 8B shows a pair of cell index curves and the corresponding beat rate based the above described Fourier transform. In FIG. 8B, the cell index curves last from time zero to time 42 seconds. In FIG. 8B, the beating frequency for the traces in FIG. 8A is analyzed using the method described here, i.e., Fourier transform followed by picking up the highest-magnitude frequency component. For each derived frequency data at one time moment in FIG. 8B, cell index data from multiple time points (starting from previous 98 time points plus the time moment of interest) is used for analysis. Thus, the time axis in FIG. 8B starts from about 20 seconds to 42 seconds.

Figure 9A:
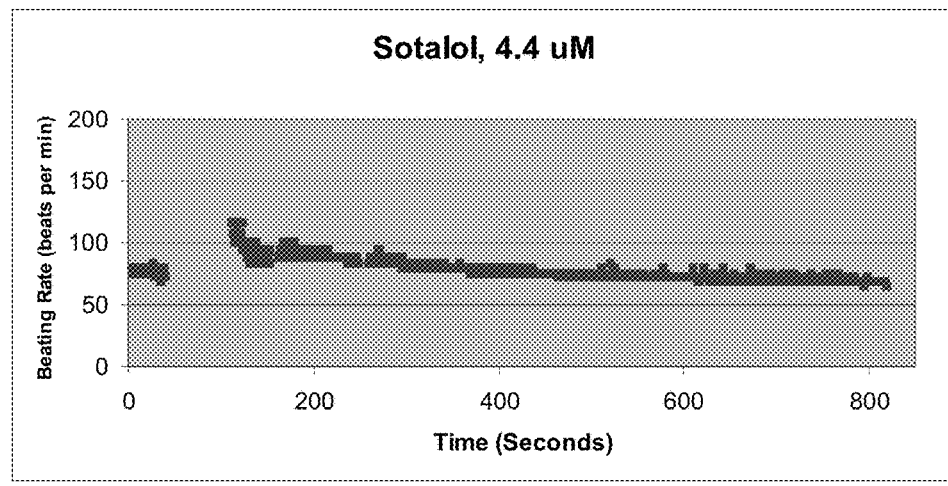
FIGS. 9A-D show cardiomyocyte beating data from mouse cardiomyocytes treated with sotalol.
Figure 9B:
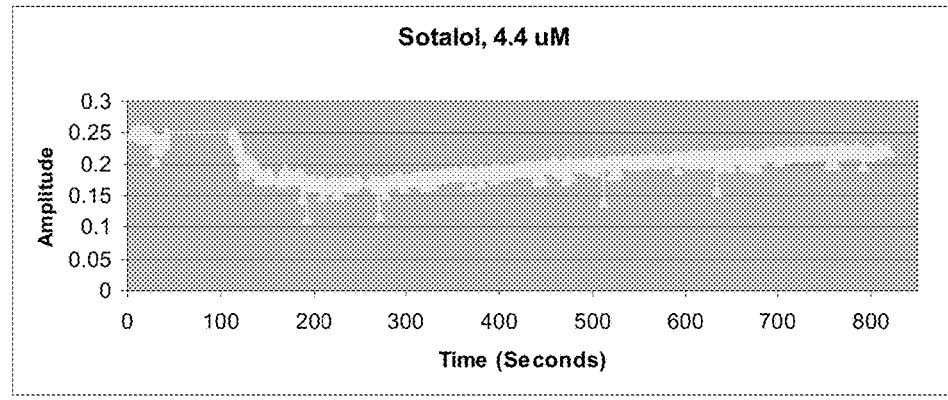
Figure 9C:
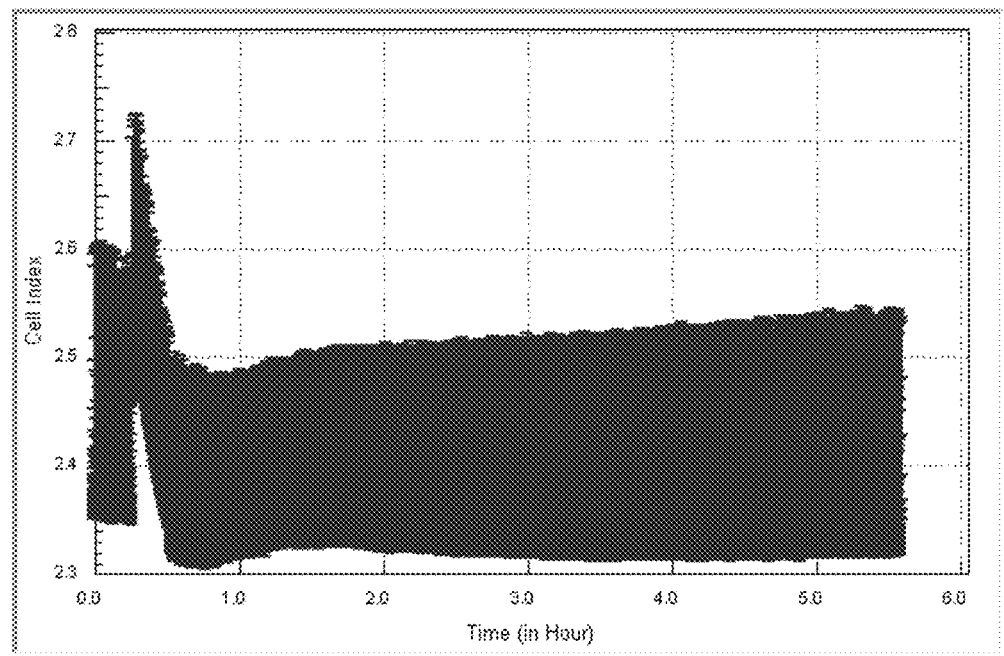
Figure 9D:
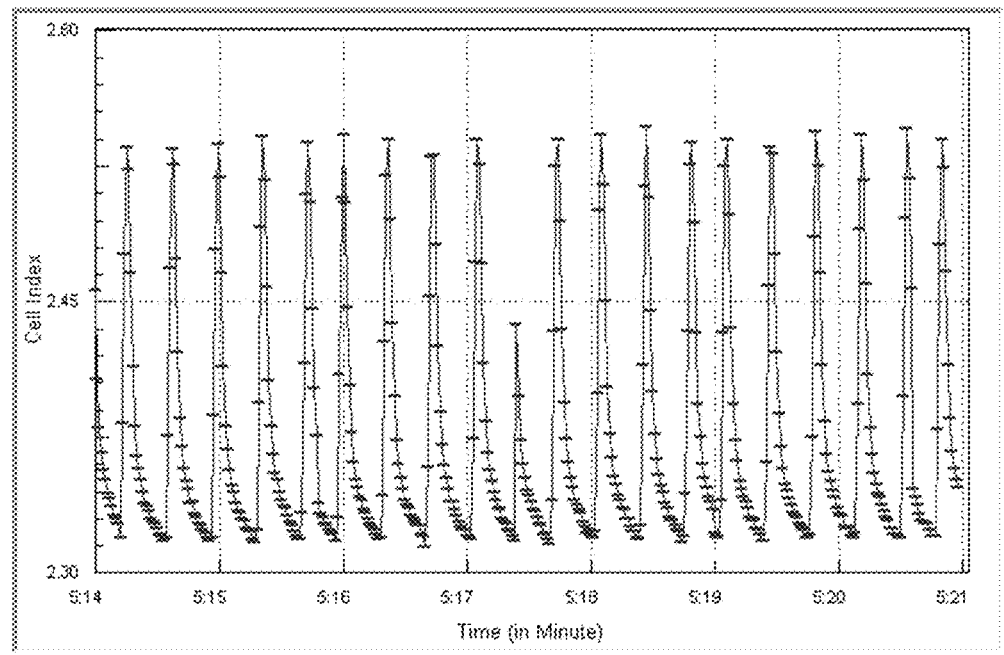

Another method deriving the beating rates of cardiomyocytes is to first determine the time length (AT in seconds) between two consecutive peaks and then calculate the beating rate according to the formula of "beats per minute=60/ΔT". Thus for each two-consecutive peaks, one can calculate one beating rate. Furthermore, one can plot this beating rate as a function of the time (of the first of the two consecutive peaks) to obtain the time dependency of the beating rates. FIG. 9A shows an example of the time-dependent beat rates derived using this method, for mouse ES-derived cardiomyocytes treated with compound sotalol at a concentration of 4.4 uM. Corresponding cell index data is shown in FIGS. 9C and 9D, where the time resolution between two adjacent points is 40 milliseconds. In other words, a second in FIGS. 9C and 9D is equivalent to 40-milliseconds.

For deriving the amplitude of the beating of the cardiomyocytes, there may also be different methods. One method is to analyze each peak and finding the peak maximum and the peak minimum. The amplitude is calculated by subtracting peak maximum by the peak minimum. Then, one can plot the peak amplitude as a function of the time of the peak to obtain the time dependency of the peak amplitude. FIG. 9B shows an example of the time-dependent peak amplitudes derived using this method, for mouse ES-derived cardiomyocytes treated with compound sotalol at a concentration of 4.4 uM. Another approach may also be to use Fourier transform described above. Then based on derived Fourier coefficients, one can re-simulate time domain cell index curves and look for the peak magnitude from the simulated curves.

For deriving the averaged length of time between the beats, there may also be different methods. For each identified peak, one can first determine a starting point of the peak. Then the time difference between two consecutive peaks at the two starting points of the peak can be used for the length of time between the beats.

With the method of determining each peak, one can also calculate the time-of-rise of the peak and the time-decay-of the peak.

Example 5

Identifying Modulators of Cardiac Function Using Real Time Impedance Monitoring with Millisecond Resolution Similar to Example 4, the millisecond kinetic readout requires that the impedance measurement system can provide impedance measurement data at millisecond time resolution. In other words, the time difference between two consecutive impedance measurement for a well shall be in the range of milliseconds (e.g., less than 500 millisecond, less than 300 millisecond, less than 100 millisecond, less than 10 millisecond, or less than 1 millisecond or faster). The millisecond kinetic readout is required to resolve the individual beat cycles of the cells. Thus, the time resolution for the impedance measurement should allow the system to perform measurement at least two time points for each beat cycle, or at more than two points for each beat cycle.

Figure 10A:
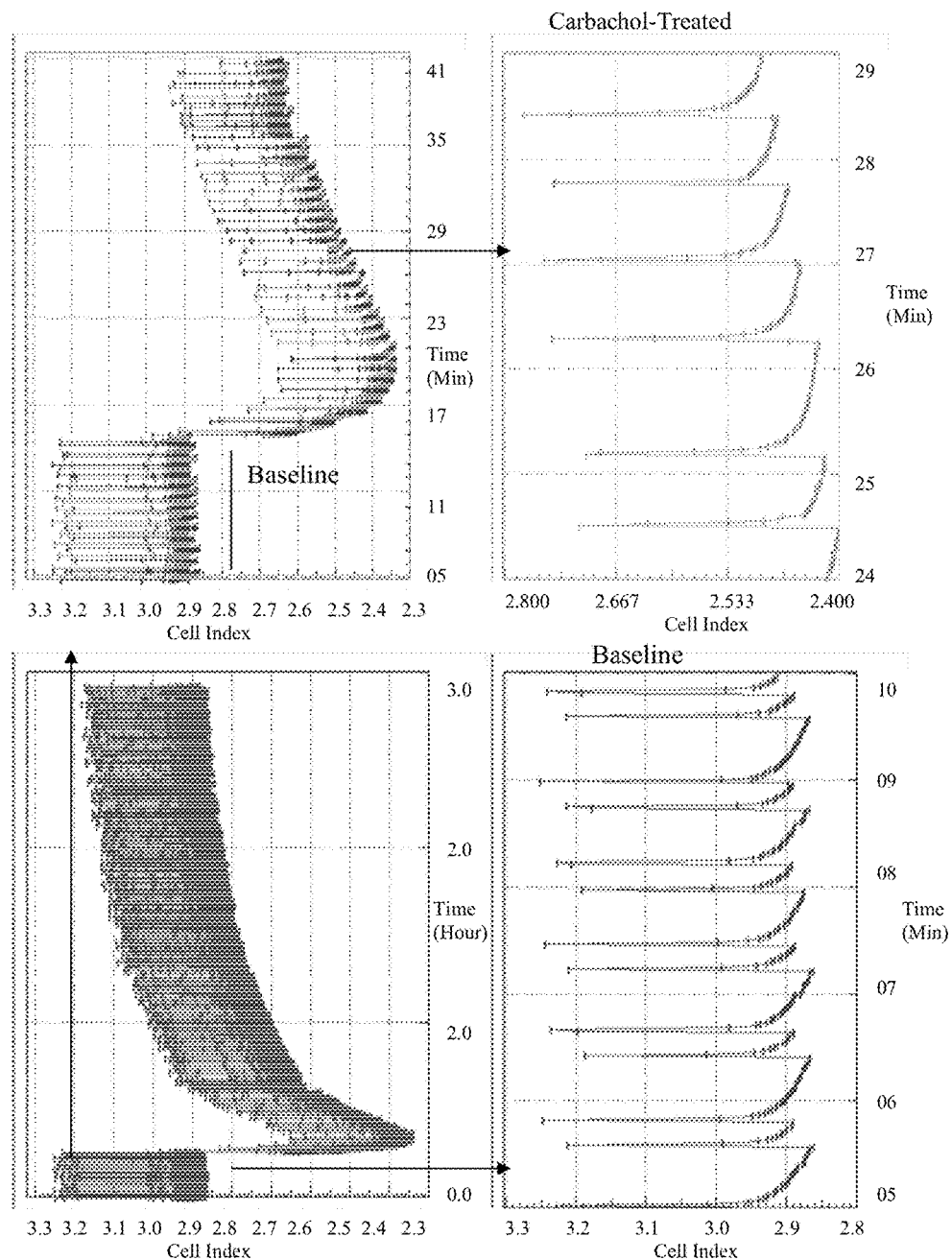
FIG. 10A depicts graphs of agents which slow down heart rate and cardiomyocyte beating.
Figure 10B:
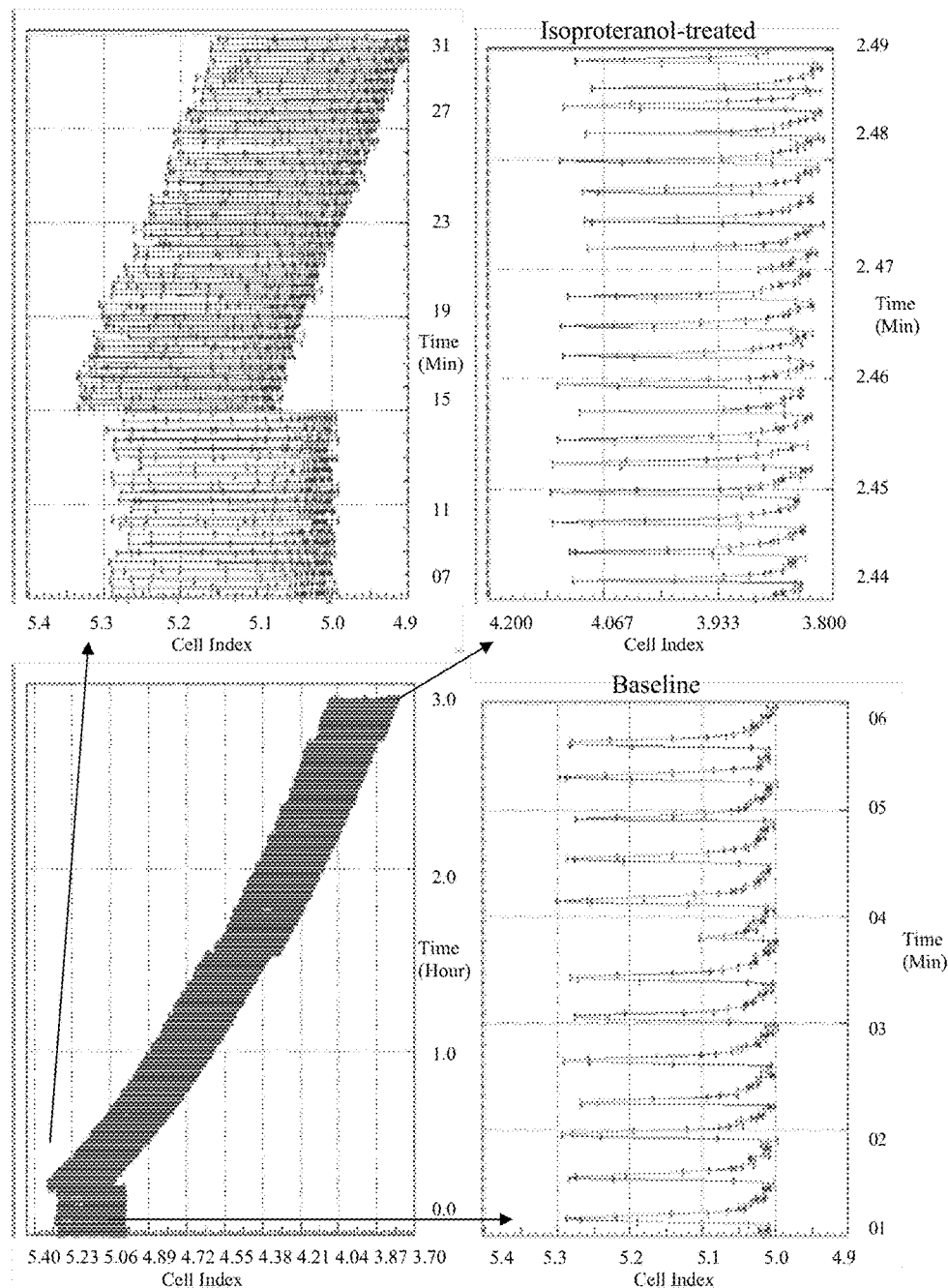
FIG. 10B depicts graphs of agents which increase heart rate and cardiomyocyte beating.
Figure 11A:
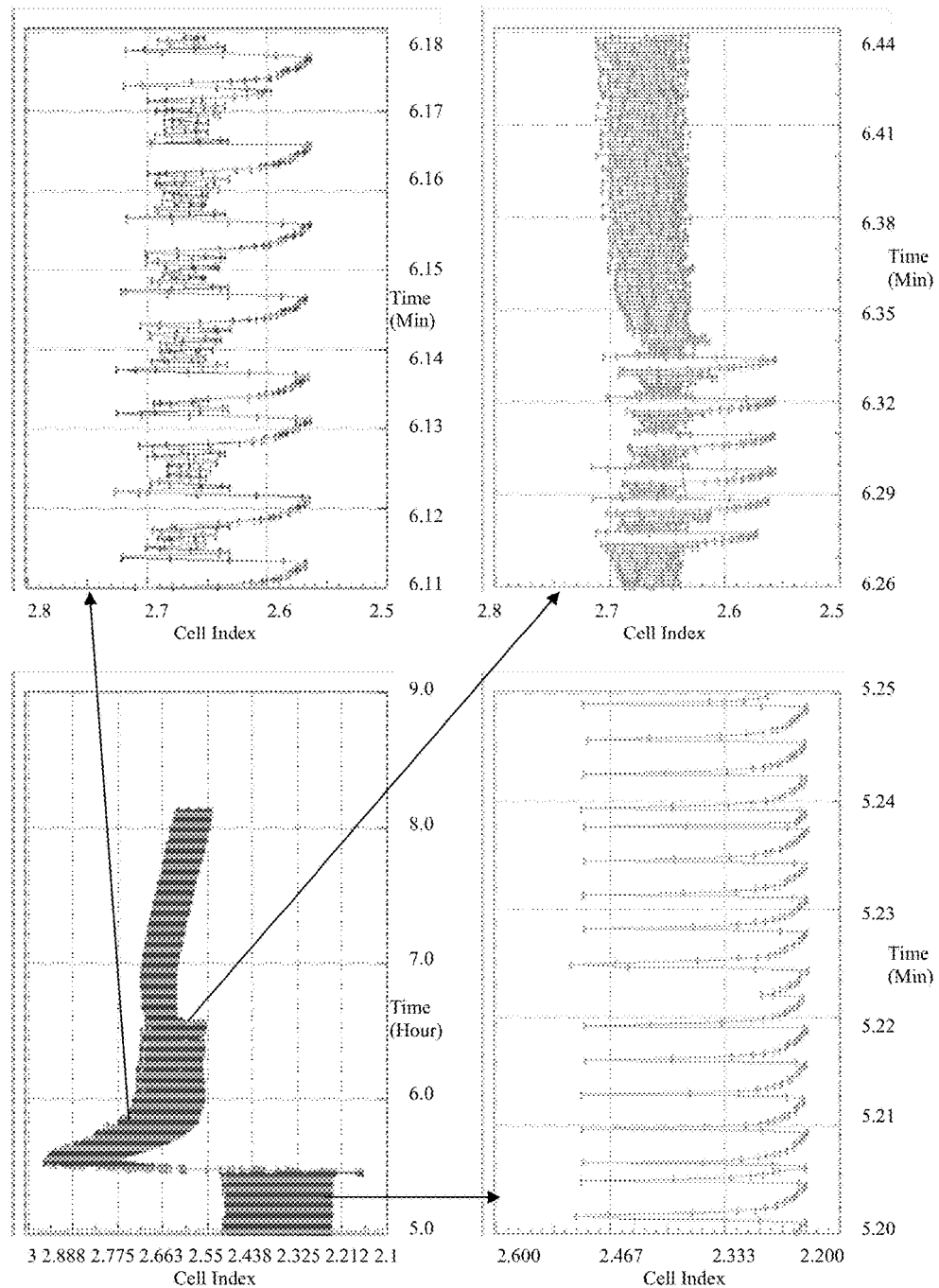
FIGS. 11A-S depict impedance data of cardiomyocyte patterns associated with testing of a variety of known compounds, which are further described in Table II.
Figure 11B:
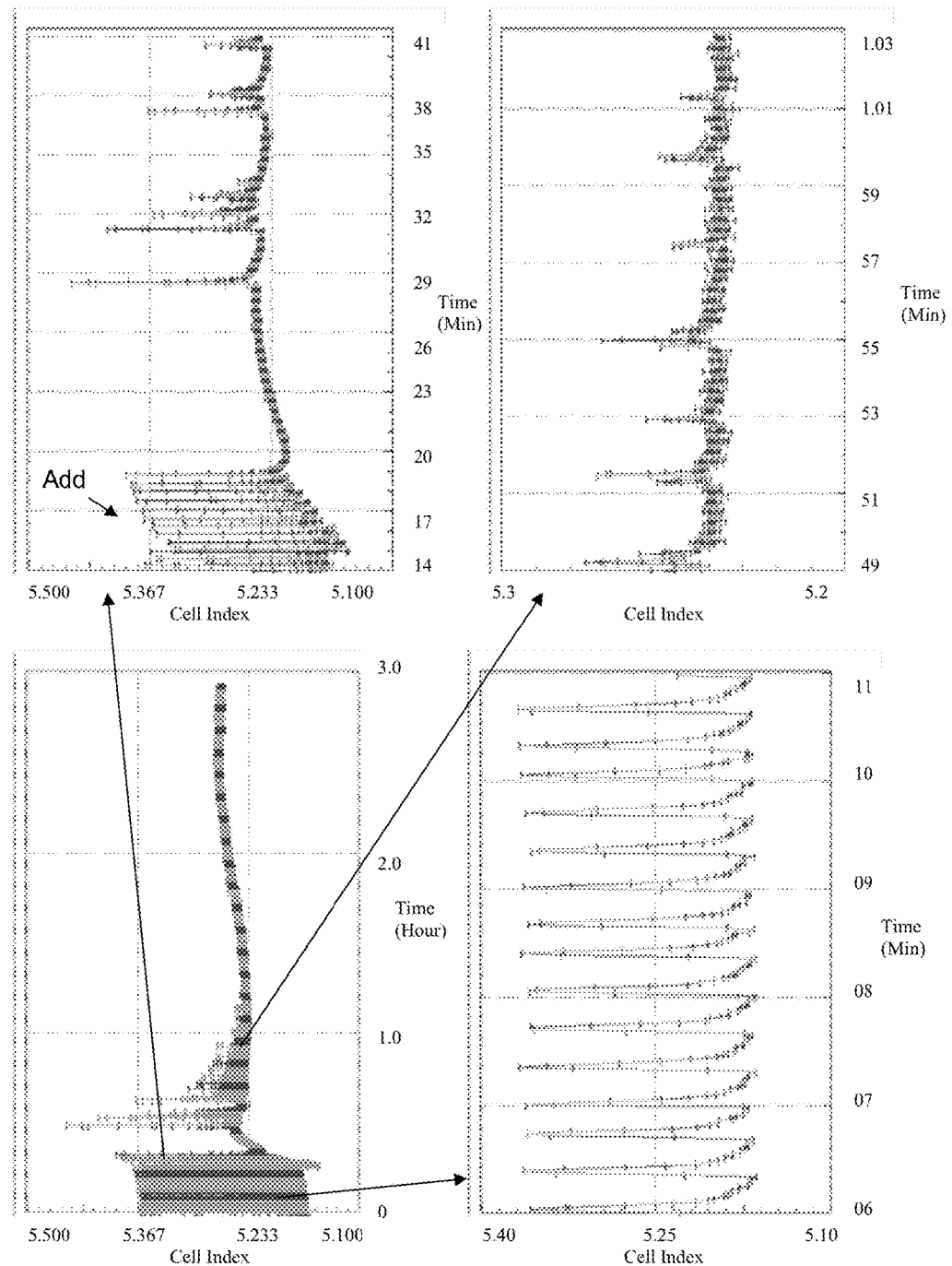
Figure 11C:
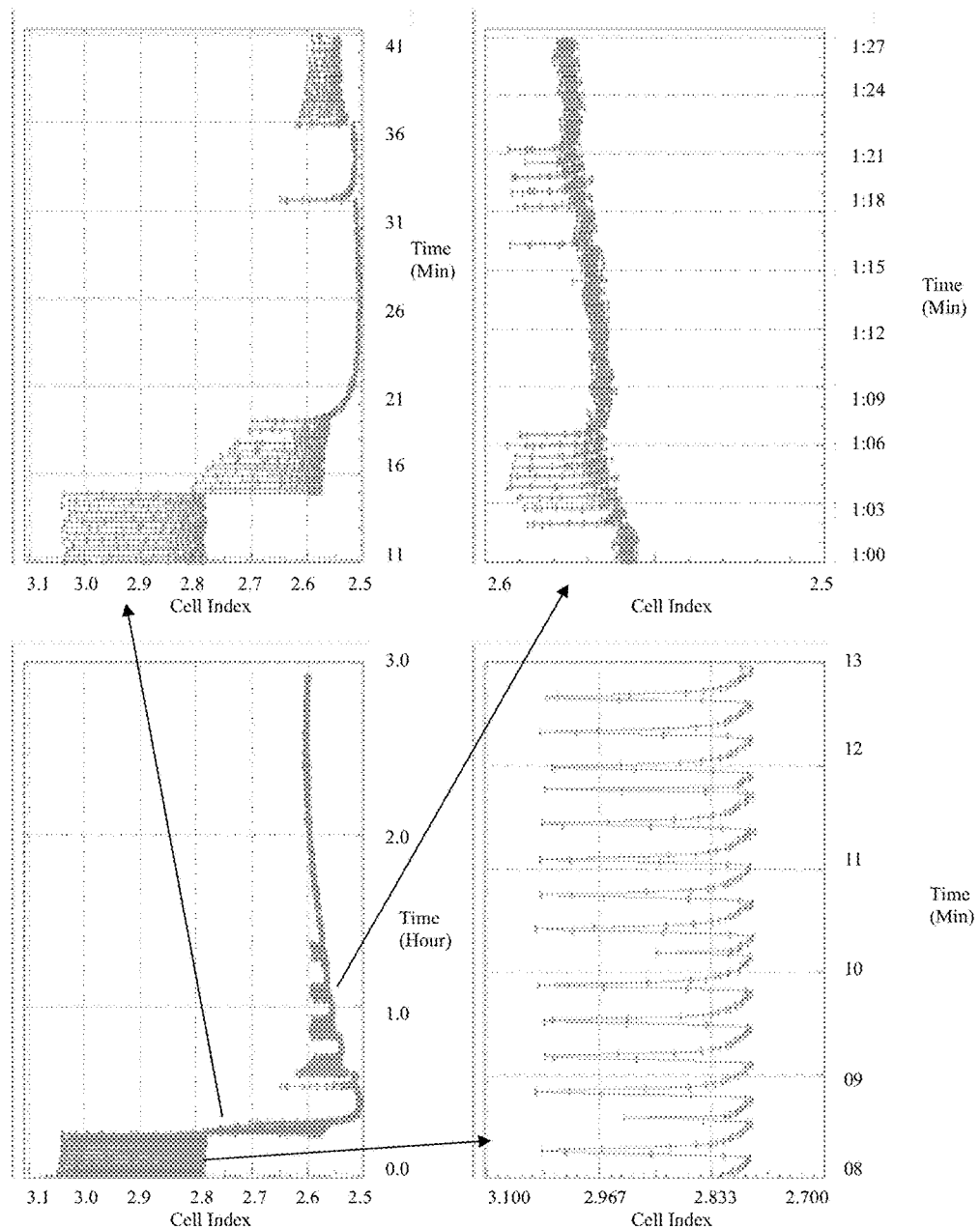
Figure 11D:
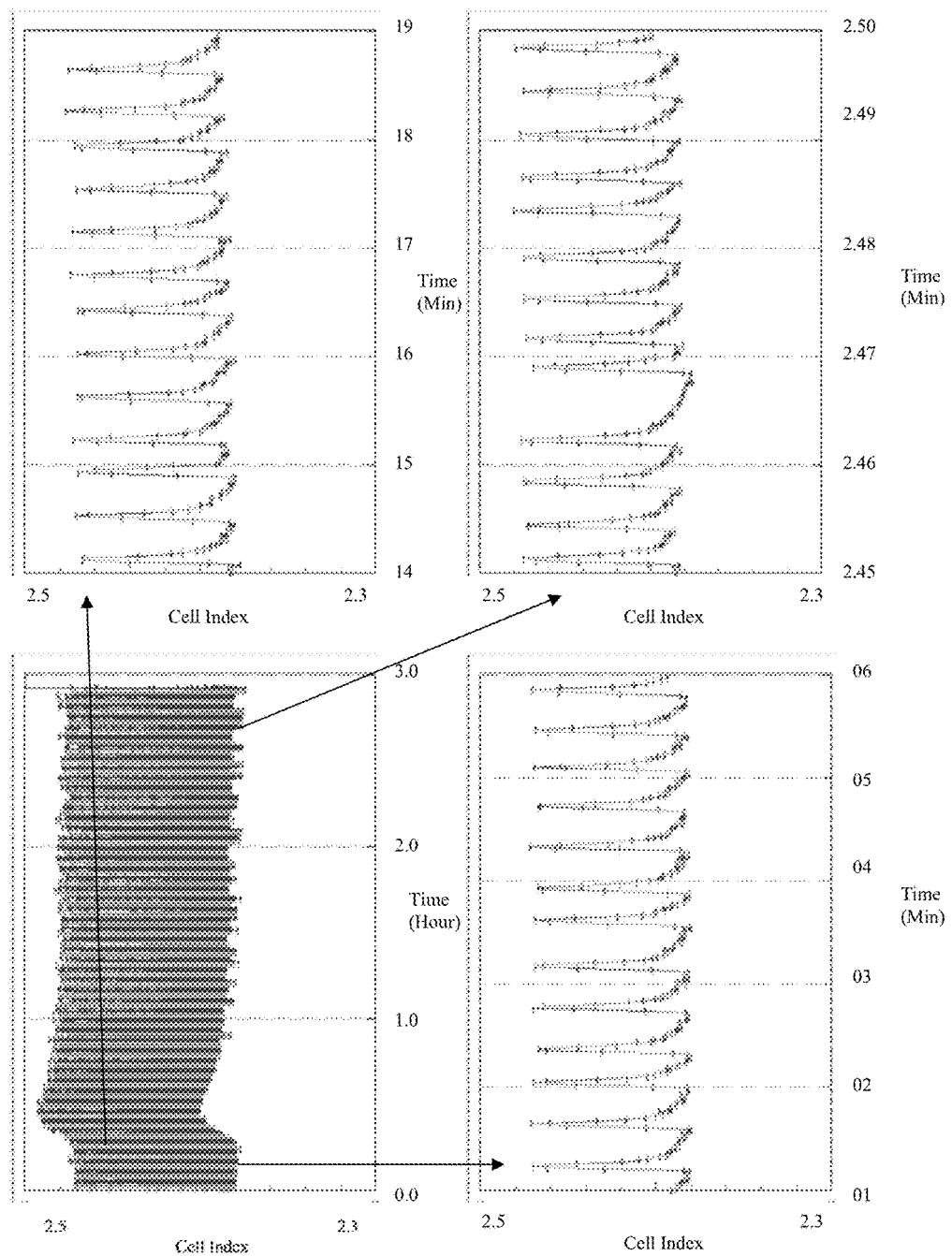
Figure 11E:
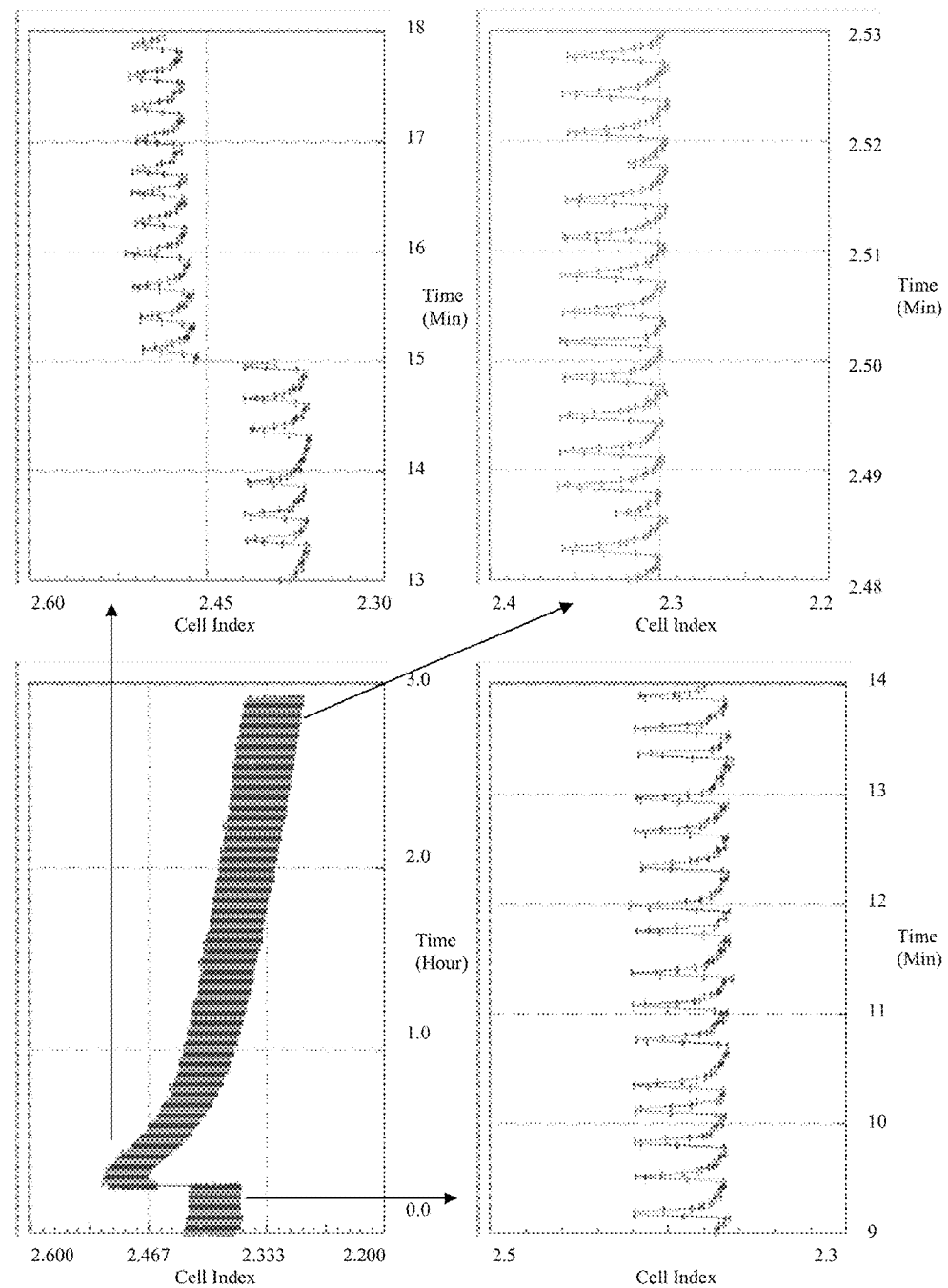
Figure 11F:
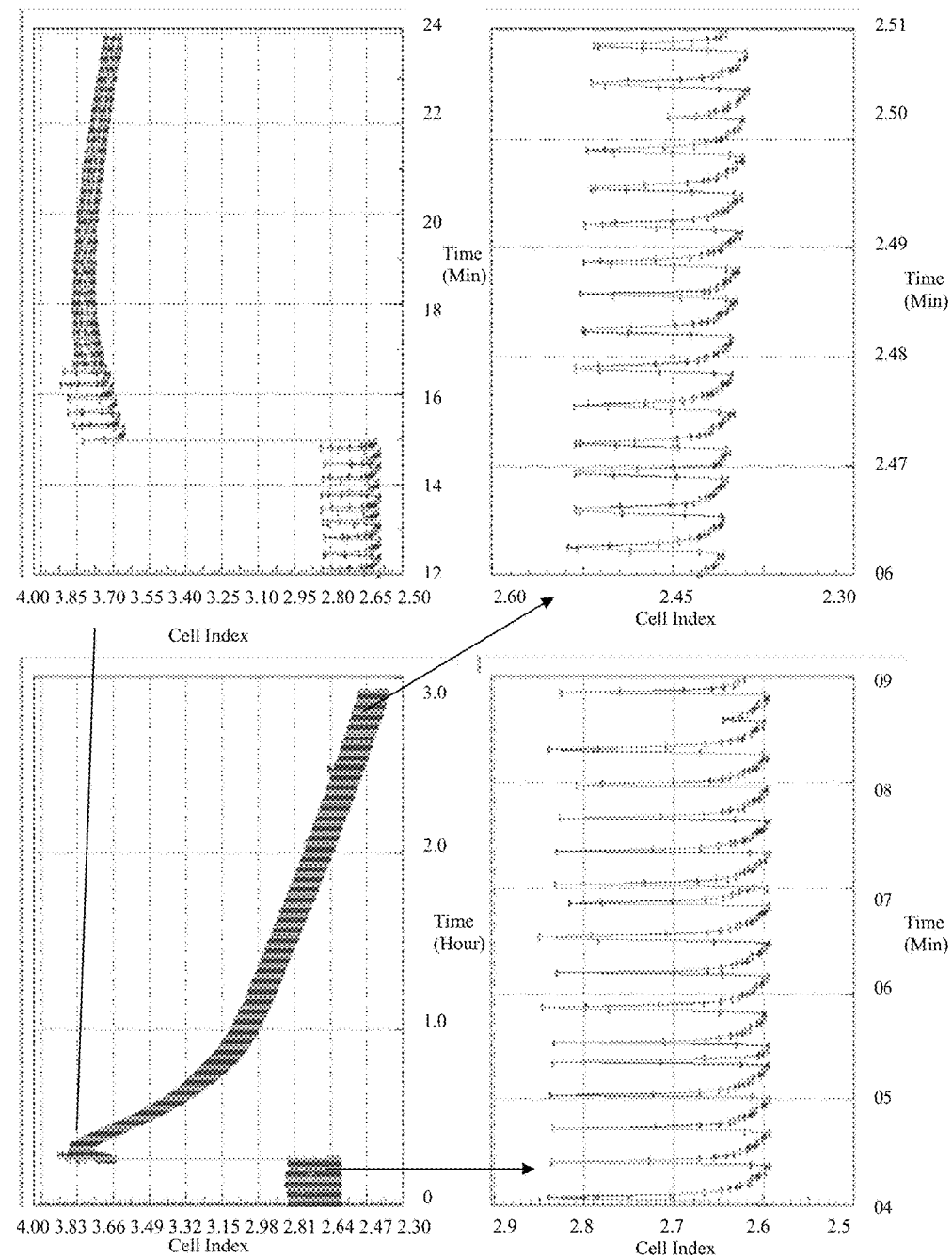
Figure 11G:
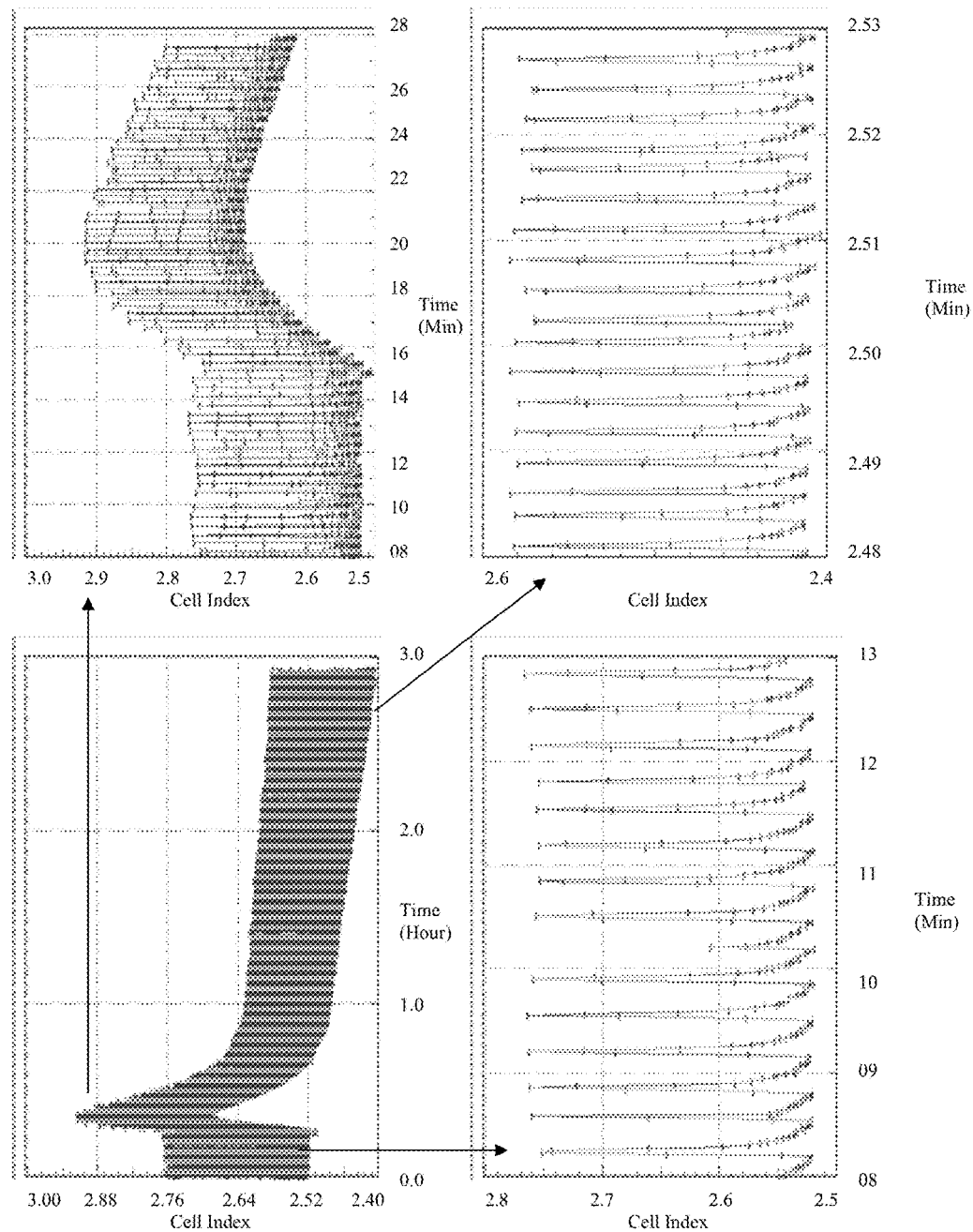
Figure 11H:
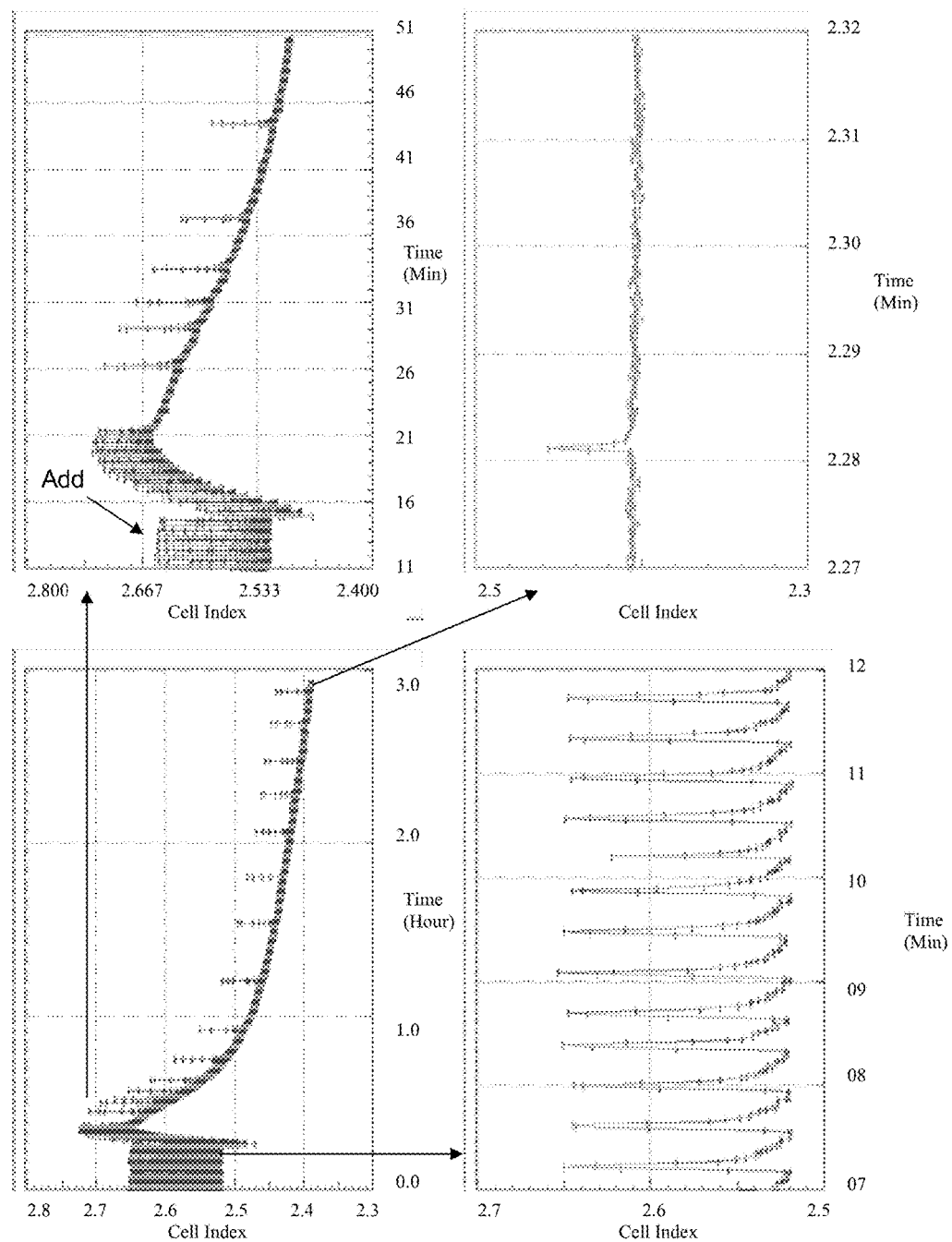
Figure 11I:
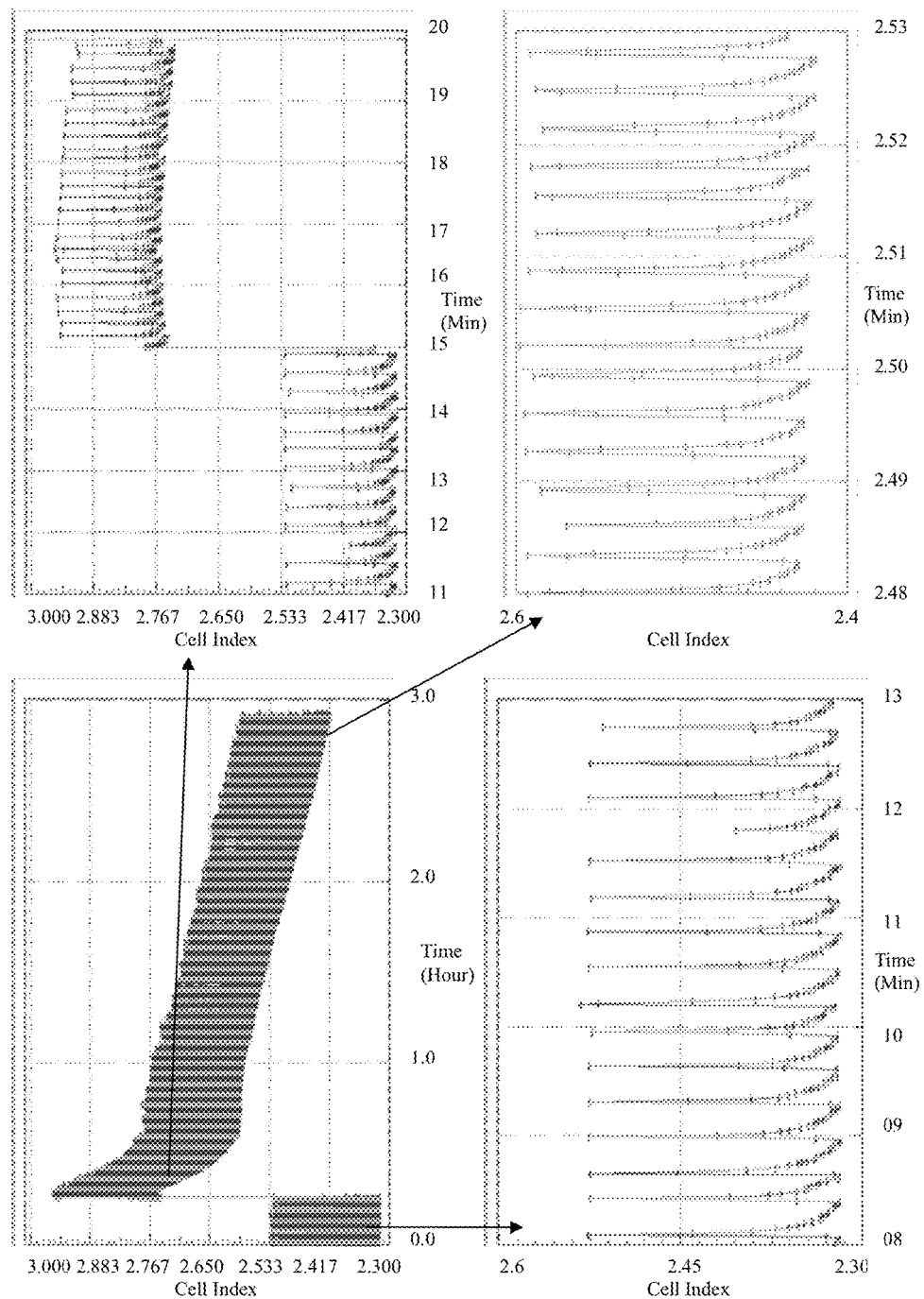
Figure 11J:
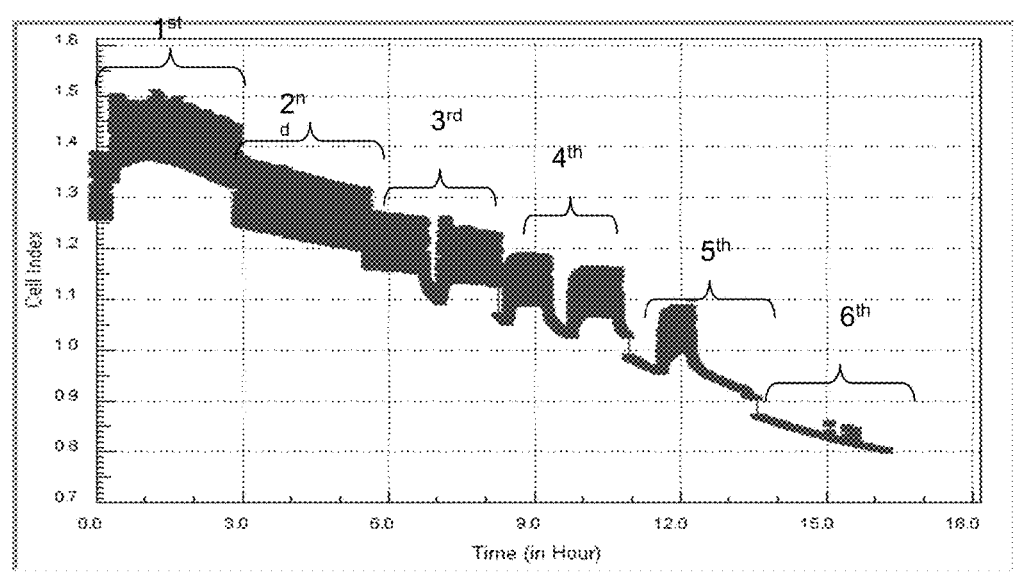
Figure 11J:
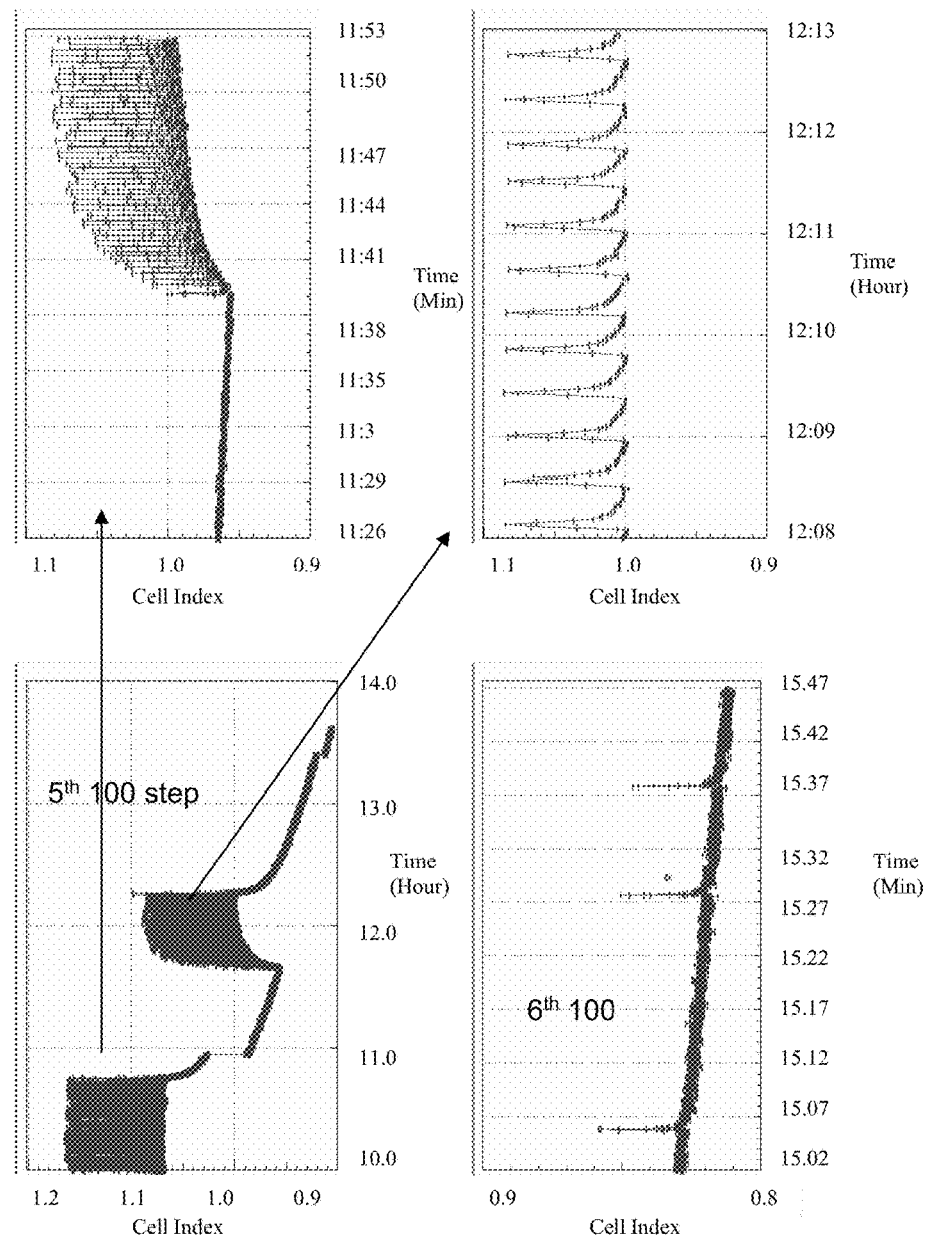
Figure 11K:
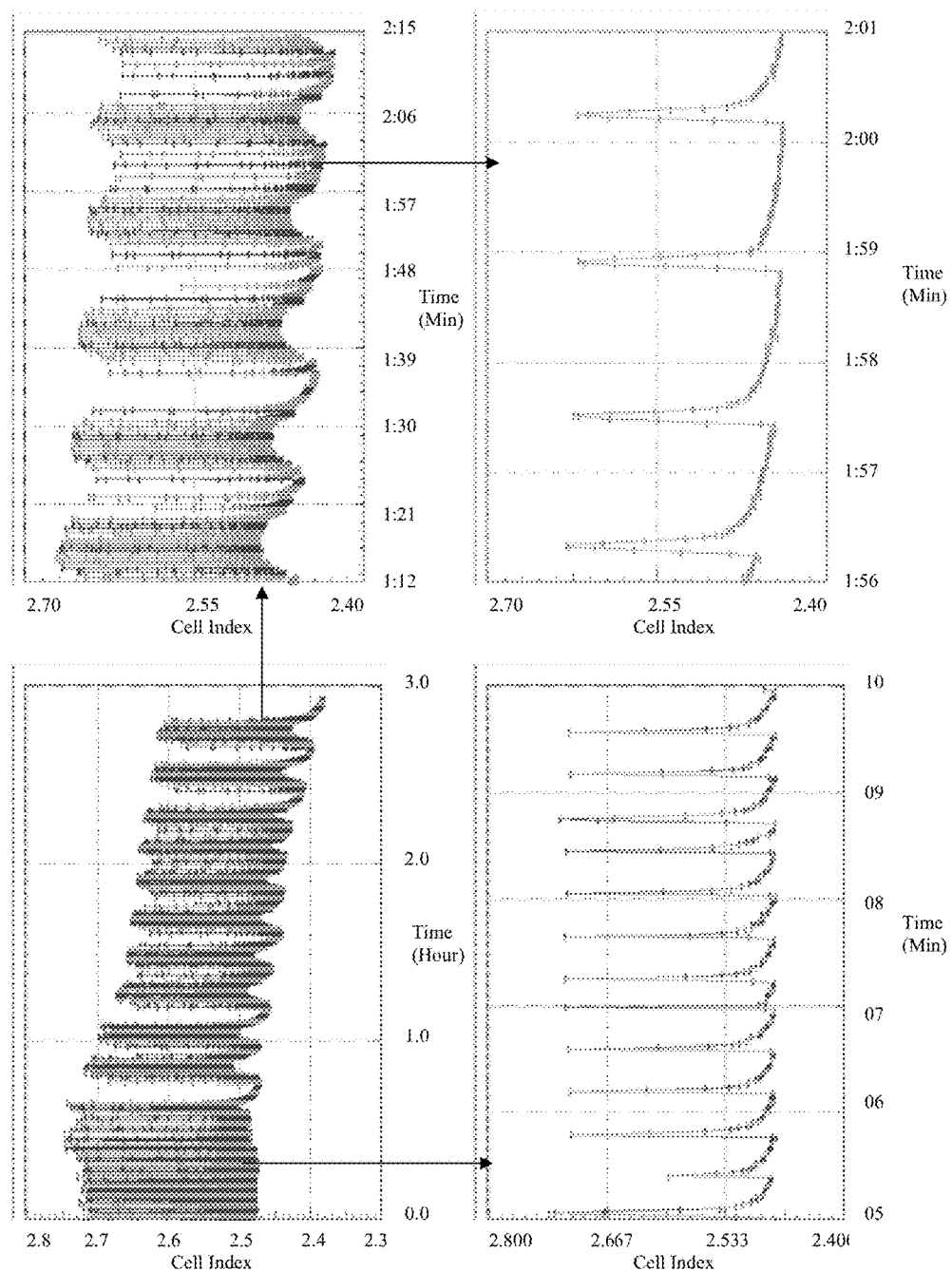
Figure 11L:
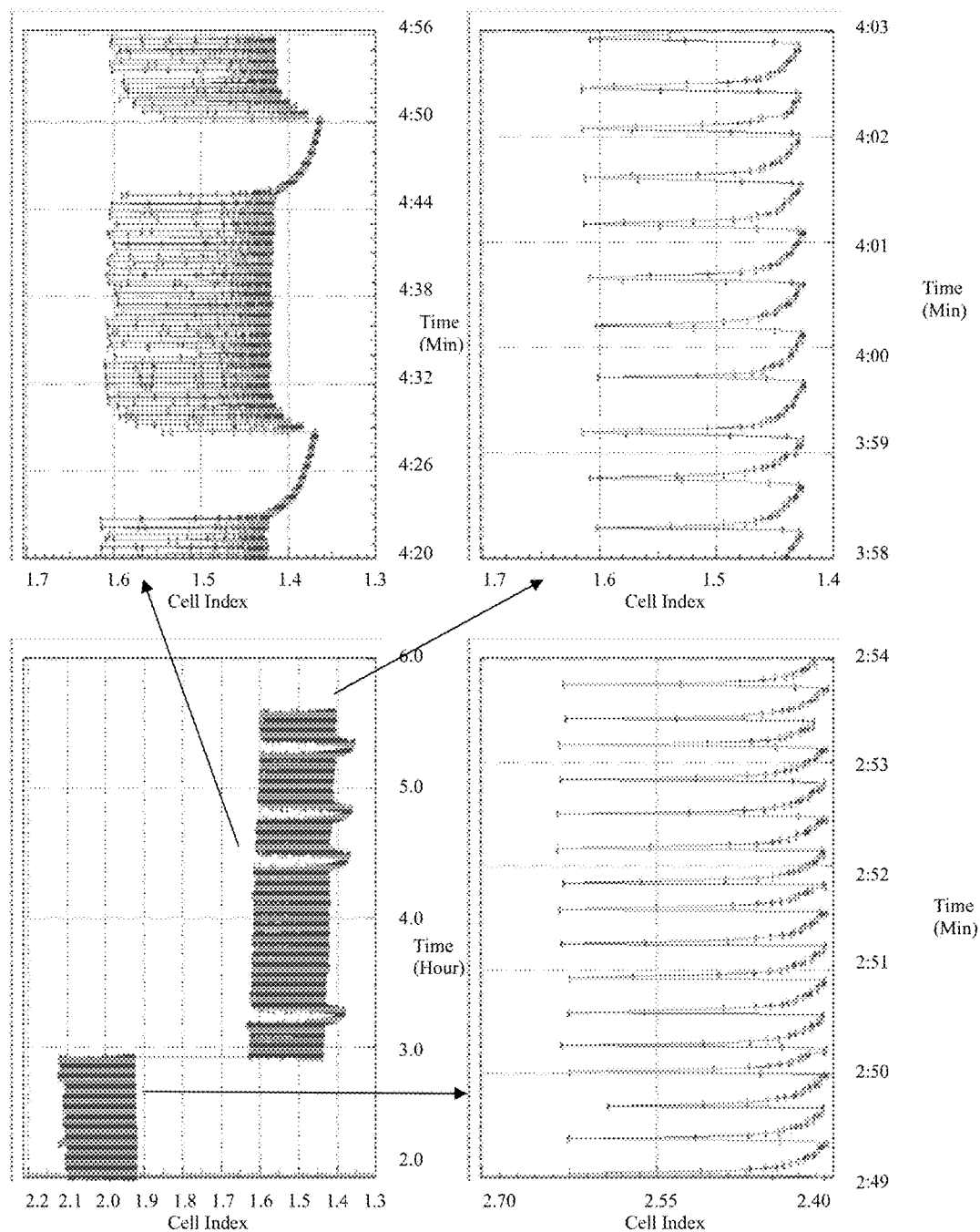
Figure 11M:
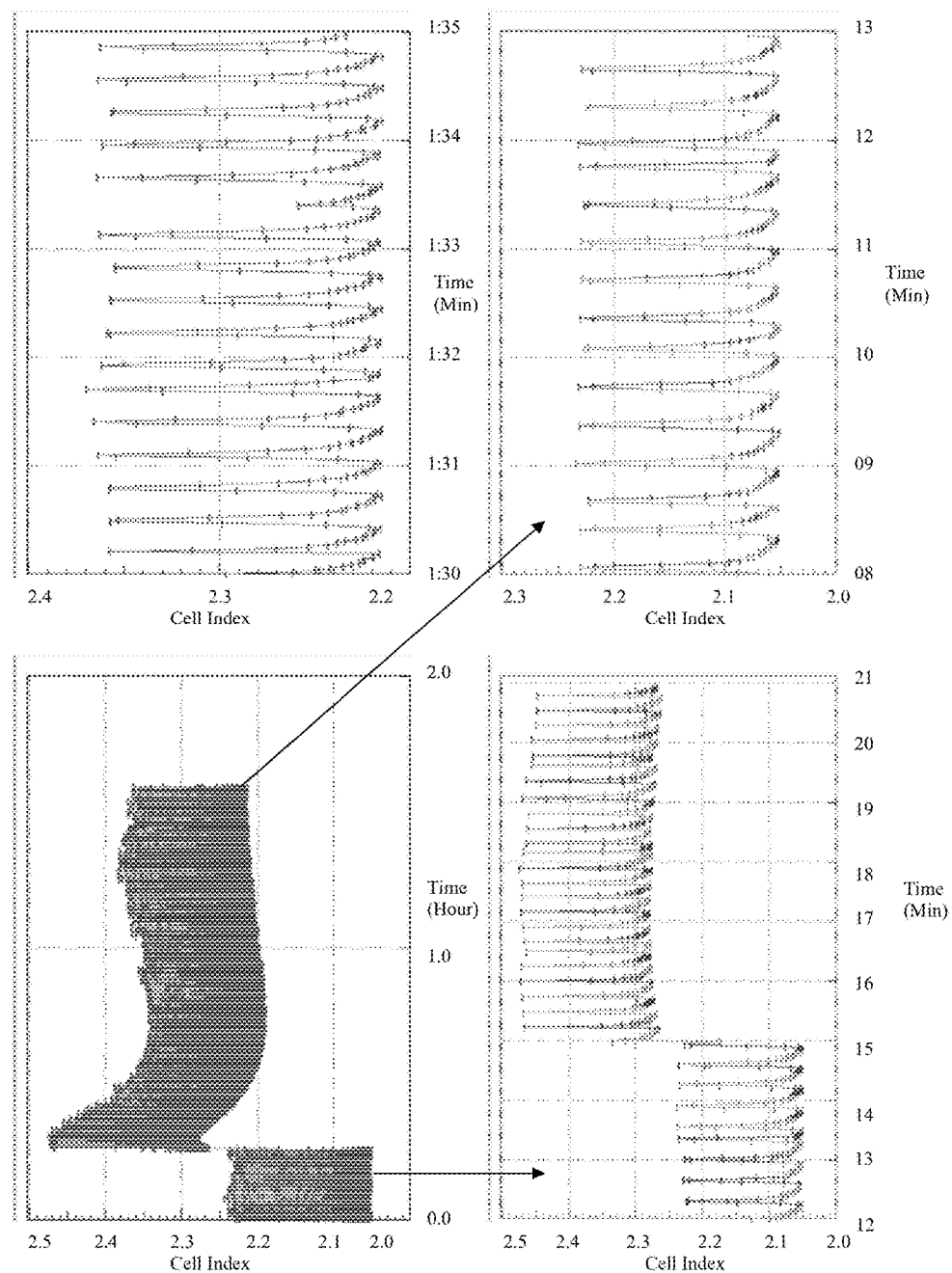
Figure 11N:
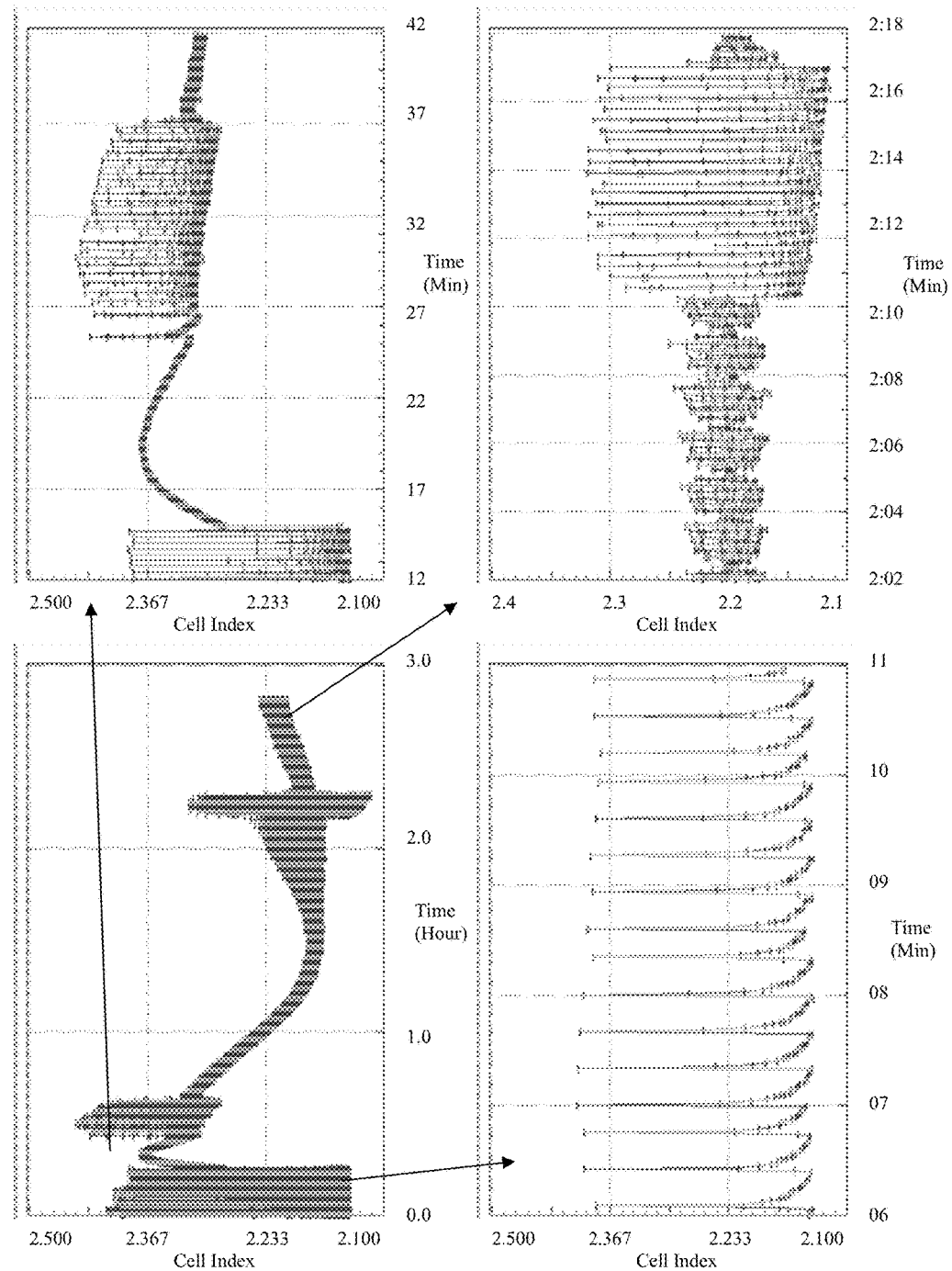
Figure 11O:
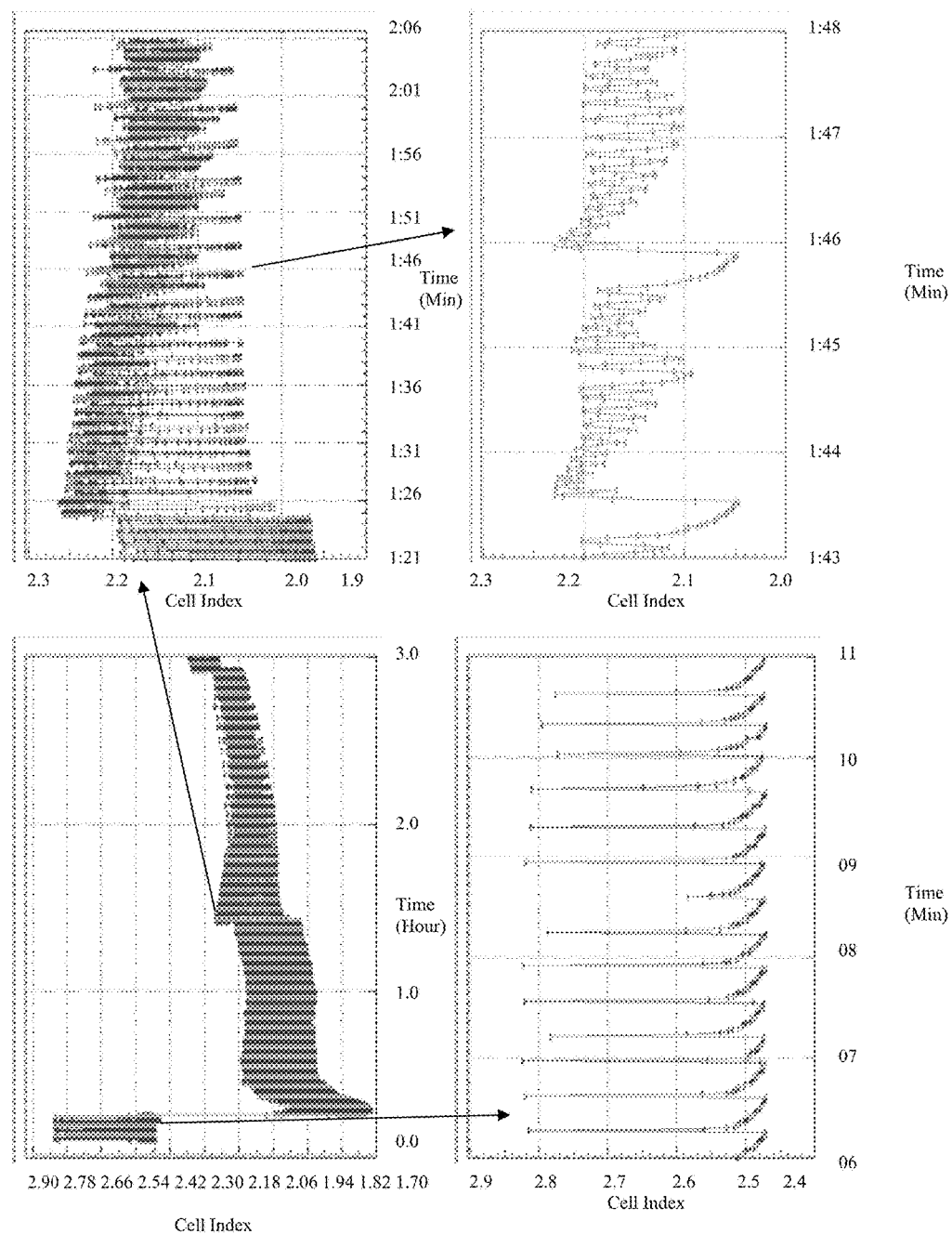
Figure 11P:
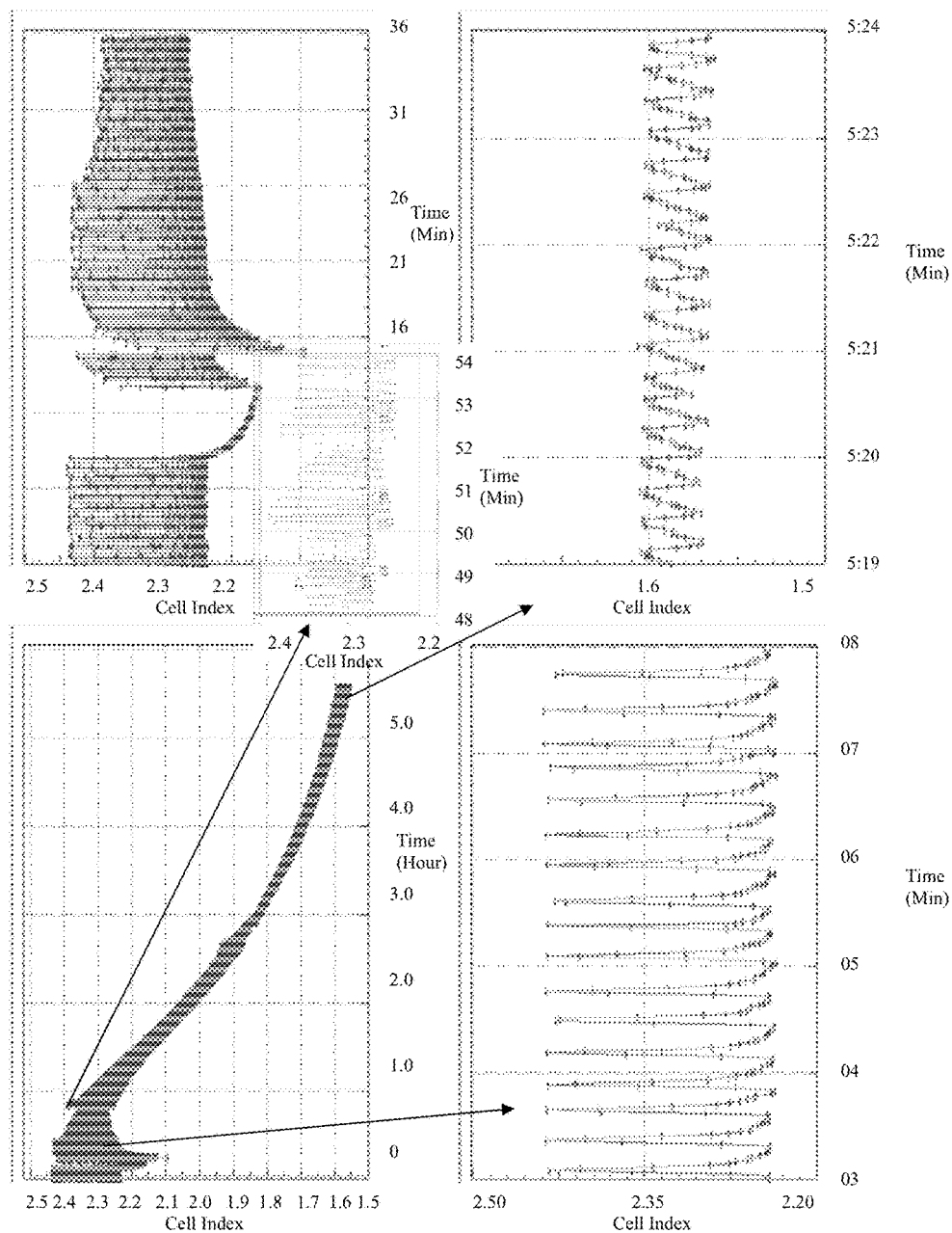
Figure 11Q:
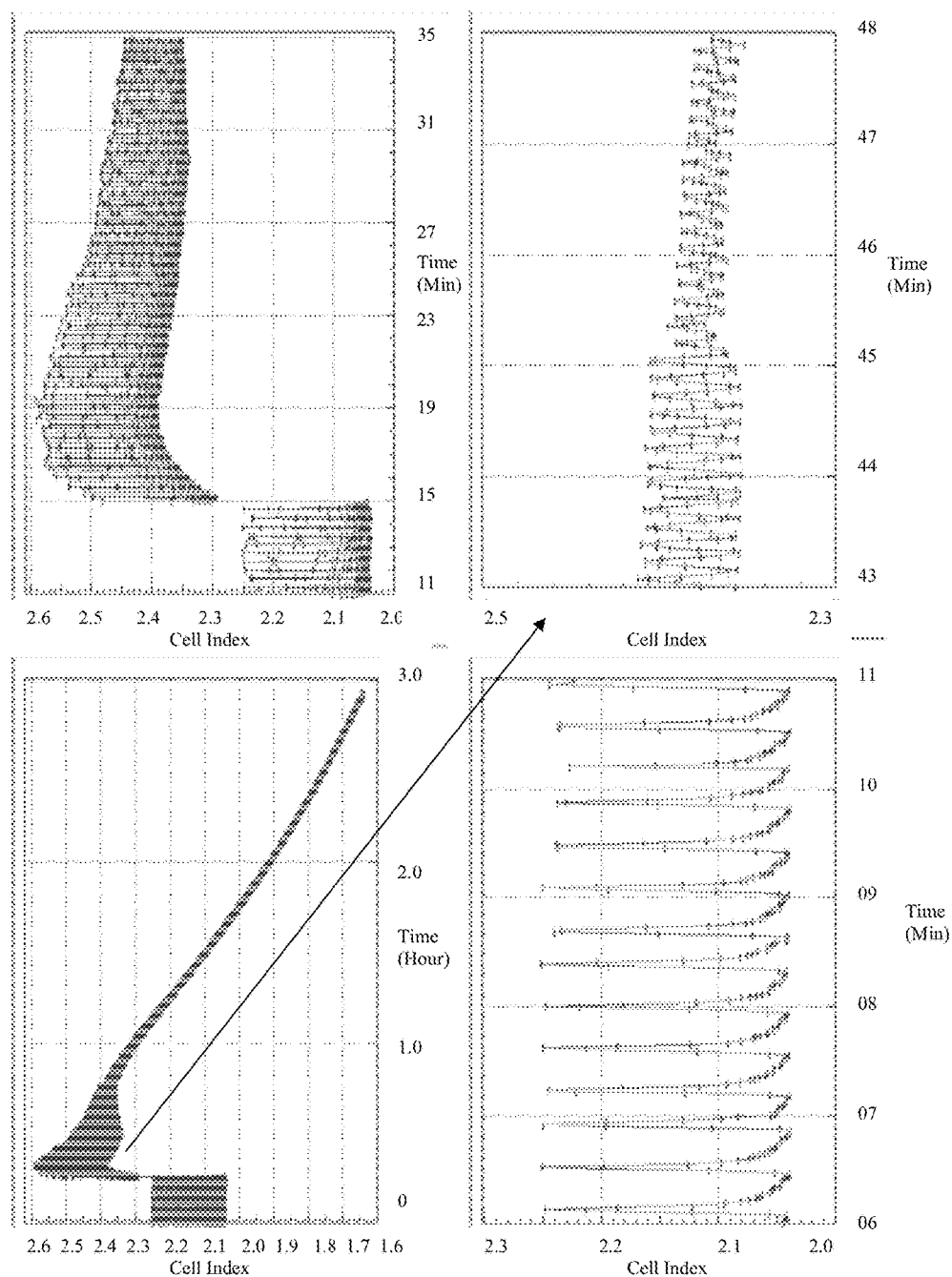
Figure 11R:
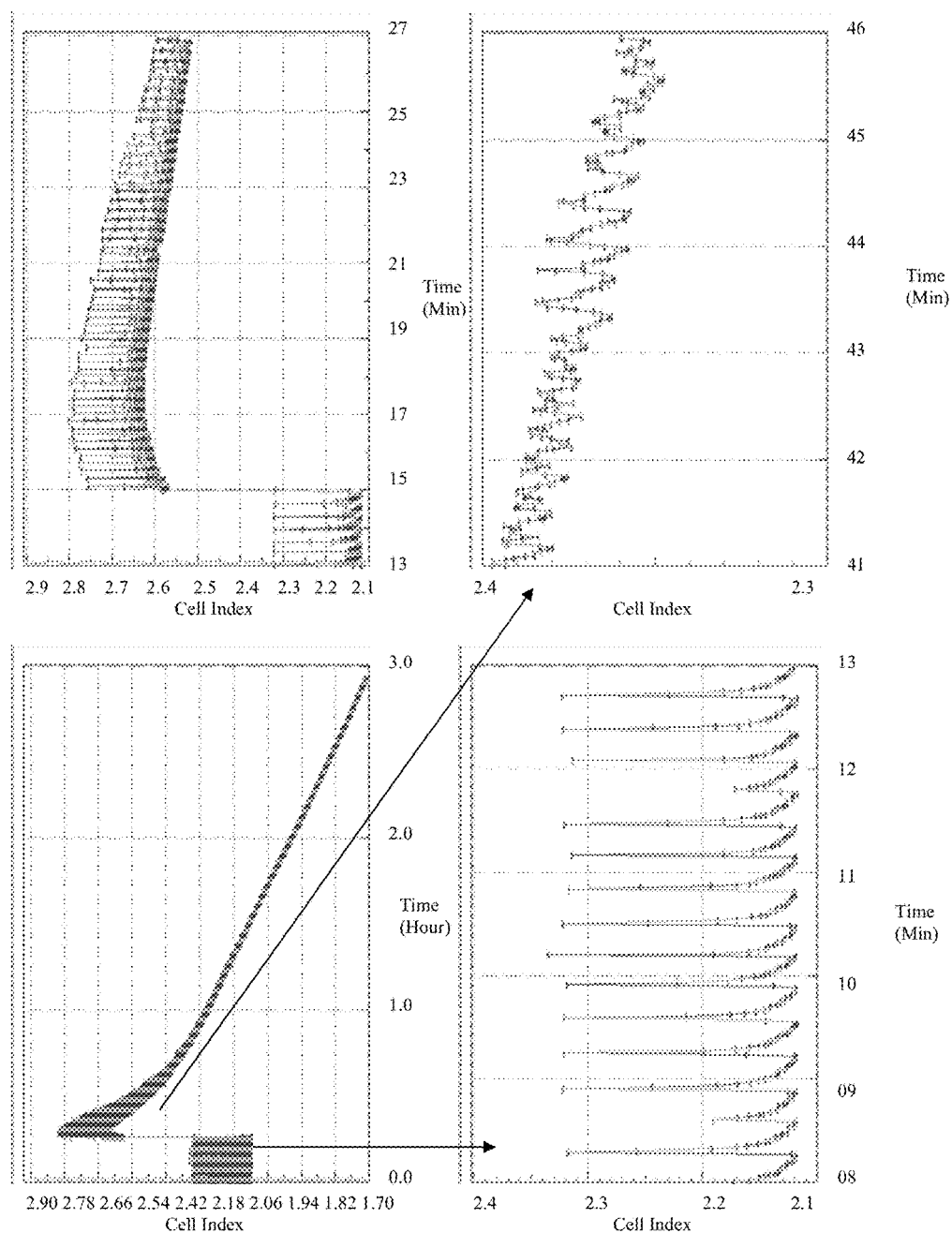
Figure 11S:
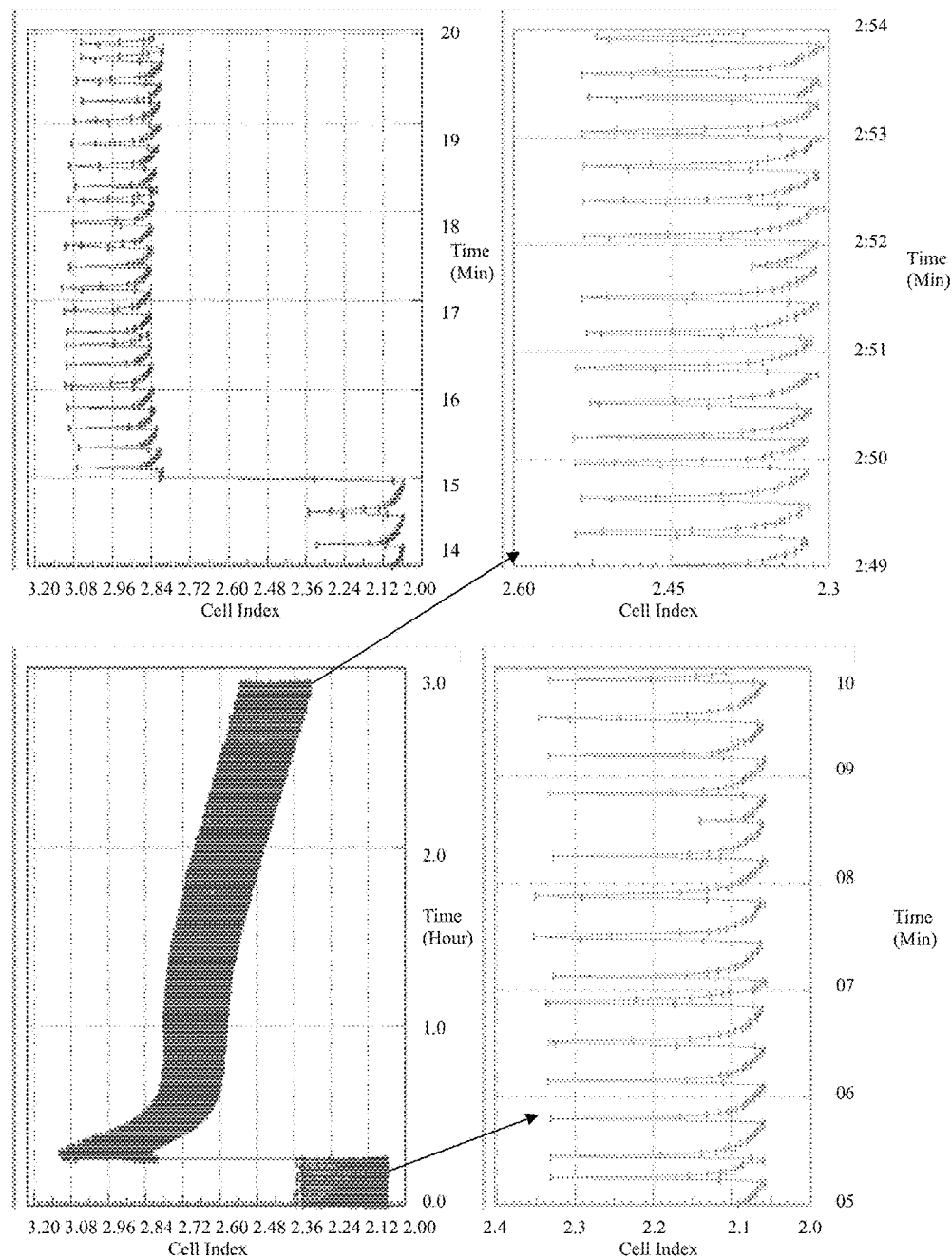

In order to demonstrate the utility of the millisecond kinetic impedance-measurements, we first used two pharmacological agents, one known to suppress the heart rate and consequently cardiomyocyte beating and the other known to increase the heart rate and consequently the rate of cardiomyocyte beating. As Mouse ES cells were seeded in FN-coated E-PLATES and monitored for about 72 hours when the cells differentiated into beating cardiomyocytes, as described in Section 4. A baseline of the cardiomyocyte was taken for approximately 40 seconds using the specially designed fast kinetic data acquisition hardware and software which is capable of millisecond data acquisition and display. An agonist of muscarinic receptors, carbachol, which is known to slow down the heart rate was added to one well at a final concentration of 333 nM and cardiomyocyte beating was monitored for 10 minutes (FIG. 10A). The data clearly shows that carbachol significantly slows down the rate of cardiomyocyte beating from 80 beats/min prior to carbachol addition to ~60 beats/min after carbachol addition (Table I). Alternatively, addition of isoproteranol at a final concentration of 4.4 uM significantly increased the rate of cardiomyocyte beating from ~65 beats/min to 115-135 beats/min (FIG. 10B and Table I). These data clearly show that the readout system and the fast kinetic software are sufficiently robust and sensitive to detect these changes in rate of cardiomyocyte beating even at very low compound concentrations. Similar to the cell index plot shown in FIGS. 9C and 9D, the time resolution between two adjacent points in FIGS. 10A and 10B is 40 milliseconds. In other words, a second in FIGS. 10A and 10B is equivalent to 40 millisecond.

TABLE I

| Compound | Mechanism | Concentration | Beat Rate | Amplitude | Pattern Change |
| --- | --- | --- | --- | --- | --- |
| Carbachol | Muscarnic receptor agonist | 333 nM | From ~80 to ~60 | From 0.07 to 0.06 | Beating rate decreased |
| Isoproteranol | b2 Adrenergic receptor agonist | 4.4 uM | From ~65 to 115-136 | From 0.19 to 0.16 | Beating rate increased |

To further demonstrate the capabilities of the improved impedance-based monitoring of cardiomyocyte beating in detecting drugs which may adversely affect heart function, a number of drugs which have been pulled out of the market due to cardiotoxic side effects such as ERG channel inhibition and QT elongation were compiled and tested in a dose-dependent manner. The list of these compounds, their mechanism and adverse side affects are shown in Table II. For these tests, mouse ES derived cardiomyocytes were seeded at a final density of 25,000 cells in ACEA E-Plates and continually monitored by the RT-CES system. Approximately, 72 hours after cell seeding the improved, impedance-measurement system with millisecond time resolution was used to establish a baseline reading of cardiomyocyte beating for each well for about 40 seconds. Subsequently, the cells in each well were treated with the indicated drug and dose shown in FIG. 11. Similar to the cell index plot shown in FIGS. 9C and 9D, the time resolution between two adjacent points in all the figures in FIG. 9 is 40 milliseconds. In other words, a second in FIG. 9 is equivalent to 40-milliseconds.

Figure 12:
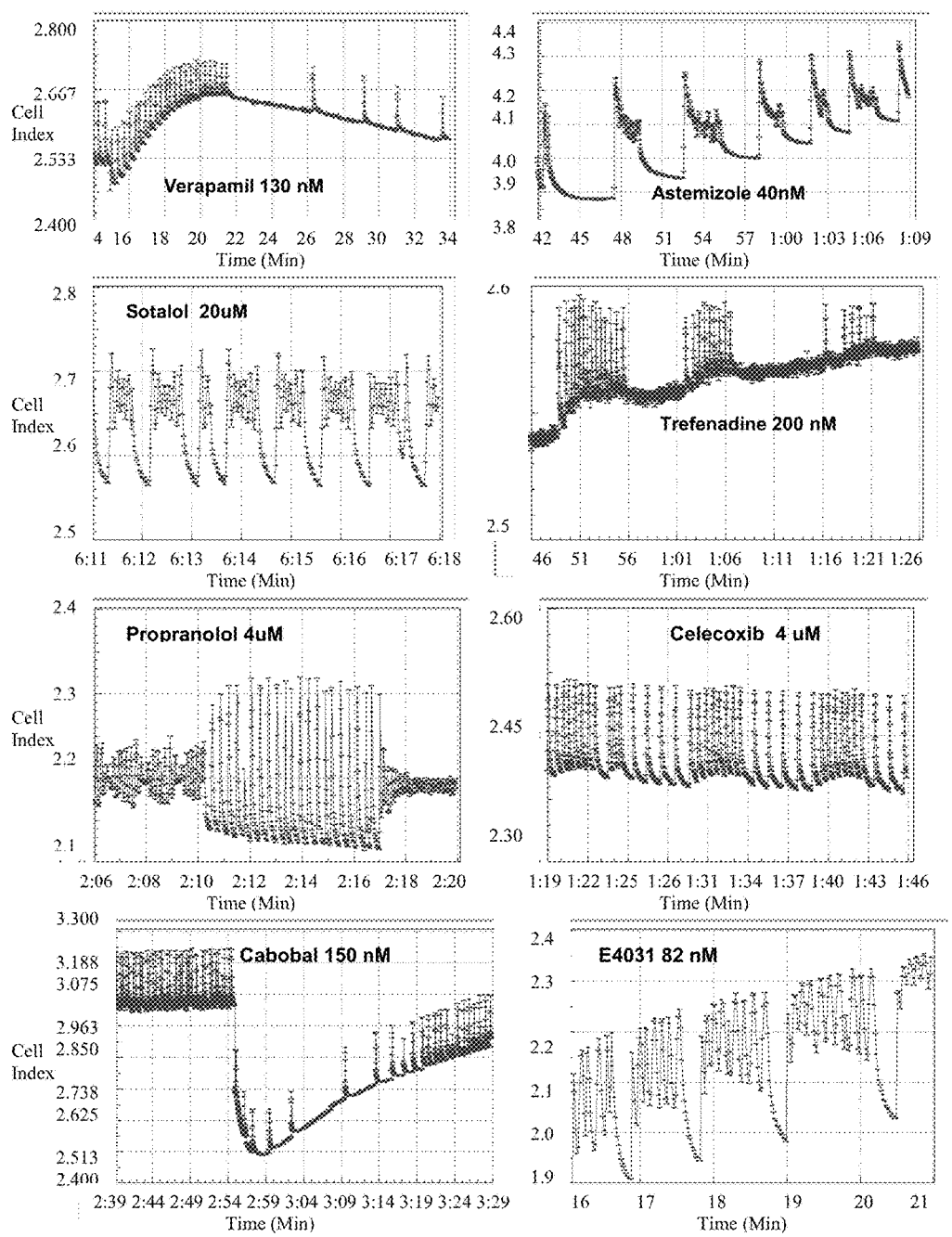
FIG. 12 depicts impedance based cardiotoxic patterns from known compounds.

Table II shows a summary of the results, clearly demonstrating that compounds which have been shown to affect ERG channels do affect various aspects of cardiomyocyte beating and function such as frequency of beating, magnitude of beating. Furthermore, as shown in FIG. 12 some of these compounds can lead to qualitatively different or similar patterns. For example, the compounds E4031, Astezimole and dofetilide which are ERG channel inhibitors do contain patterns with similar features. In summary these results clearly indicate that using the impedance-measurement system with millisecond time resolution do lead to a sensitive and robust readout for cardiomyocyte beating that can also detect drugs which are known to be cardiotoxic. Similar to the cell index plot shown in FIGS. 9C and 9D, the time resolution between two adjacent points in all the figures in FIG. 10 is 40 milliseconds. In other words, a second in a figure in FIG. 10 is equivalent to 40-millisecond.

TABLE II

| Compound | Mechanism | Concentration | Beat Rate | Amplitude | Pattern Change |
| --- | --- | --- | --- | --- | --- |
| Astemizole | anti-histamine | 400 nM | 0 | <0.01 | From 68-72 bpm to irregular being to beating stopped |
| Terfenadine | anti-histamine | 200 nM | 0 | <0.01 | From 71-78 bpm to irregular beating to beating stopped |
| Erythromycin | anti-biotic | 13.3 uM | From ~60 to ~80 | 0.09 to 0.07 | No pattern change |
| Moxifloxacin | anti-biotic | 20 uM | From ~80 to ~73 | From 0.055 to 0.060 | No pattern change |
| Pentamidine | anti-infective | 20 uM | From 71~78 to ~71 | From 0.24 to 0.21 | No pattern change |
| Amitriptyline | Serotonergic Inhibitor | 4.4 uM | From ~70 to ~90 | From 0.22 to 0.17 | No pattern change |
| Verpamil | Ca channel blocker | 130 uM | From ~65 to 0 | From 0.13 to 0.06 | From ~65 bpm to only occasional single beating. |
| Rosglitazone | PPAR agonist | 13.3 uM | From ~79 to ~75 | From 0.22 to 0.17 | No pattern change |
| Dofitlite | | 500 uM | From ~80 to ~180 | From 0.09 to 0.02 | Pattern changed, much faster |
| Rofecoxib | COX-2 Inhibitor | 13.3 uM | From ~68 to ~60 | From 0.2 to 0.19 | No pattern change |
| Rofecoxib | COX-2 Inhibitor | 40 uM | From ~62 to ~60 | From 0.16 to 0.10 | Pattern change, no beating after initial treatment, then recovers |
| Celecoxib | COX-2 Inhibitor | 4.4 uM | From ~60 to (~20-~50) | From ~0.2 to ~0.12 | Pattern change |
| Doxirubicin | Anthracycline | 40 uM | ~70 | ~0.16 | No pattern change (initially). Beating pattern changes after 2 hrs. |
| Cyclosporin A | Calcineurin inhibitor | 13.3 uM | From ~70 to ~80 | From 0.18 to 0.15 | No pattern change |
| Propalanol | β2-adrenergic receptor antagonist | 4.4 uM | From ~70 to over 150 | From 0.25 to 0.025 | Pattern changed, much faster and irregular |
| Sotalol | | 13.3 uM | From ~80 to ~160 | From 0.27 to 0.07 | Much faster, pattern changed |

TABLE II-continued

| Compound | Mechanism | Concentration | Beat Rate | Amplitude | Pattern Change |
|---|---|---|---|---|---|
| E4031 | K channel inhibitor | 120 nM | From 80 to 160 | From 0.09 to 0.03 | Pattern changed, much faster |
| DDT | Pesticide | 8 uM | From 80 to 140, then to ~80 | From 0.25 to 0.02 | Inititally become faster, later irregular beating |
| PCB | Organic toxicant | 8 uM | From ~65 to o | From 0.2 to 0 | Beating stopped |
| Endosulfan | insecticide | 8 uM | From ~75 to o | From 0.2 to 0 | Beating stopped |

Figure 13:
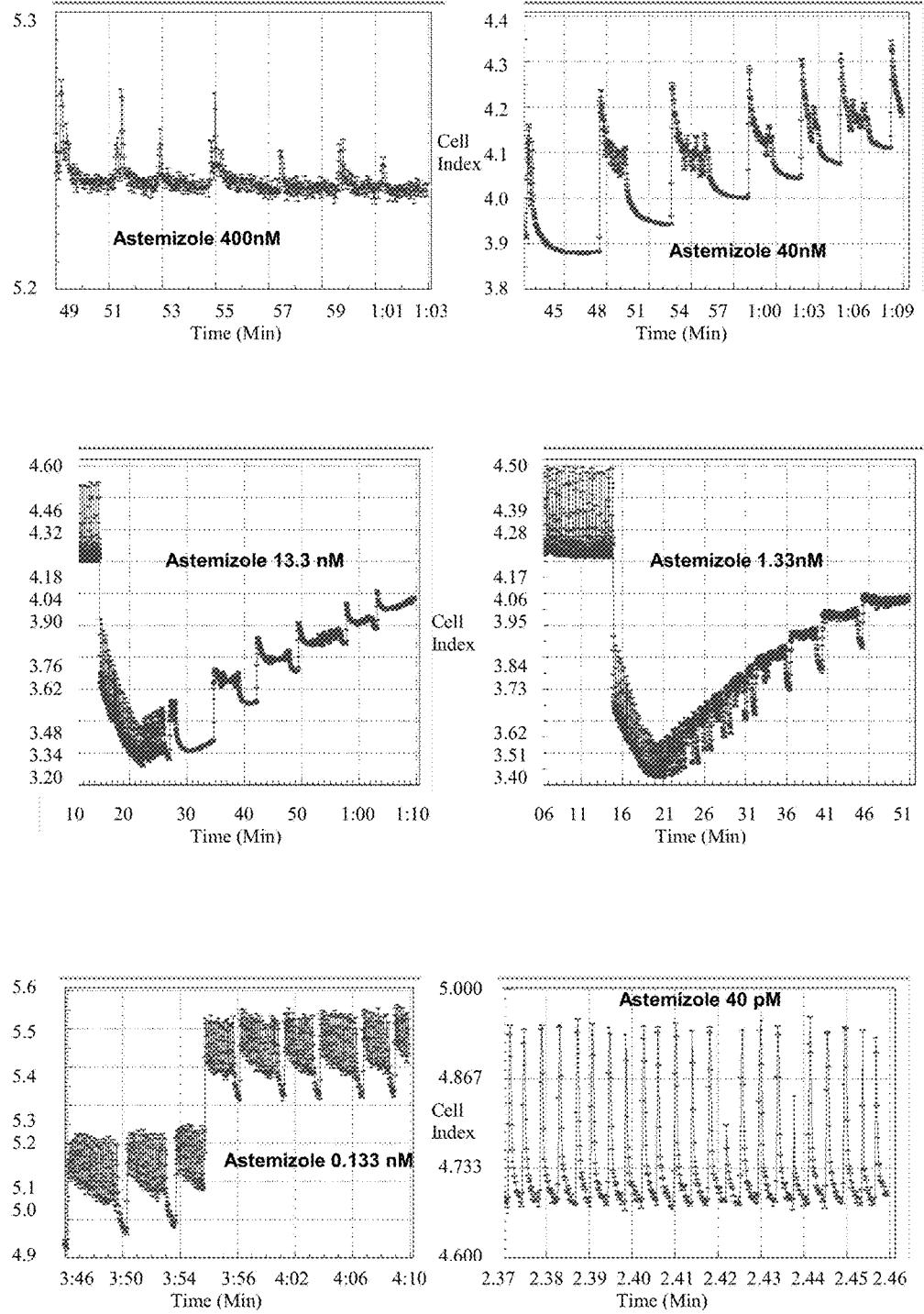
FIG. 13 shows an example of dose dependent effects of Astemizole on cardiomyocytes beating at different concentrations.

To further demonstrate the capabilities of the fast impedance-measurement-system-based monitoring of cardiomyocyte beating in detecting drugs which may adversely affect heart function, compounds at different concentrations were tested to demonstrate the dose-dependent effects of these compounds on cardiomyocytes. Approximately, 72 hours after cell seeding the impedance-measurement system with millisecond time resolution was used to establish a baseline reading of cardiomyocyte beating for each well for about 40 seconds. Subsequently, the cells in each well were treated with drugs at different dose concentrations. FIG. 13 shows an example of dose dependent effects of Astemizole on cardiomyocytes beating at different concentrations. At high concentration of 400 nM, Astemizole had such a strong effect on the beating of cardiomyocytes that the beating almost stopped. The effect of Astemizole on the beating of the cardiomyocytes is clearly does-dependent. At low concentration of 40 pM, its effect on the beating of the cardiomyocytes is small that the cardiomyocyte beating rate was not affected. Similar to the cell index plot shown in FIGS. 9C and 9D, the time resolution between two adjacent points in all the figures in FIG. 11 is 40 milliseconds. In other words, a second in FIG. 13 is equivalent to 40 milliseconds.

Example 6

Figure 14:
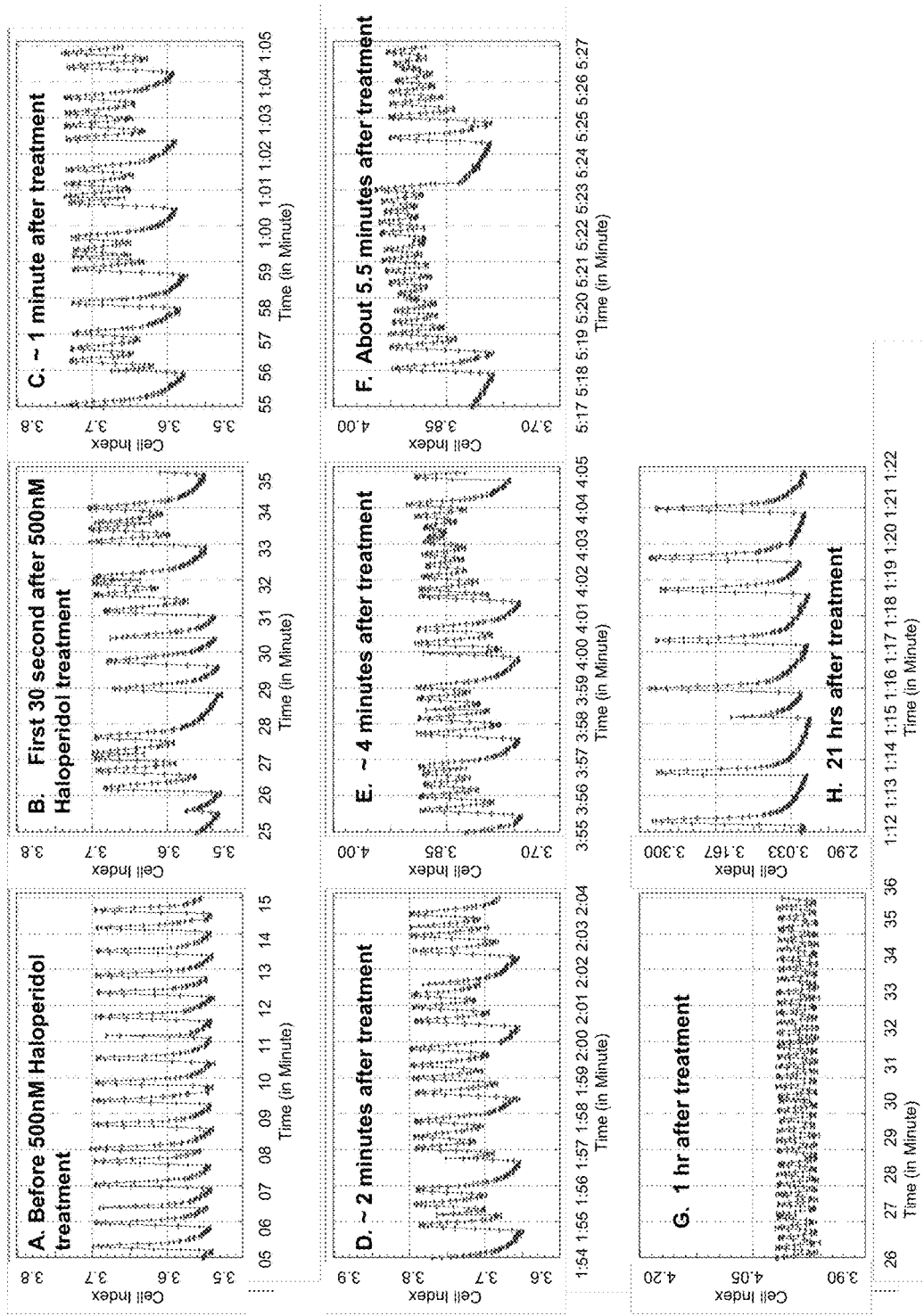
FIGS. 14A-H are graphical depictions of real time impedance-based millisecond time resolution of cardiomyocyte beating in response to Haloperidol treatment. The Y-axis is the cell index value.
Figure 15:
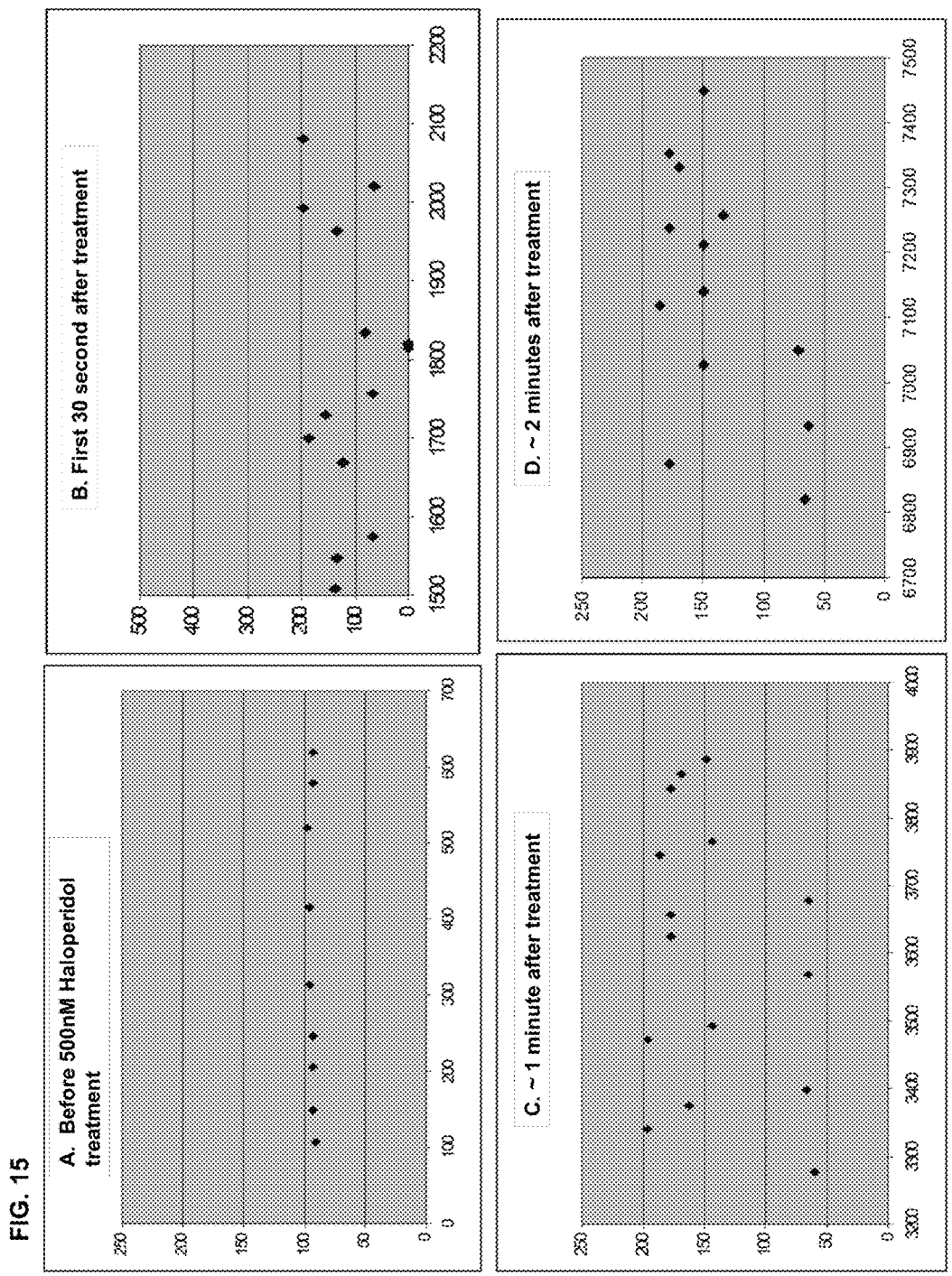
FIGS. 15A-H depict graphical analysis of the impedance beating frequency from impedance plots (cell index plots) shown in FIGS. 14A-H.
Figure 15:
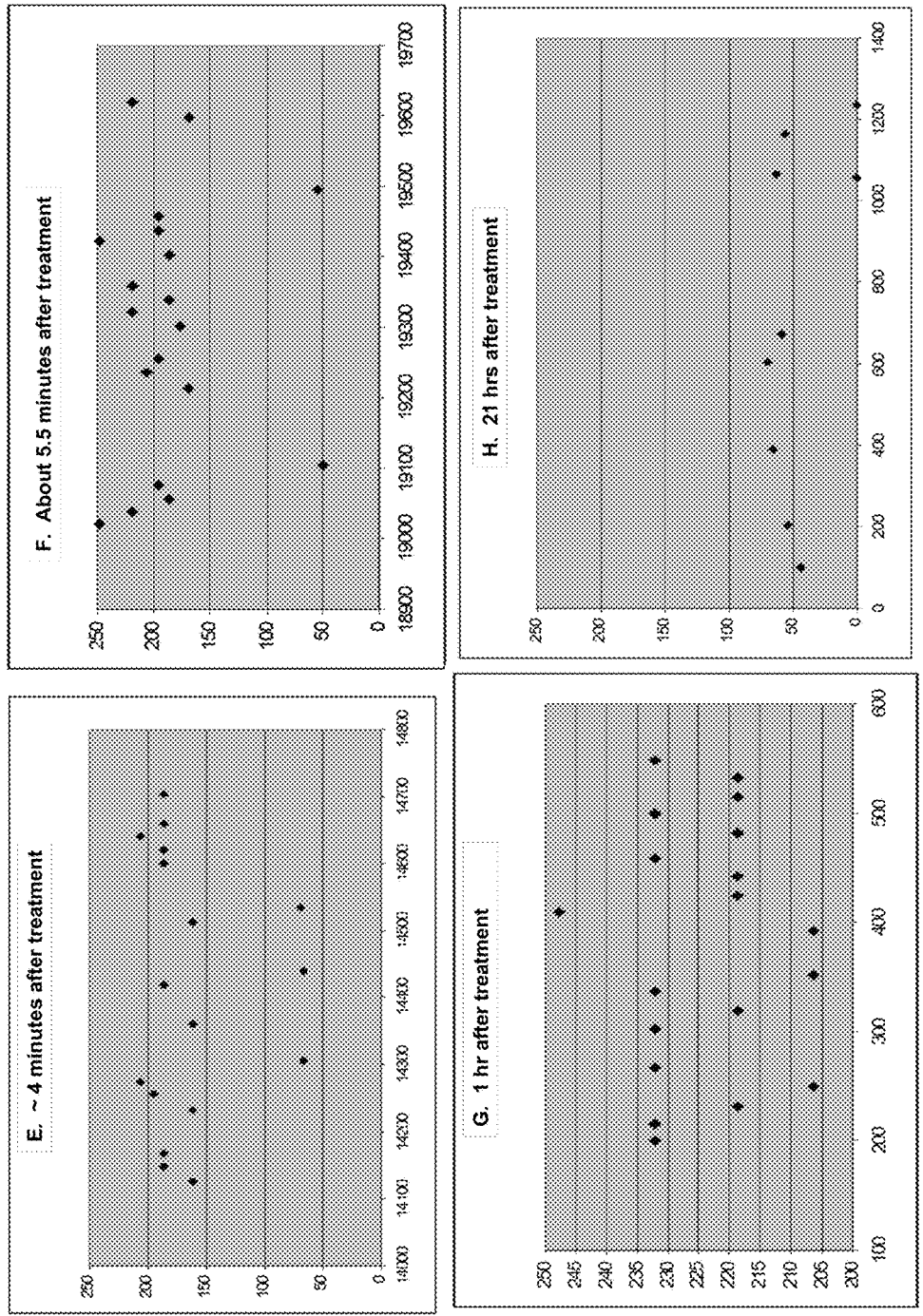
Figure 16:
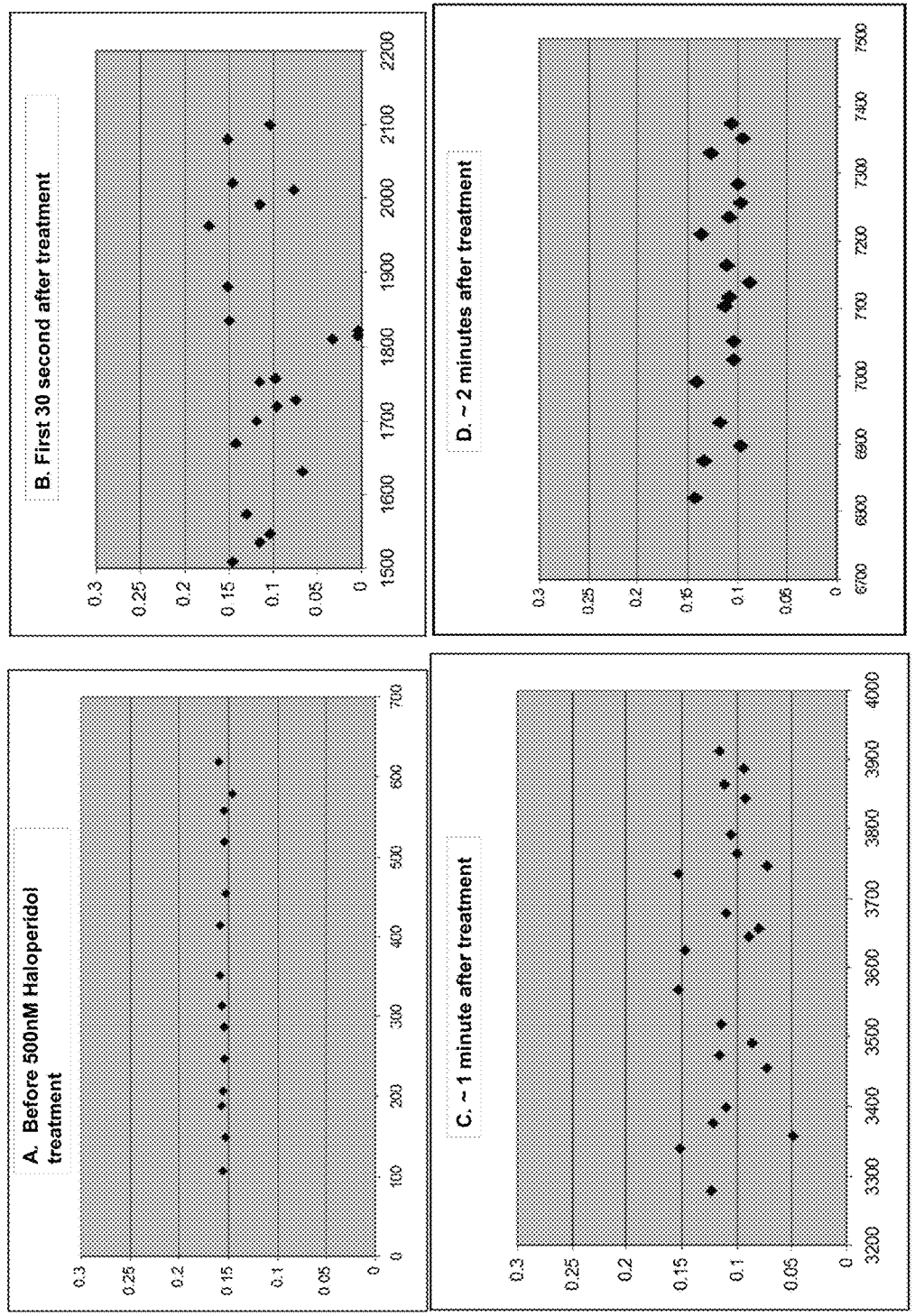
FIGS. 16A-H depict additional graphical analysis of the magnitude or amplitude of the beating cycle peaks from impedance plots (cell index plots) shown in FIGS. 14A-H.
Figure 16:
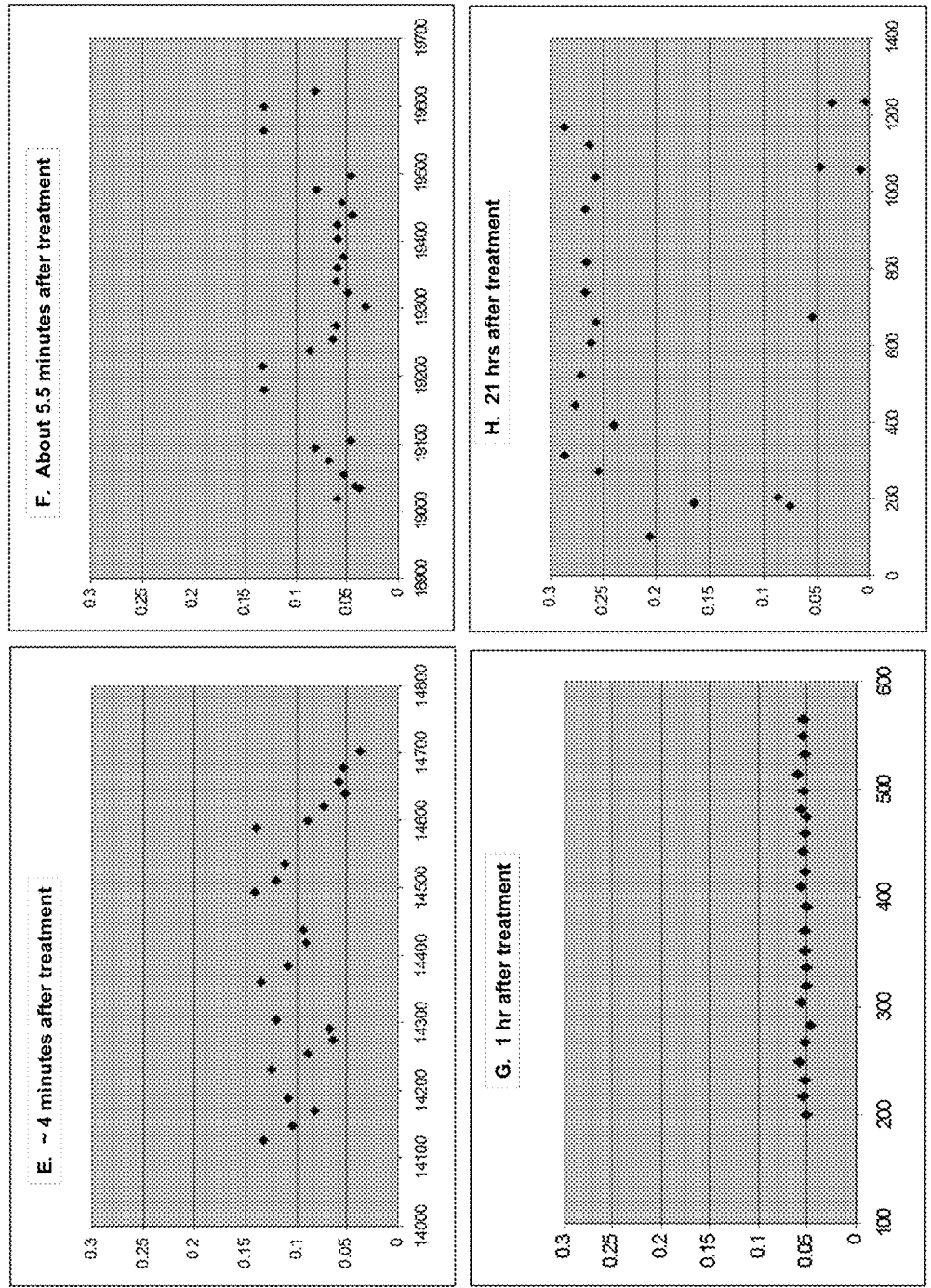

Modulation of Cardiomyocyte Beating in Response to Haloperidol Treatment Using Millisecond Time Resolution To further demonstrate the capabilities of the improved impedance measurement system for monitoring of cardiomyocyte beating in detecting drugs which may adversely affect heart function, 500 nM Haloperidol was tested to demonstrate its time-dependent effects on cardiomyocytes. Approximately, 72 hours after cell seeding the improved impedance system was used to establish a baseline reading of cardiomyocyte beating for each well for about 16 seconds (FIG. 14A). Note that in FIG. 14A, each minute showed on the x-axis of FIG. 14A corresponds to one second in real measurement. Subsequently, the cells in the well treated with 500 nM Haloperidol. FIGS. 14B, C, D, E, F, G and H show the impedance-based monitoring of beating of the cardiomyocytes at time points of first 30 seconds, about 1 minute, about 2 minutes, about 4 minutes, about 5.5 minutes, about 1 hour and about 21 hours after the compound treatment. In FIGS. 14B through 14H, each minute showed on the x-axis corresponds to one second in real measurement. It is clear that within 1 hr of compound treatment, the cardiomyocytes exhibit significant, time-dependent change in their impedance responses. Even at ~21 hrs after compound treatment, the impedance pattern did not restore and the beating frequency (50~60 beats per minute) appeared to become about half of that before compound treatment (90~100 beats per minute before treatment). Yet the amplitude of the impedance response spikes nearly doubled compared with that before compound treatment. FIG. 15 and FIG. 16 show the analysis results of the impedance beating pattern of FIG. 14 in terms of the beating frequency (beats per minute) and the beating magnitude For FIG. 15 and FIG. 16, each unit (1) on the x-axis corresponds to 0.016 second (16 milliseconds) in real measurement.

Example 7

Figure 17:
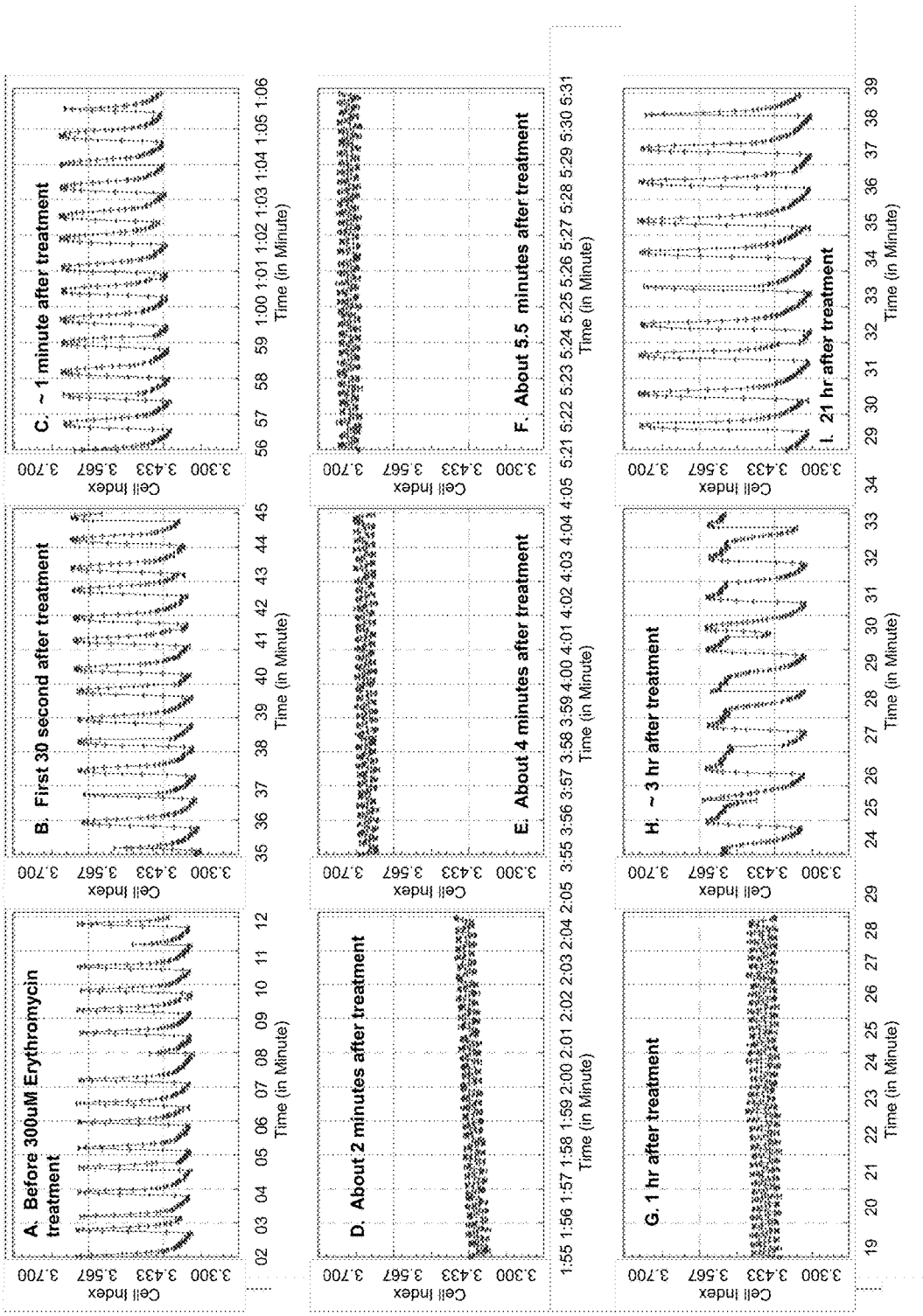
FIGS. 17A-I are graphical depictions of real time impedance-based millisecond time resolution of cardiomyocyte beating in response to Erythromycin treatment. The Y-axis is the cell index value.
Figure 18:
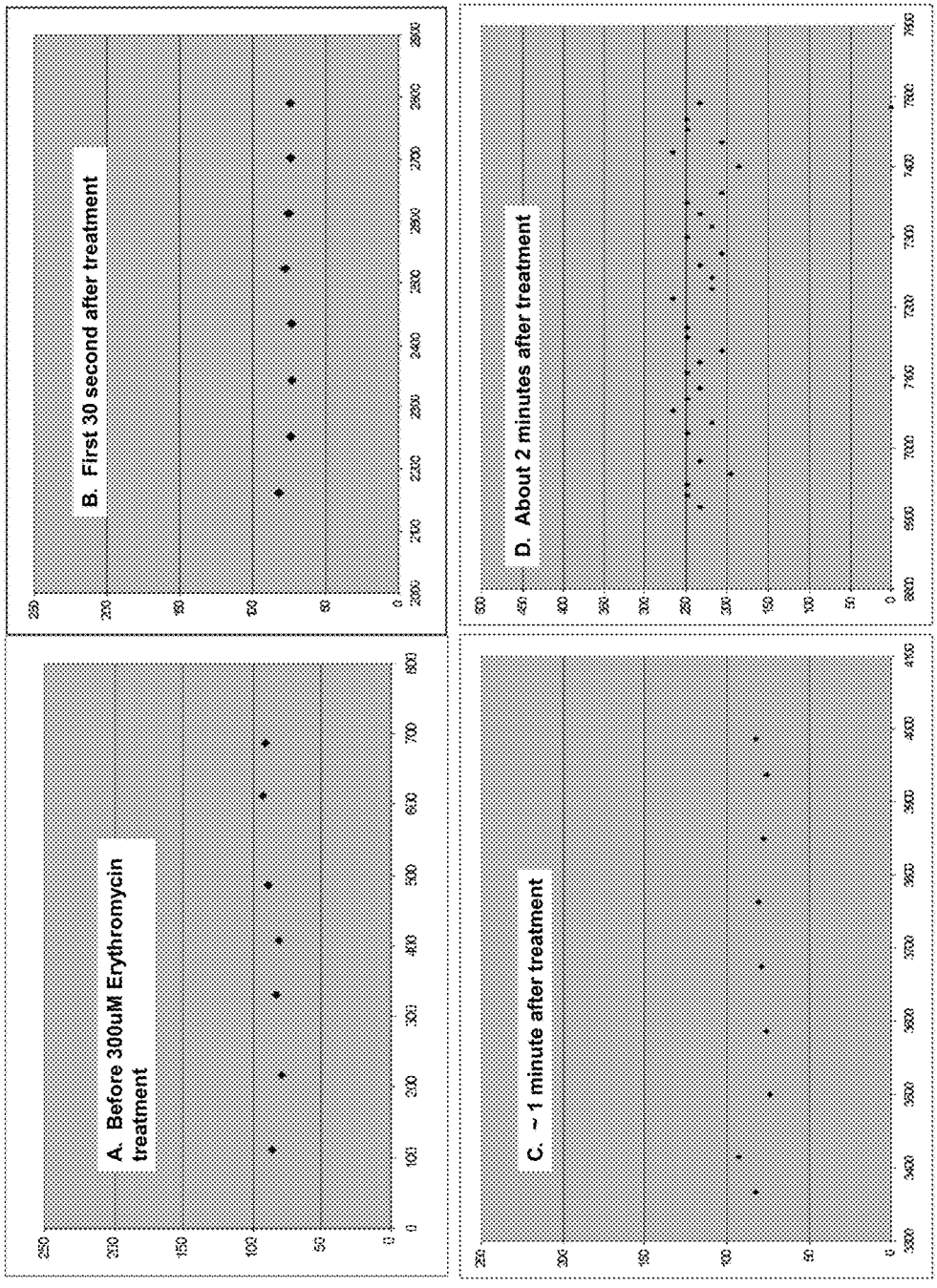
FIGS. 18A-I depict graphical analysis of the impedance beating frequency from impedance plots (cell index plots) shown in FIGS. 17A-I.
Figure 18:
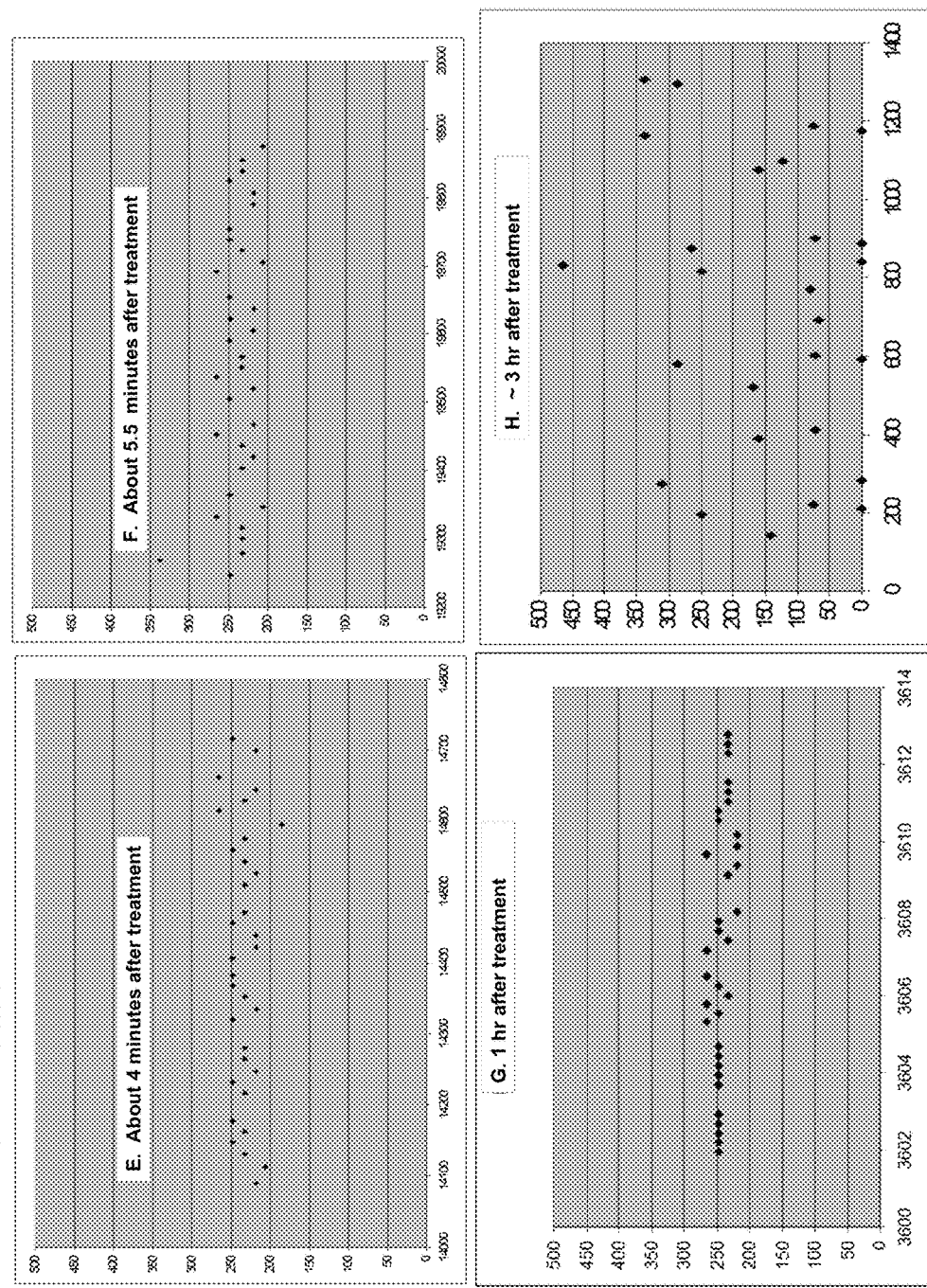
Figure 18:
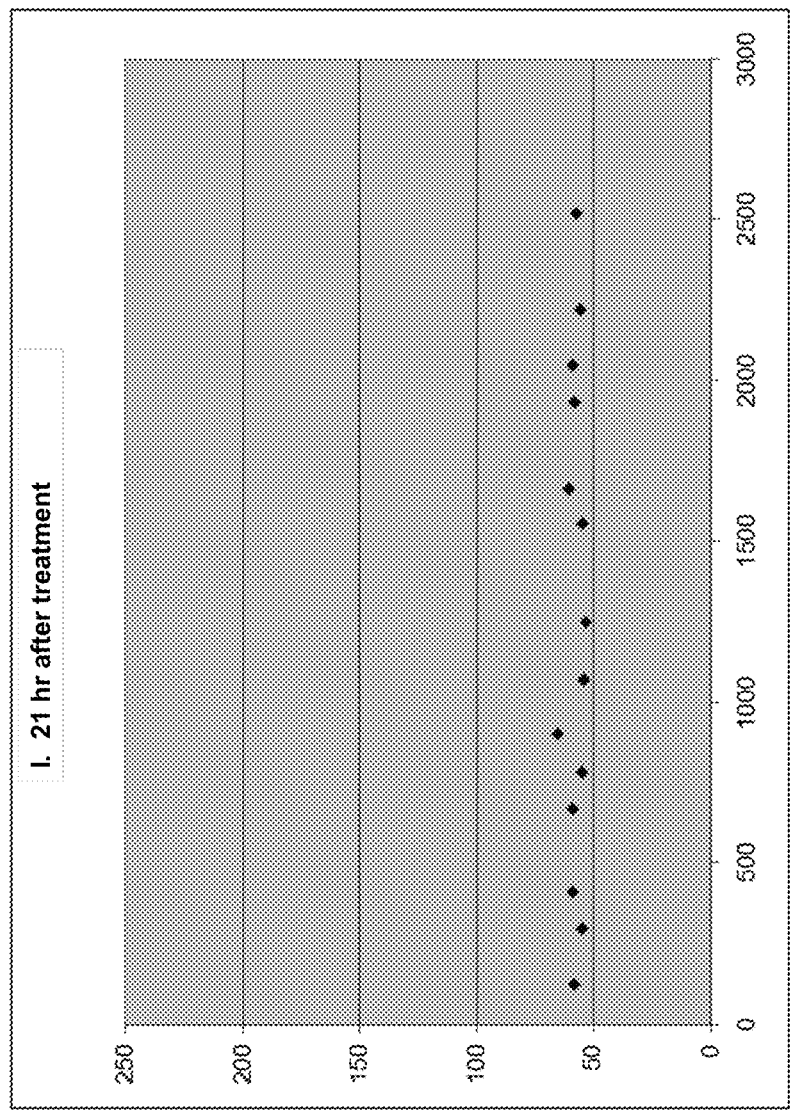
Figure 19:
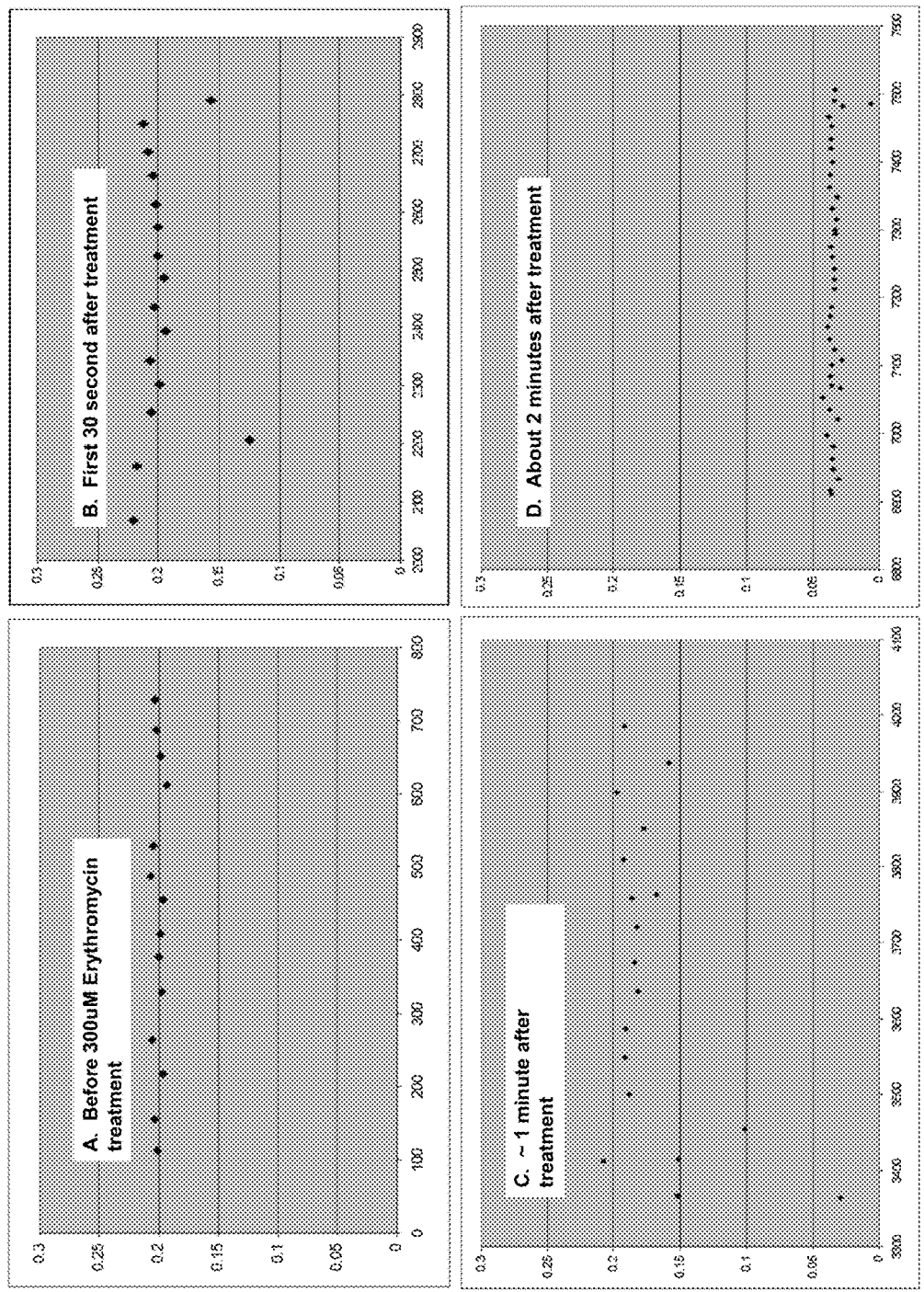
FIGS. 19A-I depict additional graphical analysis of beating magnitude or amplitude of the beating cycle peaks shown from impedance plots (cell index plots) shown in FIGS. 17A-I.
Figure 19:
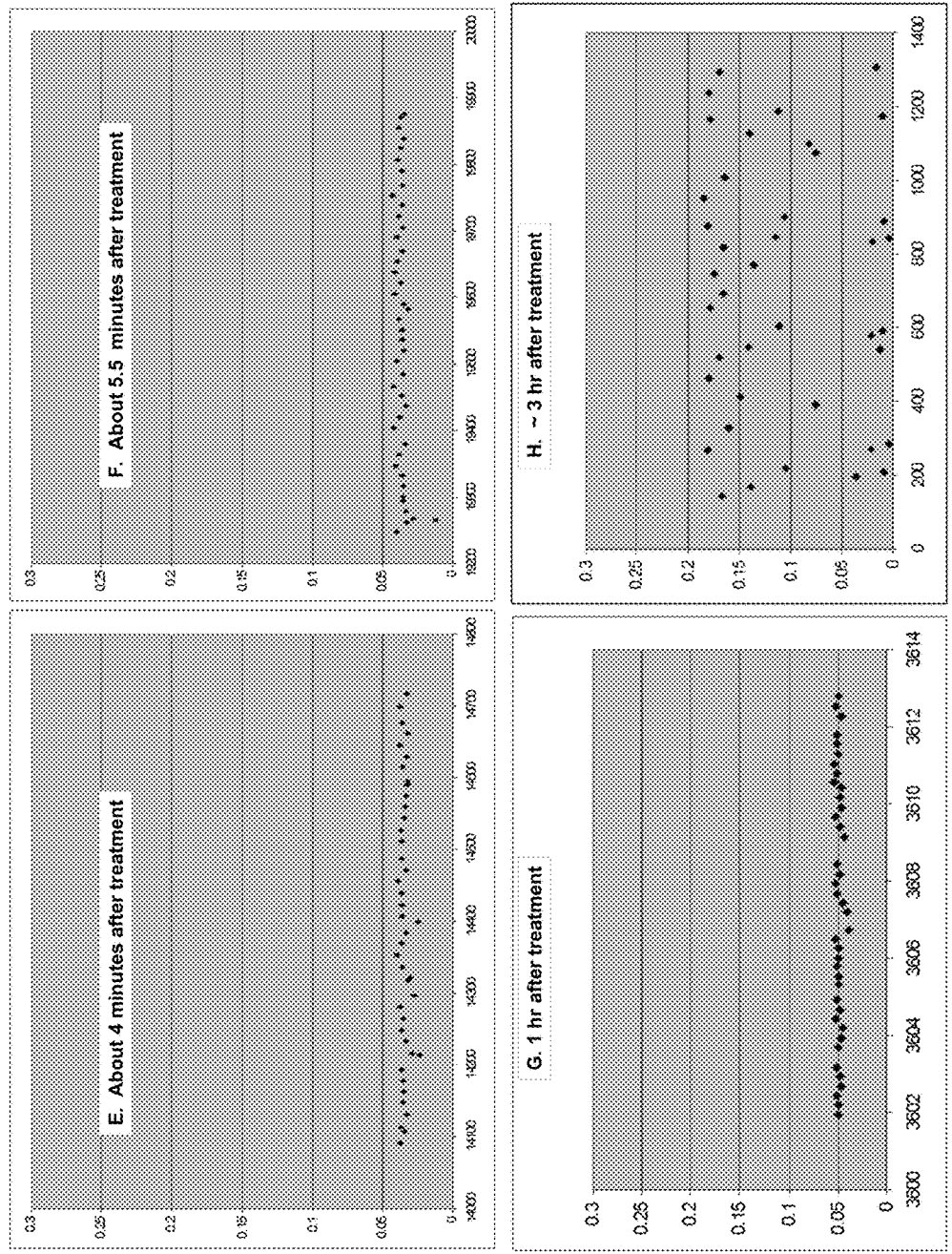
Figure 19:
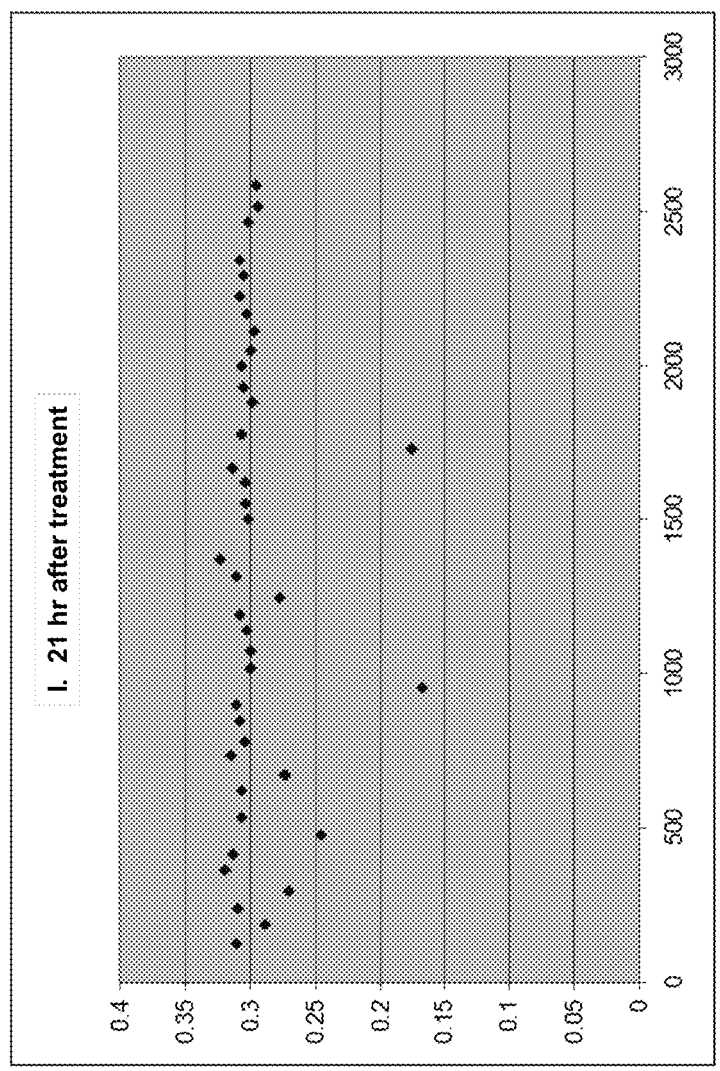

Modulation of Cardiomyocyte Beating in Response to Eryromycin Treatment Using Millisecond Time Resolution To further demonstrate the capabilities of the improved impedance measurement system for monitoring of cardiomyocyte beating in detecting drugs which may adversely affect heart function, 300 uM erythromycin was tested to demonstrate its time-dependent effects on cardiomyocytes. Approximately, 72 hours after cell seeding the improved impedance system was used to establish a baseline reading of cardiomyocyte beating for each well for about 15 seconds (FIG. 17A). Note that in FIG. 17A, each minute showed on the x-axis of FIG. 17A corresponds to one second in real measurement. Subsequently, the cells in the well treated with 300 uM erythromycin. FIGS. 17B-I show the impedance-based monitoring of beating of the cardiomyocytes at time points of first 30 seconds, about 1 minute, about 2 minutes, about 4 minutes, about 5.5 minutes, about 1 hour, about 3 hr and about 21 hours after the compound treatment. In FIGS. 17B-H, each minute showed on the x-axis corresponds to one second in real measurement. It is clear that within 3 hr of compound treatment, the cardiomyocytes exhibit significant, time-dependent change in their impedance responses. For example, at about 1 hr after the treatment, the frequency of the impedance-based beating spikes is much higher than that for the cardiomyocytes before treatment, yet the magnitude is much smaller. On the other hand, at about 3 hr after treatment, the impedance-based beating pattern becomes rather irregular whilst the magnitude of the beating pattern has somewhat restored. Still, even at ~21 hrs after compound treatment, the impedance pattern did not restore and the beating frequency appeared to about 70% (at 50~60 beats per minute) of that before compound treatment (at 80~90 beats per minute). Yet the amplitude of the impedance response spikes increased by about 50% compared with that before compound treatment. FIG. 18 and FIG. 19 show the analysis results of the impedance beating pattern of FIG. 17 in terms of the beating frequency (beats per minute) and the beating magnitude. For FIG. 18 and FIG. 19, each unit (1) on the x-axis corresponds to 0.016 second (16 milli-seconds) in real measurement.

What is claimed is:

1. A system for monitoring impedance of excitable cells in vitro, comprising:
   a) a device for monitoring cell-substrate impedance at 20 millisecond resolution, the device comprising i) a nonconductive substrate;
ii) one or more electrode arrays fabricated on said substrate;
iii) one or more wells on said substrate, wherein each of said one or more arrays is associated with one of said one or more wells; wherein each electrode array is individually addressable, further wherein said substrate has a surface suitable for cell attachment, wherein said cell attachment on said substrate can result in a detectable change in impedance between electrodes within each electrode array;

b) an impedance analyzer capable of impedance measurement at 20 millisecond time resolution;
c) electronic circuitry that can engage said device and selectively connect said two or more electrode arrays of said device to said impedance analyzer; and
d) a software program that controls said electronic circuitry and records and analyzes data obtained from said impedance analyzer.

2. The system according to claim 1, wherein each of said electrode arrays comprises two electrode structures having substantially a same surface area.

3. The system according to claim 2, wherein said electrode structures are each constructed from a material selected from the group consisting of metal, gold, platinum, titanium and chromium.

4. The system according to claim 2, wherein said electrode structures have a width between 20 microns and 500 microns.

5. The system according to claim 2, wherein a gap between electrode structures within each electrode array is between 5 microns and 100 microns.

6. The system according to claim 1, wherein each electrode array is organized in a configuration selected from the group consisting of interdigitated, circle-on-line, diamond-on-line, concentric, sinusoidal, and castellated.

7. The system according to claim 1, wherein said 20 millisecond time resolution allows for impedance measurements at more than two time points within each excitation cycle of excitable cells introduced to wells.

8. The system according to claim 7, wherein said excitation cycle is a cell beating cycle.

9. The system according to claim 8, wherein said excitable cells are cardiomyocytes.

10. The system according to claim 7, wherein said excitable cells undergo excitation-contraction coupling.

11. The system according to claim 1, wherein said impedance measurement at 20 millisecond time resolution comprises at least two consecutive impedance measurements 20 milliseconds or less apart.

12. The system according to claim 11, wherein said at least two consecutive impedance measurements are less than 10 milliseconds apart.

13. The system according to claim 1, wherein said one or more wells is selected from the group consisting of 6 wells, 8 wells, 16 wells, 32 wells, 96 wells and 384 wells.

* * * * *